(12) United States Patent
Simon et al.

(10) Patent No.: US 9,174,045 B2
(45) Date of Patent: Nov. 3, 2015

(54) NON-INVASIVE ELECTRICAL AND MAGNETIC NERVE STIMULATORS USED TO TREAT OVERACTIVE BLADDER AND URINARY INCONTINENCE

(75) Inventors: Bruce J. Simon, Mountain Lakes, NJ (US); Joseph P. Errico, Warren, NJ (US); John T. Raffle, Austin, TX (US)

(73) Assignee: Electrocore, LLC, Basking Ridge, NJ (US)

( * ) Notice: Subject to any disclaimer, the term of this patent is extended or adjusted under 35 U.S.C. 154(b) by 1016 days.

(21) Appl. No.: 13/279,437

(22) Filed: Oct. 24, 2011

(65) Prior Publication Data

US 2012/0101326 A1     Apr. 26, 2012

Related U.S. Application Data

(63) Continuation-in-part of application No. 13/222,087, filed on Aug. 31, 2011, which is a continuation-in-part of application No. 13/183,765, filed on Jul. 15, 2011, now Pat. No. 8,874,227, and a continuation-in-part of (Continued)

(51) Int. Cl.
| | | |
|---|---|---|
| *A61N 1/18* | (2006.01) | |
| *A61N 1/36* | (2006.01) | |
| *A61N 1/04* | (2006.01) | |
| *A61N 2/00* | (2006.01) | |

(52) U.S. Cl.
CPC .......... *A61N 1/36007* (2013.01); *A61N 1/0456* (2013.01); *A61N 2/006* (2013.01); *A61N 1/36014* (2013.01)

(58) Field of Classification Search
CPC ............ A61N 1/36007; A61N 1/0456; A61N 1/0551; A61N 1/36014
USPC ............................... 607/40, 41, 133, 143, 145
See application file for complete search history.

(56) References Cited

U.S. PATENT DOCUMENTS

| | | |
|---|---|---|
| 4,196,737 A | 4/1980 | Bevilacqua |
| 5,983,131 A | 11/1999 | Weaver et al. |
| 2005/0261542 A1 | 11/2005 | Riehl |
| 2006/0074284 A1 | 4/2006 | Juola et al. |
| 2007/0123952 A1 | 5/2007 | Strother et al. |
| 2007/0150024 A1 | 6/2007 | Leyde et al. |
| 2007/0276449 A1 | 11/2007 | Gunter et al. |
| 2008/0071329 A1 | 3/2008 | Giuntoli et al. |
| 2008/0306325 A1 | 12/2008 | Burnett et al. |
| 2009/0227829 A1* | 9/2009 | Burnett et al. .................. 600/12 |

(Continued)

OTHER PUBLICATIONS

International Search Report and Written Opinion of the International Searching Authority dated Dec. 3, 2011, PCT application PCT/US11/47509, International Filing Date Aug. 12, 2011.

(Continued)

*Primary Examiner* — Tammie K Heller
(74) *Attorney, Agent, or Firm* — Dentons US LLP

(57) ABSTRACT

Transcutaneous electrical and magnetic nerve stimulation devices and methods generate energy that is delivered noninvasively to selected nerve fibers within the patient to treat lower urinary tract disorders. The disorders comprise overactive bladder, urge incontinence, stress, incontinence, urge frequency, non-obstructive urinary retention and interstitial cystitis/painful bladder syndrome. In preferred embodiments, a posterior tibial nerve of a patient is stimulated non-invasively to treat bladder disorders.

37 Claims, 11 Drawing Sheets

Related U.S. Application Data application No. 13/183,721, filed on Jul. 15, 2011, now Pat. No. 8,676,324, and a continuation-in-part of application No. 13/109,250, filed on May 17, 2011, now Pat. No. 8,676,330, and a continuation-in-part of application No. 13/075,746, filed on Mar. 30, 2011, now Pat. No. 8,874,205, and a continuation-in-part of application No. 13/005,005, filed on Jan. 12, 2011, now Pat. No. 8,868,177, which is a continuation-in-part of application No. 12/964,050, filed on Dec. 9, 2010, now abandoned, which is a continuation-in-part of application No. 12/859,568, filed on Aug. 19, 2010, now Pat. No. 9,037,247, said application No. 12/859,568 is a continuation-in-part of application No. 12/408,131, filed on Mar. 20, 2009, now Pat. No. 8,812,112, and a continuation-in-part of application No. 12/612,177, filed on Nov. 4, 2009, now Pat. No. 8,041,428.

(60) Provisional application No. 61/488,208, filed on May 20, 2011, provisional application No. 61/487,439, filed on May 18, 2011, provisional application No. 61/471,405, filed on Apr. 4, 2011, provisional application No. 61/451,259, filed on Mar. 10, 2011, provisional application No. 61/415,469, filed on Nov. 19, 2010.

(56) References Cited

U.S. PATENT DOCUMENTS

| | | | |
|---|---|---|---|
| 2009/0281593 | A9 | 11/2009 | Errico et al. |
| 2010/0004716 | A1 | 1/2010 | Zimmerling et al. |
| 2011/0046432 | A1 | 2/2011 | Simon et al. |
| 2012/0197339 | A1* | 8/2012 | Takagi et al. ............... 607/41 |
| 2013/0006322 | A1* | 1/2013 | Tai ............................. 607/39 |

OTHER PUBLICATIONS

International Search Report and Written Opinion of the International Searching Authority dated Dec. 22, 2011, PCT application PCT/US11/49844, International Filing Date Aug. 30, 2011.
Abarbanel et al. Estimation of parameters in nonlinear systems using balanced synchronization. Physical Review E 77(2008):016208, pp. 1-14.
Abram. Transcutaneous Electrical Nerve Stimulation. pp. 1-10 in: Joel B. Myklebust, ed. Neural stimulation (vol. 2). Boca Raton, Fla. CRC Press 1985.
Abrams et al. Chimera States for Coupled Oscillators. Phys. Rev. Lett. 93(2004), 174102, pp. 1-4.
Abrams et al. Sub-committee of the International Continence Society. The standardisation of terminology of lower urinary tract function: report from the Standardisation Sub-committee of the International Continence Society. Neurourol Urodyn. 21(2,2002): 167-78.
Alexelonescu et al. Effect of composition on the dielectric properties of hydrogels for biomedical applications. Physiol. Meas. 31 (2010) S169-S182.
Al-Hayek et al. Does the patient's position influence the detection of detrusor overactivity? Neurourol Urodyn. 27(4,2008): 279-86.
Alon et al. Effects of Electrode Size on Basic Excitatory Responses and on Selected Stimulus Parameters. Journal of Orthopaedic and Sports Physical Therapy. 20(1,1994):29-35.
Al-Shaiji et al. Pelvic electrical neuromodulation for the treatment of overactive bladder symptoms. Adv Urol. 2011;2011:757454.
Amarenco et al. Urodynamic effect of acute transcutaneous posterior tibial nerve stimulation in overactive bladder. J Urol. 169(6,2003):2210-5.
Amend et al. How does neuromodulation work. Neurourol Urodyn. 30(5,2011):762-5.
Andersson et al. Pharmacology of the lower urinary tract: basis for current and future treatments of urinary incontinence. Pharmacol Rev. 56(4,2004):581-631.
Andersson et al. Pharmacological treatment of overactive bladder: report from the International Consultation on Incontinence. Curr Opin Urol. 19(4,2009):380-94.
Andersson. Storage and voiding symptoms: pathophysiologic aspects. Urology 62 (5, Supp. 2, 2003): 3-10.
Apostolidis. Neuromodulation for intractable OAB. Neurourol Urodyn. Jun. 2011;30(5):766-70.
Athanasopoulos et al. Pharmacotherapy of urinary incontinence. Int Urogynecol J Pelvic Floor Dysfunct. 20(4,2009):475-82.
Aydin et al. Transcutaneous electrical nerve stimulation versus baclofen in spasticity: clinical and electrophysiologic comparison. Am J Phys Med Rehabil. 84(8,2005): 584-92.
Berghmans et al. Electrical stimulation with non-implanted electrodes for urinary incontinence in adults. Cochrane database of systematic reviews 2004 (updated 2009), Issue 3, pp. 1-9.
Bergstrom et al. Improvement of urge- and mixed-type incontinence after acupuncture treatment among elderly women—a pilot study. J Auton Nerv Syst. 79.
Bertram et al. Aperiodic flow-induced oscillations of collapsible tubes: a critical reappraisal. Med Eng Phys. 26(3,2004):201-14.
Bertram. Flow phenomena in floppy tubes. Contemporary Physics 45 (1,2004): 45-60.
Birder et al. Neural Control (Committee 3), In: Incontinence (International Consultation on Incontinence, 4th edition, 2009), Paul Abrams, Linda Cardozo, Saad Khoury, and Alan Wein, eds. Health Publications, Ltd., distributed by Editions 21, 76 Rue de la Pompe 75016 France., pp. 167-254.
Bock et al. CIBA Foundation Symposium 151. Neurobiology of Incontinence. (1990) New York: Wiley, p. 107.
Borckardt et al. Reducing Pain and Unpleasantness During Repetitive Transcranial Magnetic Stimulation. Journal of ECT 2006; 22:259-264.
Brading. A myogenic basis for the overactive bladder. Urology 50(6A Suppl,1997):57-67.
Brading. Spontaneous activity of lower urinary tract smooth muscles: correlation between ion channels and tissue function. J Physiol. 570(Pt 1,2006): 13-22.
Brennen. The Characterization of Transcutaneous Stimulating Electrodes. IEEE Transactions on Biomedical Engineering BME-23 (4,1976): 337-340.
Bristow et al. Ambulatory urodynamics. Br J Urol. 77(3,1996): 333-8.
Burks et al. Neuromodulation and the neurogenic bladder. Urol Clin North Am. 37(4,2010): 559-65.
Burton et al. Pain Suppression by Transcutaneous Electronic Stimulation. IEEE Transactions on Biomedical Engineering BME-21(2,1974): 81-88.
But I. Conservative treatment of female urinary incontinence with functional magnetic stimulation. Urology 61(3,2003): 558-61.
Campbell, J A. A critical appraisal of the electrical output characteristics of ten transcutaneous nerve stimulators. Clin. phys. Physiol. Meas. 3(2,1982): 141-150.
Carbunaru et al. Toroidal coil models for transcutaneous magnetic stimulation of nerves. IEEE Transactions on Biomedical Engineering 48 (4,2001): 434-441.
Chai et al. Neurophysiology of micturition and continence. Urol Clin North Am. 23(2,1996): 221-36.
Chapple et al. The role of urinary urgency and its measurement in the overactive bladder symptom syndrome: current concepts and future prospects. BJU Int. 95(3,2005):335-40.
Cherniack. Biofeedback and other therapies for the treatment of urinary incontinence in the elderly. Altern Med Rev. 11(3,2006):224-31.
Cilliers. Analysis of the current density distribution due to surface electrode stimulation of the human body. Ph.D. Dissertation, Ohio State University, 1988. (UMI Microform No. 8820270, UMI Company, Ann Arbor MI).
Ciszak et al. Sharp versus smooth synchronization transition of locally coupled oscillators. Phys. Rev. E 78(2008), 016202, pp. 1-4.
Cogan. Neural Stimulation and Recording Electrodes. Annu. Rev. Biomed. Eng. 2008. 10:275-309.
Collins et al. Potential for control of detrusor smooth muscle spontaneous rhythmic contraction by cyclooxygenase products released by interstitial cells of Cajal. J Cell Mol Med 13(9B,2009):3236-50.

(56) References Cited

OTHER PUBLICATIONS

Constantinou et al. Multiple-coupled pacemaker system in renal pelvis of the unicalyceal kidney. Am J Physiol. 241(5,1981):R412-8.
Coskey. Contact dermatitis caused by ECG electrode jelly. Arch Dermatol 113(1977): 839-840.
Dasgupta et al. Cerebral mechanisms and voiding function. BJU Int 99(4,2007):731-4.
Datta et al. Transcranial current stimulation focality using disc and ring electrode configurations: FEM analysis. J. Neural Eng. 5 (2008) 163-174.
De Gennaro et al. Current state of nerve stimulation technique for lower urinary tract dysfunction in children. J Urol. 185(5,2011): 1571-7.
De Groat et al. Pharmacology of the lower urinary tract. Annu Rev Pharmacol Toxicol. 41(2001): 691-721.
De Groat. A neurologic basis for the overactive bladder. Urology 50(6A Suppl,1997):36-52; discussion 53-6.
De Groat. Integrative control of the lower urinary tract: preclinical perspective. Br J Pharmacol.147(Suppl 2,2006):S25-40.
De Seze et al. Transcutaneous posterior tibial nerve stimulation for treatment of the overactive bladder syndrome in multiple sclerosis: results of a multicenter prospective study. Neurourol Urodyn. 30(3,2011):306-11.
De Wachter et al. Frequency-volume charts: a tool to evaluate bladder sensation. Neurourol Urodyn. 22(7,2003):638-42.
De Wachter S et al. How sudden is a compelling desire to void? An observational cystometric study on the suddenness of this sensation. BJU Int. 101(8,2008):1000-3.
Delitto et al. A Study of Discomfort with Electrical Stimulation. Phys. Ther. 1992; 72:410-424.
Delitto et al. Electrical stimulation of the quadriceps femoris in an elite weight lifter: a single subject experiment. Int J Sports Med 10(1989):187-191.
Doi et al. Noise-induced critical breakdown of phase lockings in a forced van der Pol oscillator. Physics Letters A 310 (5-6, 2003): 407-414.
Drake et al. Localized contractions in the normal human bladder and in urinary urgency. BJU Int. 95(7,2005):1002-5.
Drake et al. Model of peripheral autonomous modules and a myovesical plexus in normal and overactive bladder function. Lancet 358(9279,2001):401-3.
Drake. The Integrative Physiology of the Bladder. Ann R Coll Surg Engl. 89(6,2007): 580-585.
Duysens et al. Neural control of locomotion; The central pattern generator from cats to humans. Gait Posture. 7(2,1998):131-141.
Elkelini et al. Mechanisms of action of sacral neuromodulation. Int Urogynecol J. 21 (Suppl 2,2010): S439-46.
Engineer et al. Reversing pathological neural activity using targeted plasticity. Nature 470(7332,2011):101-4.
Evans et al. The effects of distention of the bladder on somatic reflexes in the cat. J. Physiol. 146(1959): 438-458.
Faierstein. Coil Designs for Localized and Efficient Magnetic Stimulation of the Nervous System. Ph.D. Dissertation, Department of Biomedical Engineering, Case Western Reserve, May 1999. (UMI Microform No. 9940153, UMI Company, Ann Arbor MI).
Feynman et al. The Feynman Lectures on Physics. vol. II. Addison-Wesley Publ. Co. (Reading MA, 1964), p. 15-15.
Filipovic et al. Finite Element Modeling of a Transient Functional Electrical Stimulation. Journal of the Serbian Society for Computational Mechanics 1 (1, 2007):154-163.
Finazzi-Agro et al. Percutaneous tibial nerve stimulation effects on detrusor overactivity incontinence are not due to a placebo effect: a randomized, double-blind, placebo controlled trial. J Urol. 184(5,2010): 2001-6.
Finazzi-Agro et al. Percutaneous tibial nerve stimulation produces effects on brain activity: study on the modifications of the long latency somatosensory evoked potentials. Neurourol Urodyn. 28(4,2009): 320-4.
Findlay et al. Posterior tibial nerve stimulation and faecal incontinence: a review. Int J Colorectal Dis. 26(3,2011):265-73.
Forrester et al. Effect of Electrode Size, Shape, and Placement During Electrical Stimulation. The Journal of Applied Research 4, (2, 2004): 346-354.
Fujishiro et al. Magnetic stimulation of the sacral roots for the treatment of urinary frequency and urge incontinence: an investigational study and placebo controlled trial. J Urol 168(3,2002):1036-9.
Galloway et al. Extracorporeal magnetic innervation therapy for stress urinary incontinence. Urology 53(1999): 1108-11.
Garry et al. Reflexes involving the external urethral sphincter in the cat. J Physiol. 149(1959):653-65.
Gaunt et al. Control of urinary bladder function with devices: successes and failures. Prog Brain Res. 152(2006): 163-94.
Geddes et al. Stimulation with capacitor electrodes. Med. and Biol. Eng. and Comput. 25(1987):359-360.
Geddes. Historical Evolution of Circuit Models for the Electrode-Electrolyte Interface. Annals of Biomedical Engineering 25 (1997):1-14.
Geirsson et al. Traditional acupuncture and electrical stimulation of the posterior tibial nerve. A trial in chronic interstitial cystitis. Scand J Urol Nephrol. 27(1,1993):67-70.
Geuze. Two methods for homogeneous field defibrillation and stimulation. Med. and Biol. Eng. and Comput. 21(1983), 518-520.
Gillespie. The autonomous bladder: a view of the origin of bladder overactivity and sensory urge. BJU Int 93(4,2004):478-83.
Gilling et al. A double-blind randomized controlled trial of electromagnetic stimulation of the pelvic floor vs sham therapy in the treatment of women with stress urinary incontinence. BJU International 103 (10,2009): 1386-1390.
Goode et al. Incontinence in older women. JAMA. 303(21,2010): 2172-81.
Gopal et al. Discontinuation rates of anticholinergic medications used for the treatment of lower urinary tract symptoms. Obstet Gynecol. 112(6,2008):1311-8.
Govier et al. Percutaneous afferent neuromodulation for the refractory overactive bladder: results of a multicenter study. J Urol. 165(4,2001):1193-8.
Green et al. Conducting polymer-hydrogels for medical electrode applications. Sci. Technol. Adv. Mater. 11 (2010) 014107 (13ppSIGNAGEL Electrode Gel from Parker Laboratories, Inc., 286 Eldridge Rd., Fairfield NJ 07004.
Green et al. Electrical percutaneous tibial stimulation modulates within-a-breath respiratory drive in man. Respir Physiol Neurobiol. 161(2,2008):214-7.
Griffiths et al. Control and coordination of bladder and urethral function in the brainstem of the cat. Neurourology and Urodynamics 9 (1, 1990): 63-82.
Grill et al. Stimulus waveforms for selective neural stimulation. IEEE Eng. Med. Biol. 14 (1995): 375-385.
Guevara. Bifurcations involving fixed points and limit cycles in biological systems. In: "Nonlinear Dynamics in Physiology and Medicine", edited by Beuter A., Glass L., Mackey M.C., Titcombe M.S. Springer-Verlag, New York, pp. 41-85 (2003).
Hakkinen et al. Which structures are sensitive to painful transcranial stimulation? Electromyogr. clin. Neurophysiol. 1995, 35:377-383.
Hartmann et al. Treatment of overactive bladder in women. Evid Rep Technol Assess (Full Rep). 187(2009): 1-120.
Heimburg et al. On soliton propagation in biomembranes and nerves. PNAS 102 (28, 2005): 9790-9795.
Henderson et al. Overactive bladder. Maturitas. 2010 66(3,2010):257-62.
Hennings. Selective Electrical Stimulation of Peripheral Nerve Fibers: Accommodation Based Methods. Ph.D. Thesis, Center for Sensory-Motor Interaction, Aalborg University, Aalborg, Denmark, 2004.
Hu et al. Costs of urinary incontinence and overactive bladder in the United States: a comparative study. Urology. 63(3,2004): 461-465.
Hu et al. Current Density Distribution Under Surface Electrode on Posterior Tibial Nerve Electrical Stimulation. Proceedings of the 2005 IEEE Engineering in Medicine and Biology 27th Annual Conference Shanghai, China, Sep. 1-4, 2005: 3650-3652.
Irwin et al. EPIC Study Group. Understanding the elements of overactive bladder: questions raised by the EPIC study. JU Int. 101(11,2008):1381-7.

(56) References Cited

OTHER PUBLICATIONS

Irwin et al. Population-based survey of urinary incontinence, overactive bladder, and other lower urinary tract symptoms in five countries: results of the EPIC study. Eur Urol. 50(6,2006): 1306-14.

Johnson et al. Analgesic effects of different pulse patterns of transcutaneous electrical nerve stimulation on cold-induced pain in normal subjects. Journal of Psychosomatic Research 35 (2/3, 1991):313-321e.

Kai et al. Efficacy of High-frequency Magnetic Stimulation of the Sacral Root in Patients with Urinary Incontinence Following a Radical Prostatectomy. LUTS (2010) DOI: 10.1111/j.1757-5672.2010. 00062.x, pp. 1-5.

Kanai et al. Bladder Afferent Signaling: Recent Findings. J Urol 183(4, 2010):1288-95.

Kanai et al. Origin of spontaneous activity in neonatal and adult rat bladders and its enhancement by stretch and muscarinic agonists. Am J Physiol Renal Physiol 292(3,2007): F1065-72.

Keller et al. Electrodes for transcutaneous (surface) electrical stimulation. Journal of Automatic Control, University of Belgrade 18(2,2008):35-45.

Keller et al. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197.

Kim et al. Uniformity of current density under stimulating electrodes. Critical Reviews in Biomedical Engineering 17(1990,6): 585-619.

Kinder et al. Neuronal circuitry of the lower urinary tract; central and peripheral neuronal control of the micturition cycle. Anat Embryol (Berl). Sep. 1995;192(3):195-209.

Konishi. Experimental evidence for amplitude death induced by dynamic coupling: van der Pol oscillators. Proc. ISCAS (4,2004) 792-795.

Kori et al. Entrainment of Randomly Coupled Oscillator Networks by a Pacemaker. Phys. Rev. Lett. 93(2004), 254101, pp. 1-4.

Ksienski. A Minimum Profile Uniform Current Density Electrode. IEEE Transactions on Biomedical Engineering 39 (7,1992): 682-692.

Kuhn et al. A 3D transient model for transcutaneous functional electrical stimulation. Proc. 10th Annual Conference of the International FES Society Jul. 2005—Montreal, Canada: pp. 1-3.

Kuhn et al. A model for transcutaneous current stimulation: simulations and experiments. Med Biol Eng Comput 47(2009):279-289.

Kuhn et al. Array electrode design for transcutaneous electrical stimulation: A simulation study. Medical Engineering & Physics 31 (2009) 945-951.

Kuiken et al. Finite Element Modeling of Electromagnetic Signal Propagation in a Phantom Arm. IEEE Transactions on Neural Systems and Rehabilitation Engineering 9 (4,2001): 346-354.

Kulseng-Hanssen et al. Urethral pressure variations in females with and without neurourological symptoms. Scand J Urol Nephrol Suppl. 114(1988):48-52.

Kulseng-Hanssen. Prevalence and pattern of unstable urethral pressure in one hundred seventy-four gynecologic patients referred for urodynamic investigation. Am J Obstet Gynecol. 146(8,1983): 895-900.

Lagou et al. Muscarinic stimulation of the mouse isolated whole bladder: physiological responses in young and ageing mice. Auton Autacoid Pharmacol. 26(3,2006):253-60.

Lang et al. Pyeloureteral motility and ureteral peristalsis: essential role of sensory nerves and endogenous prostaglandins. Exp Physiol. 87(2,2002):129-46.

Laufer et al. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10,2008):1167-1176.

Le Feber et al. Pudendal nerve stimulation induces urethral contraction and relaxation. Am J Physiol. Nov. 1999;277(5 Pt 2):R1368-75.

Lee et al. Dynamics and pattern formation in large systems of spatially-coupled oscillators with finite response times. Chaos 21 (2, 2011), pp. 023122-023122-14.

Lee et al. The overactive bladder: new concepts of etiology and treatment. Curr Bladder Dysfunct Rep 5(2010): 126-134.

Leng et al. How sacral nerve stimulation neuromodulation works. Urol Clin North Am. 32(1,2005): 11-8.

Lentz. Urogynecology: physiology of micturition, diagnosis of voiding dysfunction, and incontinence: surgical and nonsurgical treatment. In: Katz VL, Lentz GM, Lobo RA, Gershenson DM, eds. Comprehensive Gynecology. 5th ed. Philadelphia, Pa: Mosby Elsevier; 2007: chap 21, pp. 537-568.

Liao et al. Noninvasive electrical impedance analysis to measure human urinary bladder volume. J Obstet Gynaecol Res. 37(8,2011):1071-5.

Liboff. Signal shapes in electromagnetic therapies: a primer. pp. 17-37 in: Bioelectromagnetic Medicine (Paul J. Rosch and Marko S. Markov, eds.). New York: Marcel Dekker (2004).

Lim et al. The treatment of overactive bladder syndrome refractive to antimuscarinic therapy. Incont Pelvic Floor Dysfunct 2(Suppl. 1, 2008) 29-32.

Lyons et al. An investigation of the effect of electrode size and electrode location on comfort during stimulation of the gastrocnemius muscle. Medical Engineering & Physics 26 (2004) 873-878.

MacDiarmid et al. Long-term Durability of Percutaneous Tibial Nerve Stimulation for the Treatment of Overactive Bladder. J Urol 183(2010):234-240.

Matthews et al. Dynamics of a large system of coupled nonlinear oscillators. Physica D: Nonlinear Phenomena 52 (2-3,1991): 293-331.

Matthews et al. Phase diagram for the collective behavior of limit-cycle oscillators. Phys. Rev. Lett. 65(1990): 1701-1704.

Maus et al. Imaging of Nonuniform Current Density at Microelectrodes by Electrogenerated Chemiluminescence. Anal. Chem. 71(1999): 4944-4950.

McIntyre et al. Finite Element Analysis of the Current-Density and Electric Field Generated by Metal Microelectrodes. Annals of Biomedical Engineering 29 (2001): 227-235.

McPherson. The effects of somatic stimuli on the bladder in the cat. J. Physiol. 185(1966): 185-196.

Meng. Recent research advances in the pathophysiology of overactive bladder. Incont Pelvic Floor Dysfunct 3(Suppl 1,2009): 5-7.

Nakamura et al. Transcutaneous electrical stimulation for the control of frequency and urge incontinence. Hinyokika Kiyo. 29(9,1983):1053-9.

Nitti et al. Urinary Incontinence: Epidemiology, Pathophysiology, Evaluation, and Management Overview. Chapter 60 In: Campbell-Walsh Urology, 9th ed.

Nolan. Conductive differences in electrodes used with transcutaneous electrical nerve stimulation devices. Physical Therapy 71(1991):746-751.

Okada et al. Transcutaneous electrical stimulation of thigh muscles in the treatment of detrusor overactivity. Br J Urol. 81(4,1998):560-4.

Papa. Detrusor instability and low compliance may represent different levels of disturbance in peripheral feedback control of the micturition reflex. Neurourol Urodyn. 18(2,1999):81-91.

Papa. The female pelvic floor: function, dysfunction and management according to the integral theory. 3rd ed. Chapter 6: Mapping the Dynamics of Connective Tissue Dysfunction. Dordrecht : Springer, 2010.

Park et al . The guarding reflex revisited. Br J Urol. 80(6,1997):940-5.

Patriciu et al. Current Density Imaging and Electrically Induced Skin Burns Under Surface Electrodes. IEEE Transactions on Biomedical Engineering 52 (12,2005): 2024-2031.

Patriciu et al. Investigation of current densities produced by surface electrodes using finite element modeling and current density imaging. Proceedings of the 23rd Annual EMBS International Conference, Oct. 25-28, 2001, Istanbul, Turkey: 2403-2406.

Petrofsky et al. Current distribution under electrodes in relation to stimulation current and skin blood flow: are modern electrodes really providing the current distribution during stimulation we believe they are? Journal of Medical Engineering and Technology 30 (6,2006): 368-381.

(56) References Cited

OTHER PUBLICATIONS

Petrofsky et al. The transfer of current through skin and muscle during electrical stimulation with sine, square, Russian and interferential waveforms. Journal of Medical Engineering and Technology 33 (2,2009): 170-181.
Piccardi. Parameter estimation for systems with peak-to-peak dynamics. International Journal of Bifurcation and Chaos (IJBC) 18(3,2008): 745-753.
Pinto et al. Central pattern generators for bipedal locomotion. J Math Biol. 53(3,2006):474-89.
Popovic et al. Automatic determination of the optimal shape of a surface electrode: Selective stimulation. Journal of Neuroscience Methods 178 (2009) 174-181.
Popovic-Bijelic et al. Multi-Field Surface Electrode for Selective Electrical Stimulation. Artificial Organs 29 (6,2005):448-452.
Prausnitz. The effects of electric current applied to skin: A review for transdermal drug delivery. Advanced Drug Delivery Reviews 18 (1996) 395-425.
Price et al. Pelvic floor exercise for urinary incontinence: a systematic literature review. Maturitas. 67(4,2010): 309-15.
Quinn et al. Assessment of an electronic daily diary in patients with overactive bladder. BJU Int. 91(7,2003):647-52.
Rahn et al. Pathophysiology of urinary incontinence, voiding dysfunction, and overactive bladder. Obstet Gynecol Clin North Am. 36(3,2009):463-74.
Rattay. The basic mechanism for the electrical stimulation of the nervous system. Neuroscience 89 (2, 1999):335-346.
Reichel et al. Simulation of the Three-Dimensional Electrical Field in the Course of Functional Electrical Stimulation. Artificial Organs 26(3,2002):252-255.
Roberts. Neurophysiology in neurourology. Muscle Nerve. 38(1,2008): 815-36.
Roosen et al. Characteristics of spontaneous activity in the bladder trigone. Eur Urol. 56(2,2009):346-53.
Rubenstein et al. Current Density Profiles of Surface Mounted and Recessed Electrodes for Neural Prostheses. IEEE Transactions on Biomedical Engineering BME-34 (11,1987): 864-875.
Sagi_Dolev et al. Three-dimensional current density distribution under surface stimulation electrodes. Med. and Biol. Eng. and Comput. 33(1995): 403-408.
Sawicki et al. Mathematical Modelling of Vagus Nerve Stimulation. pp. 92-97 in: Krawczyk, A. Electromagnetic Field, Health and Environment: Proceedings of EHE'07. Amsterdam, IOS Press, 2008.
Schilder et al. Computing Arnold Tongue Scenarios. Journal of Computational Physics 220 (2006): 932-951.
Schreiner et al. Randomized trial of transcutaneous tibial nerve stimulation to treat urge urinary incontinence in older women. INT Urogynecol J. 21(9,2010):1065-70.
Sen et al. Collective dynamics of delay-coupled limit cycle oscillators. PRAMANA (64,2005): 465-482.
Sha et al. The effect of the impedance of a thin hydrogel electrode on sensation during functional electrical stimulation. Medical Engineering & Physics 30 (2008): 739-746.
Starkman et al. Surgical options for drug-refractory overactive bladder patients. Rev Urol 12(2-3,2010):e97-e110.
Steers. Pathophysiology of overactive bladder and urge urinary incontinence. Rev Urol. 4 (Suppl 4,2002):S7-S18.
Suihko. Modelling the response of scalp sensory receptors to transcranial electrical stimulation. Med. Biol. Eng. Comput., 2002, 40, 395-401.
Swett et al. Electrical stimulation of peripheral nerve. In: Electrical Stimulation Research Techniques, Michael M. Patterson and Raymond P. Kesner, eds. Academic Press. (New York, 1981) pp. 243-295.
Tai et al. Prolonged poststimulation inhibition of bladder activity induced by tibial nerve stimulation in cats. Am J Physiol Renal Physiol. 300(2,2011):F385-92.
Tai et al. Suppression of bladder overactivity by activation of somatic afferent nerves in the foot. JU Int. 107(2,2011):303-9.
Takahashi et al. Overactive bladder: magnetic versus electrical stimulation. Current Opinion in Obstetrics & Gynecology 15(5,2003): 429-33.
Tan et al. Which stop test is best? Measuring detrusor contractility in older females. J Urol. 169(3,2003): 1023-7.
Tyagi et al. The overactive bladder: Epidemiology and morbidity. Urol Clin North Am. 33(4,2006): 433-8.
UltraStim grid-pattern electrode, Axelggard Manufacturing Company, 520 Industrial Way, Fallbrook CA, 2011.
Van Balken et al. Percutaneous tibial nerve stimulation as neuromodulative treatment of chronic pelvic pain. Eur Urol. 43(2,2003):158-63.
Van Balken et al. The use of electrical devices for the treatment of bladder dysfunction: a review of methods. J Urol. 172(3,2004):846-51.
Van Der Pal et al. Current opinion on the working mechanisms of neuromodulation in the treatment of lower urinary tract dysfunction. Curr Opin Urol. 16(4,2006):261-7.
Van Doorn et al. Ambulatory urodynamics: extramural testing of the lower and upper urinary tract by Holter monitoring of cystometrogram, uroflowmetry, and renal pelvic pressures. Urologic Clinics of North America 23(3,1996): 345-371.
Vasavada et al. Electrical stimulation for storage and emptying disorders. Chapter 64 in Campbell-Walsh Urology, 9th ed., AJ Wein, LR Kavoussi, AC Novick, AW Partin and CA Peters, eds. Philadelphia, Pa: Saunders Elsevier; 2007. pp. 2147-2167.
Vereecken. Urethral instability: related to stress and/or urge incontinence? J Urol. 134(4,1985): 698-701.
Verhoeven et al. Decreasing pain in electrical nerve stimulation. Clinical Neurophysiology 117 (2006) 972-978.
Voss et al. Nonlinear dynamical system identification from uncertain and indirect measurements. International Journal of Bifurcation and Chaos 14(6,2004):1905-1933.
Vuckovic et al. A comparative study of three techniques for diameter selective fiber activation in the vagal nerve: anodal block, depolarizing prepulses and slowly rising pulses. J. Neural Eng. 5 (2008): 275-286.
Vuckovic et al. Different Pulse Shapes to Obtain Small Fiber Selective Activation by Anodal Blocking—A Simulation Study. IEEE Transactions on Biomedical Engineering 51(5,2004):698-706.
Wai. Surgical treatment for stress and urge urinary incontinence. Obstet Gynecol Clin North Am. 36(3,2009):509-19.
Walsh et al. Transcutaneous electrical nerve stimulation: effect on peripheral nerve conduction, mechanical pain threshold, and tactile threshold in humans. Arch Phys Med Rehabil 79(1998):1051-1058.
Ward et al. Russian Electrical Stimulation: The Early Experiments. Physical Therapy 82 (10,2002): 1019-1030.
Ward. Electrical Stimulation Using Kilohertz-Frequency Alternating Current. Physical Therapy 89 (2,2009):181-190.
Weiss et al. Pacemaker activity in the upper urinary tract. J Smooth Muscle Res. 42(4,2006):103-15.
Whelan et al. Properties of rhythmic activity generated by the isolated spinal cord of the neonatal mouse. J Neurophysiol. 84(6,2000):2821-33.
White et al. Electroanalgesia: Its Role in Acute and Chronic Pain Management. Anesth Analg 92(2001):505-13.
Wyndaele. The normal pattern of perception of bladder filling during cystometry studied in 38 young healthy volunteers. J Urol. 160(2,1998): 479-81.
Yamanishi et al. Neuromodulation for the treatment of urinary incontinence. Int J Urol 15(2008):665-672.
Yoshimura et al. Physiology and pharmacology of the bladder and urethra. Chapter 56 in Campbell-Walsh Urology, 9th ed., AJ Wein, LR Kavoussi, AC Novick, AW Partin and CA Peters, eds. Philadelphia, Pa: Saunders Elsevier; 2007. pp. 1922-1972.

\* cited by examiner

FIG. 1
FIG. 1A
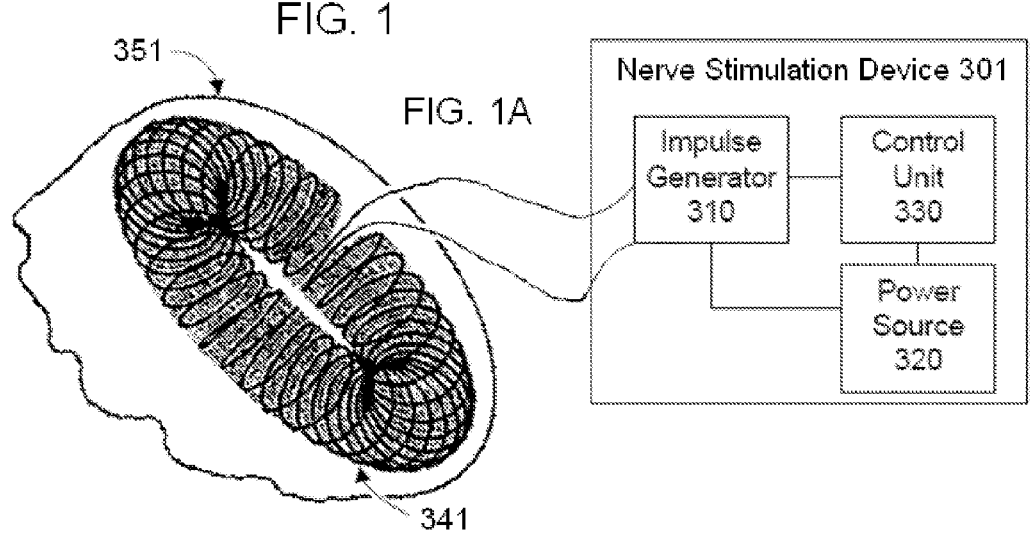
FIG. 1B
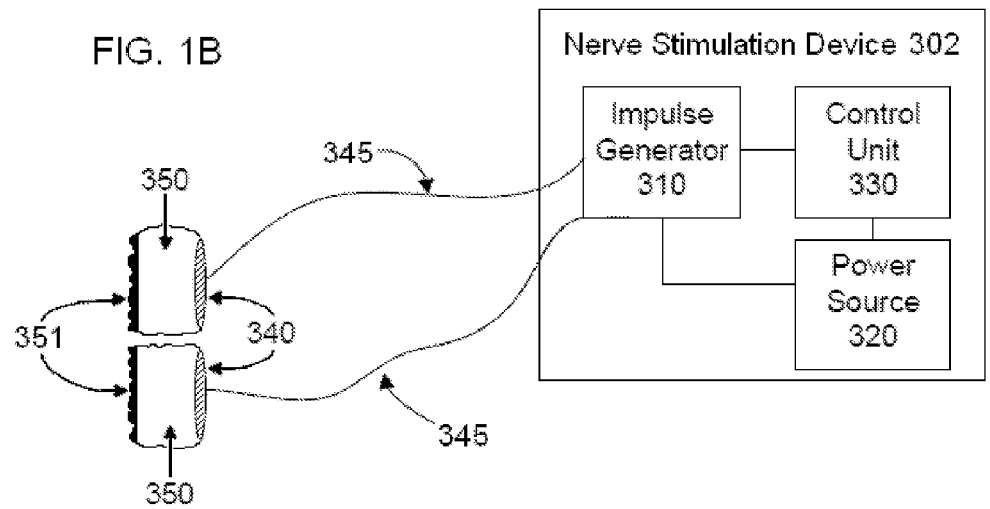

FIG. 2
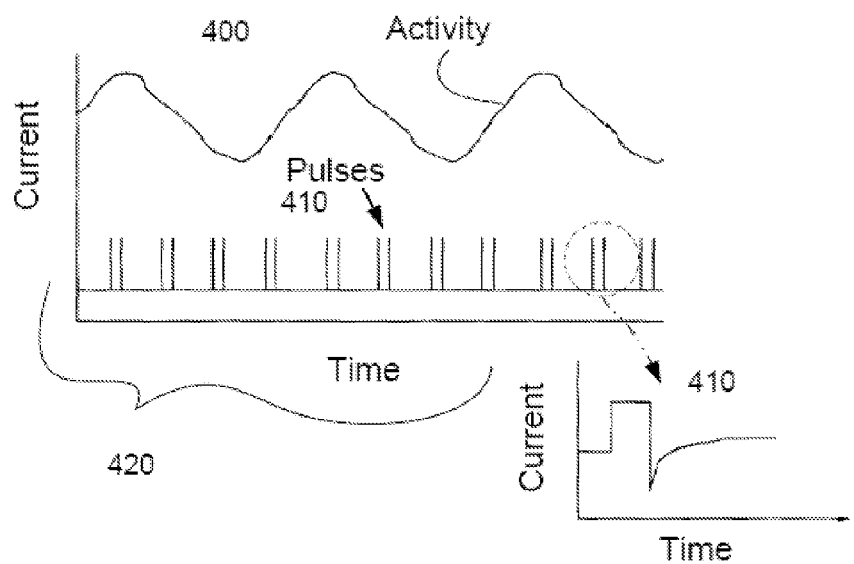
FIG. 2A
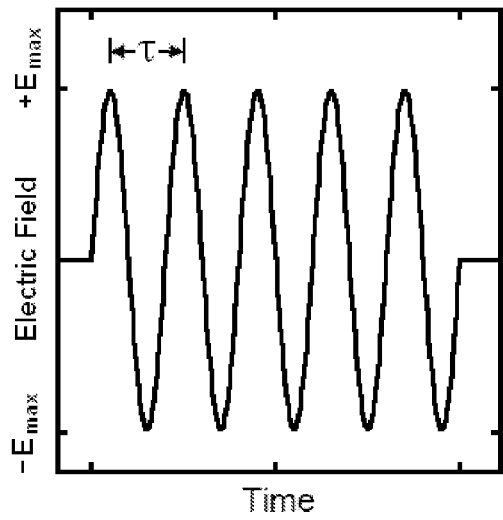
FIG. 2B
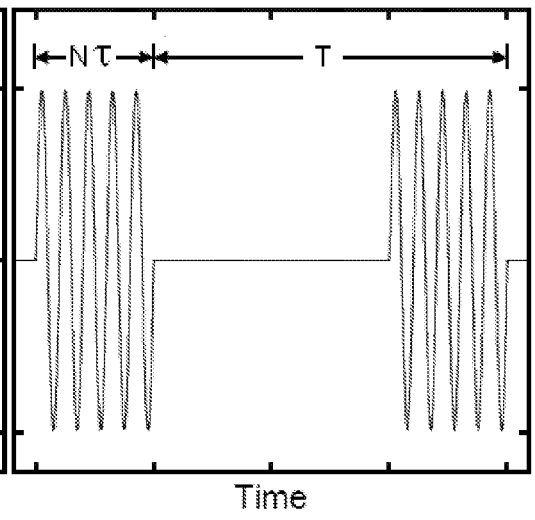
FIG. 2C

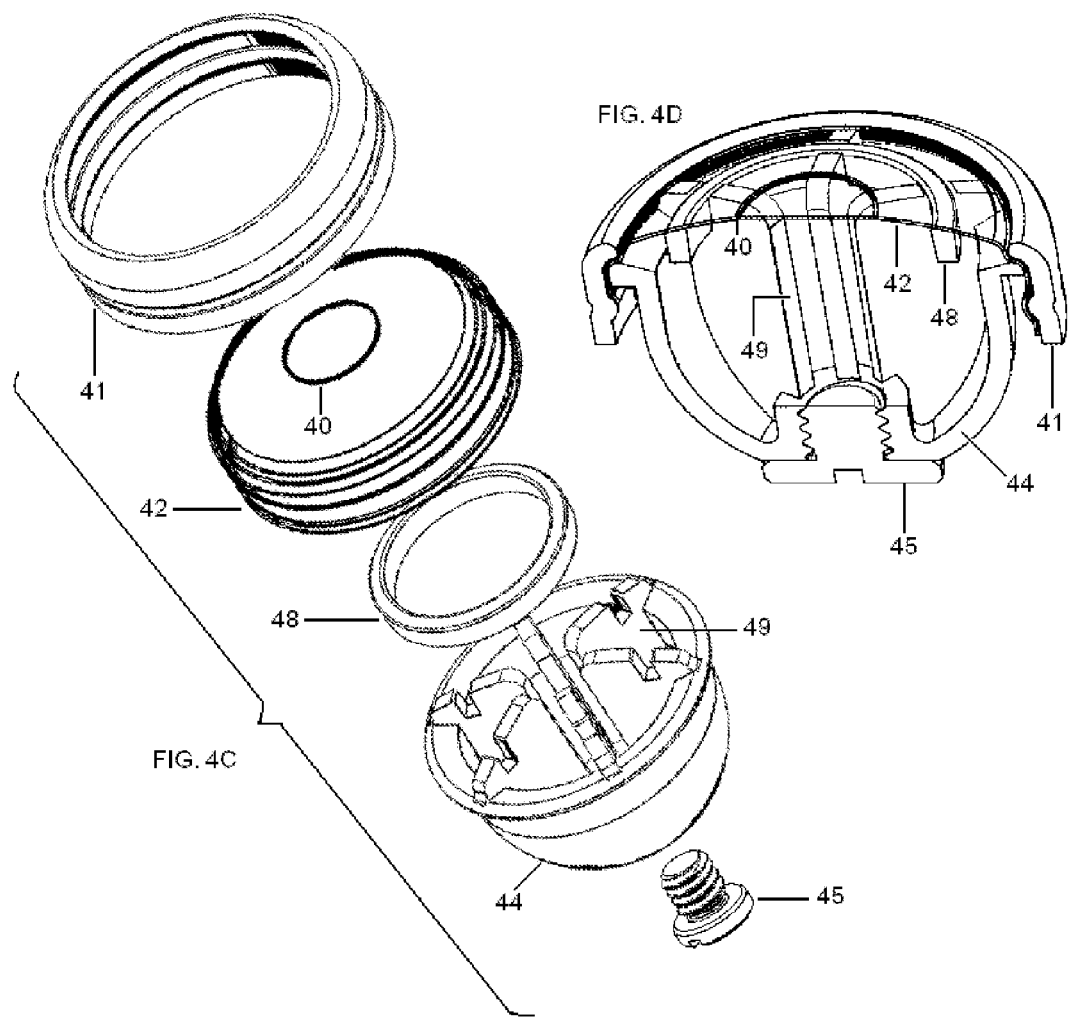

FIG. 7
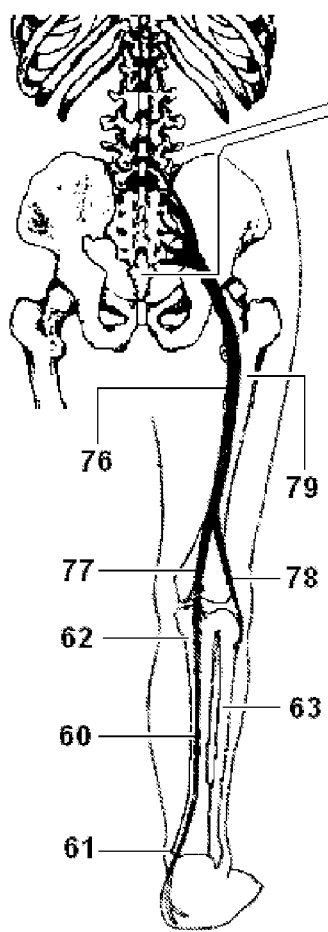
FIG. 7A
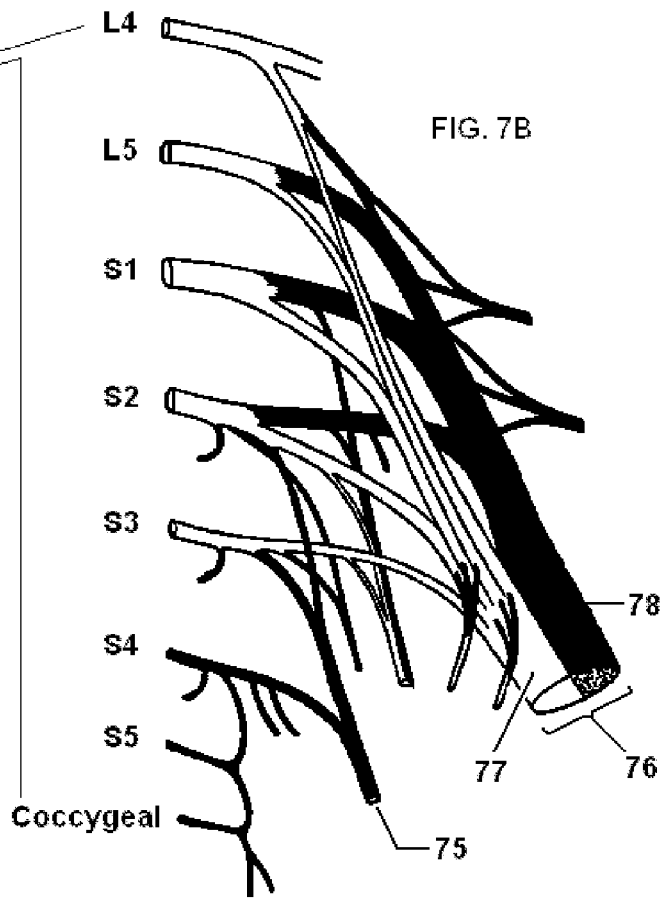
FIG. 7B

1 Phase Drift
2 Irregular Region
3 Phase Locked
4 Amplitude Death

1 Phase Drift

2 Irregular Region

3 Phase Locked

4 Amplitude Death

NON-INVASIVE ELECTRICAL AND MAGNETIC NERVE STIMULATORS USED TO TREAT OVERACTIVE BLADDER AND URINARY INCONTINENCE

CROSS REFERENCE TO RELATED APPLICATIONS

This application is a continuation-in-part of U.S. patent application Ser. No. 13/222,087 filed Aug. 31, 2011, presently pending, which is a continuation-in-part of U.S. patent application Ser. No. 13/183,765 filed Jul. 15, 2011, now U.S. Pat. No. 8,874,227 issued Oct. 28, 2014, which claims the benefit of U.S. Provisional Patent Application No. 61/488,208 filed May 20, 2011, and is a continuation-in-part to U.S. patent application Ser. No. 13/183,721 filed Jul. 15, 2011, now U.S. Pat. No. 8,676,324 issued Mar. 18, 2014, which claims the benefit of U.S. Provisional Patent Application No. 61/487,439 filed May 18, 2011, and is a continuation-in-part of U.S. patent application Ser. No. 13/109,250 filed May 17, 2011, now U.S. Pat. No. 8,676,330 issued Mar. 18, 2014, which claims the benefit of U.S. Provisional Patent Application No. 61/471,405 filed Apr. 4, 2011, and is a continuation-in-part of U.S. patent application Ser. No. 13/075,746 filed Mar. 30, 2011, now U.S. Pat. No. 8,874,205 issued Oct. 28, 2014, which claims the benefit of U.S. provisional patent application 61/451,259 filed Mar. 10, 2011, and is a continuation-in-part of U.S. patent application Ser. No. 13/005,005 filed Jan. 12, 2011, now U.S. Pat. No. 8,868,177 issued Oct. 21, 2014, which is a continuation-in-part of U.S. patent application Ser. No. 12/964,050 filed Dec. 9, 2010, now abandoned, which claims the benefit of U.S. Provisional Patent Application No. 61/415,469 filed Nov. 19, 2010, and is a continuation-in-part of U.S. patent application Ser. No. 12/859,568 filed Aug. 19, 2010, now U.S. Pat. No. 9,037,247, which is a continuation-in-part of U.S. patent application Ser. No. 12/408,131 filed Mar. 20, 2009, now U.S. Pat. No. 8,812,112 issued Aug. 19, 2014, and a continuation-in-part application of U.S. patent application Ser. No. 12/612,177 filed Nov. 4, 2009 now U.S. Pat. No. 8,041,428 issued Oct. 18, 2011, the entire disclosures of which are hereby incorporated by reference.

BACKGROUND OF THE INVENTION

The field of the present invention relates to the delivery of energy impulses (and/or fields) to bodily tissues for therapeutic purposes. It relates more specifically to the use of non-invasive devices and methods for transcutaneous electrical nerve stimulation and magnetic nerve stimulation, along with methods of treating medical disorders using energy that is delivered by such devices. The disorders comprise the following urological problems: overactive bladder, urge incontinence, stress incontinence, urge frequency, non-obstructive urinary retention and interstitial cystitis/painful bladder syndrome. In preferred embodiments of the disclosed treatment methods, one or both of the patient's posterior tibial nerves are stimulated transcutaneously near the ankle. An embodiment of the methods selects parameters of the stimulation protocol for each patient, using a model of lower urinary tract function involving coupled nonlinear oscillators.

Treatments for various infirmities sometime require the destruction of otherwise healthy tissue in order to produce a beneficial effect. Malfunctioning tissue is identified and then lesioned or otherwise compromised in order to produce a beneficial outcome, rather than attempting to repair the tissue to its normal functionality. A variety of techniques and mechanisms have been designed to produce focused lesions directly in target nerve tissue, but collateral damage is inevitable.

Other treatments for malfunctioning tissue can be medicinal in nature, but in many cases the patients become dependent upon artificially synthesized chemicals. In many cases, these medicinal approaches have side effects that are either unknown or quite significant. Unfortunately, the beneficial outcomes of surgery and medicines are often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue holds significant promise for the treatment of many ailments, because such stimulation is generally a wholly reversible and non-destructive treatment.

Nerve stimulation is thought to be accomplished directly or indirectly by depolarizing a nerve membrane, causing the discharge of an action potential; or by hyperpolarization of a nerve membrane, preventing the discharge of an action potential. Such stimulation may occur after electrical energy, or also other forms of energy, are transmitted to the vicinity of a nerve [F. RATTAY. The basic mechanism for the electrical stimulation of the nervous system. Neuroscience 89 (2, 1999):335-346; Thomas HEIMBURG and Andrew D. Jackson. On soliton propagation in biomembranes and nerves. PNAS 102 (28, 2005): 9790-9795]. Nerve stimulation may be measured directly as an increase, decrease, or modulation of the activity of nerve fibers, or it may be inferred from the physiological effects that follow the transmission of energy to the nerve fibers.

One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference).

Another application of electrical stimulation of nerves has been the treatment of radiating pain in the lower extremities by stimulating the sacral nerve roots at the bottom of the spinal cord (see U.S. Pat. No. 6,871,099 to WHITEHURST, et al., the disclosure of which is incorporated herein by reference).

Many such therapeutic applications of electrical stimulation involve the surgical implantation of electrodes within a patient. In contrast, for embodiments of the present invention, the disclosed devices and medical procedures stimulate nerves by transmitting energy to nerves and tissue non-invasively. They may offer the patient an alternative that does not involve surgery. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that invasive procedures do involve inserting a substance or device into or through the skin or into an internal body cavity beyond a body orifice. For example, transcutaneous electrical nerve stimulation (TENS) is non-invasive because it involves attaching electrodes to the surface of the skin (or using a form-fitting conductive garment) without breaking the skin. In contrast, percutaneous electrical stimulation of a nerve is minimally invasive because it involves the introduction of an electrode under the skin, via needle-puncture of the skin (see commonly assigned co-pending US Patent Application 2010/0241188, entitled Percutaneous Electrical Treatment of Tissue to ERRICO et al, which is hereby incorporated by reference in its entirety).

Potential advantages of non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures generally present fewer problems with biocompatibility. In cases involving the attachment of electrodes, non-invasive methods have less of a tendency for breakage of leads, and the electrodes can be easily repositioned if necessary. Non-invasive methods are sometimes painless or only minimally painful and may be performed without the need for even local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace, and the cost of non-invasive procedures may be reduced relative to comparable invasive procedures.

Electrodes that are applied non-invasively to the surface of the body have a long history, including electrodes that were used to stimulate underlying nerves [L. A. GEDDES. Historical Evolution of Circuit Models for the Electrode-Electrolyte Interface. Annals of Biomedical Engineering 25 (1997):1-14]. However, electrical stimulation of nerves in general fell into disfavor in middle of the twentieth century, until the "gate theory of pain" was introduced by Melzack and Wall in 1965. This theory, along with advances in electronics, reawakened interest in the use of implanted electrodes to stimulate nerves, initially to control pain. Screening procedures were then developed to determine suitable candidates for electrode implantation, which involved first determining whether the patient responded when stimulated with electrodes applied to the surface of the body in the vicinity of the possible implant. It was subsequently found that the surface stimulation often controlled pain so well that there was no need to implant a stimulating electrode [Charles BURTON and Donald D. Maurer. Pain Suppression by Transcutaneous Electronic Stimulation. IEEE Transactions on Biomedical Engineering BME-21(2, 1974): 81-88].

Non-invasive transcutaneous electrical nerve stimulation (TENS) was then developed for treating different types of pain, including pain in a joint or lower back, cancer pain, post-operative pain, post-traumatic pain, and pain associated with labor and delivery [Steven E. ABRAM. Transcutaneous Electrical Nerve Stimulation. pp 1-10 in: Joel B. Myklebust, ed. Neural stimulation (Volume 2). Boca Raton, Fla. CRC Press 1985; WALSH D M, Lowe A S, McCormack K. Willer J-C, Baxter G D, Allen J M. Transcutaneous electrical nerve stimulation: effect on peripheral nerve conduction, mechanical pain threshold, and tactile threshold in humans. Arch Phys Med Rehabil 79 (1998):1051-1058; J A CAMPBELL. A critical appraisal of the electrical output characteristics of ten transcutaneous nerve stimulators. Clin. phys. Physiol. Meas. 3(2, 1982): 141-150; U.S. Pat. No. 3,817,254, entitled Transcutaneous stimulator and stimulation method, to Maurer; U.S. Pat. No. 4,324,253, entitled Transcutaneous pain control and/or muscle stimulating apparatus, to Greene et al; U.S. Pat. No. 4,503,863, entitled Method and apparatus for transcutaneous electrical stimulation, to Katims; U.S. Pat. No. 5,052,391, entitled High frequency high intensity transcutaneous electrical nerve stimulator and method of treatment, to Silberstone et al; U.S. Pat. No. 6,351,674, entitled Method for inducing electroanesthesia using high frequency, high intensity transcutaneous electrical nerve stimulation, to Silverstone].

As TENS was being developed to treat pain, non-invasive electrical stimulation using surface electrodes was simultaneously developed for additional therapeutic or diagnostic purposes, which are known collectively as electrotherapy. Neuromuscular electrical stimulation (NMES) stimulates normally innervated muscle in an effort to augment strength and endurance of normal (e.g., athletic) or damaged (e.g., spastic) muscle. Functional electrical stimulation (FES) is used to activate nerves innervating muscle affected by paralysis resulting from spinal cord injury, head injury, stroke and other neurological disorders, or muscle affected by foot drop and gait disorders. FES is also used to stimulate muscle as an orthotic substitute, e.g., replace a brace or support in scoliosis management. Another application of surface electrical stimulation is chest-to-back stimulation of tissue, such as emergency defibrillation and cardiac pacing. Surface electrical stimulation has also been used to repair tissue, by increasing circulation through vasodilation, by controlling edema, by healing wounds, and by inducing bone growth. Surface electrical stimulation is also used for iontophoresis, in which electrical currents drive electrically charged drugs or other ions into the skin, usually to treat inflammation and pain, arthritis, wounds or scars.

Stimulation with surface electrodes is also used to evoke a response for diagnostic purposes, for example in peripheral nerve stimulation (PNS) that evaluates the ability of motor and sensory nerves to conduct and produce reflexes. Surface electrical stimulation is also used in electroconvulsive therapy to treat psychiatric disorders; electroanesthesia, for example, to prevent pain from dental procedures; and electrotactile speech processing to convert sound into tactile sensation for the hearing impaired. All of the above-mentioned applications of surface electrode stimulation are intended not to damage the patient, but if higher currents are used with special electrodes, electrosurgery may be performed as a means to cut, coagulate, desiccate, or fulgurate tissue [Mark R. PRAUSNITZ. The effects of electric current applied to skin: A review for transdermal drug delivery. Advanced Drug Delivery Reviews 18 (1996) 395-425].

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body, inducing at a distance an electric field and electric current within electrically-conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006.

Despite its attractiveness, non-invasive electrical stimulation of a nerve is not always possible or practical. This is primarily because the current state of the art may not be able to stimulate a deep nerve selectively or without producing excessive pain, because the stimulation may unintentionally stimulate nerves other than the nerve of interest, including nerves that cause pain. For this reason, forms of electrical stimulation other than TENS may be best suited for the treatment of particular types of pain [Paul F. WHITE, Shitong Li and Jen W. Chiu. Electroanalgesia: Its Role in Acute and Chronic Pain Management. Anesth Analg 92 (2001):505-13]. Accordingly, there remains a long-felt but unsolved need to stimulate nerves totally non-invasively, selectively, and essentially without producing pain.

As compared with what would be experienced by a patient undergoing non-invasive stimulation with conventional TENS or magnetic stimulation methods, an objective of the stimulators disclosed here is to produce relatively little pain for a given depth of stimulus penetration, but nevertheless to stimulate the target nerve to achieve therapeutic results. Or conversely, for a given amount of pain or discomfort on the part of the patient (e.g., the threshold at which such discomfort or pain begins), an objective of the present invention is to achieve a greater depth of penetration or power of the stimulus under the skin. When some nerves are stimulated electrically, they may produce undesirable responses in addition to the therapeutic effect that is intended. For example, the stimulated nerves may produce unwanted muscle twitches. It is therefore another objective of the present invention to selectively produce only the intended therapeutic effect when the target nerve is stimulated by the disclosed devices.

Non-invasive capacitive stimulating electrodes, which contact the patient's skin with a dielectric material, may produce more uniform current densities than electrodes made of electrically conducting material. Their use may therefore be advantageous as a method to avoid potential pain when a patient is electrically stimulated. However, previous capacitive stimulating electrodes have required the use of a high voltage power supply, which is accompanied by the inherent danger of high voltage breakdowns of the electrode's dielectric material [L. A. GEDDES, M. Hinds, and K. S. Foster. Stimulation with capacitor electrodes. Medical and Biological Engineering and Computing 25 (1987): 359-360; Thierry KELLER and Andreas Kuhn. Electrodes for transcutaneous (surface) electrical stimulation. Journal of Automatic Control, University of Belgrade 18(2, 2008):35-45; U.S. Pat. No. 3,077,884, entitled Electro-physiotherapy apparatus, to BARTROW et al, and U.S. Pat. No. 4,144,893, entitled Neuromuscular therapy device, to HICKEY]. Therefore, another objective of one embodiment of the present invention to devise a capacitive stimulating device that does not require the use of a high voltage power supply.

The present invention uses electrical nerve stimulation to treat overactive bladder and urinary incontinence, particularly non-invasive, transcutaneous electrical stimulation of the posterior tibial nerve at a location near the patient's ankle. The storage and voiding of urine are performed by the urinary bladder and urethra, which are muscular structures controlled by the nervous system. Individuals with an overactive bladder exhibit a sudden urge to urinate and a high frequency of urination. They often, but not always, also exhibit urge incontinence that is associated with the leakage of urine due to bladder muscles that contract or spasm inappropriately and/or with dysfunction of urethral sphincters that would normally prevent the passage of urine.

The prevalence of overactive bladder is approximately 11-19% in men and 13-17% in women, which increases with age. In the year 2000, the costs in the United States of urinary incontinence and overactive bladder were estimated to be 19.5 and 12.6 billion dollars, respectively, taking into account costs associated with diagnosis and treatment, as well as consequent costs such as predisposition to urinary tract infections, ulcers, perineal rashes and other skin conditions, infections, falls and broken bones, and premature nursing home admissions. Psychologically, overactive bladder and incontinence are associated with embarrassment, isolation, stigmatization, depression, and the fear of institutionalization [TYAGI 5, Thomas C A, Hayashi Y, Chancellor M B. The overactive bladder: Epidemiology and morbidity. Urol Clin North Am. 33(4, 2006): 433-8; HU T W, Wagner T H, Bentkover J D, Leblanc K, Zhou S Z, Hunt T. Costs of urinary incontinence and overactive bladder in the United States: a comparative study. Urology. 63(3, 2004): 461-465].

Management options for overactive bladder include lifestyle adjustments, bladder retraining, pelvic floor exercises, biofeedback, and pharmacotherapy. Anticholinergic medications are the mainstay of treatment. However, side effects and urinary retention occur in approximately 20% of those who use these medications. In other patients, the medications are ineffective, such that 75% of patients discontinue the use of anticholinergic medications within one year. Major surgical procedures for overactive bladder are considered last resorts, as they potentially lead to serious side effects. Having failed conservative and drug-based therapies for incontinence, some patients resign themselves to a lifetime of containment devices and pads, rather than resort to surgery [Victor W. NITTI and Jerry G. Blaivas. Urinary Incontinence: Epidemiology, Pathophysiology, Evaluation, and Management Overview. Chapter 60 In: Campbell-Walsh Urology, 9th ed., A J Wein, L R Kavoussi, A C Novick, A W Partin and C A Peters, eds. Philadelphia, Pa.: Saunders Elsevier; 2007. pp 2046-2078; LENTZ G M. Urogynecology: physiology of micturition, diagnosis of voiding dysfunction, and incontinence: surgical and nonsurgical treatment. In: Katz V L, Lentz G M, Lobo R A, Gershenson D M, eds. Comprehensive Gynecology. 5th ed. Philadelphia, Pa.: Mosby Elsevier; 2007: chap 21, pp. 537-568].

If pharmacotherapy is unsuccessful and surgery is not being considered, patients with an overactive bladder or incontinence are increasingly treated by neuromodulation [VAN BALKEN M R, Vergunst H, Bemelmans B L. The use of electrical devices for the treatment of bladder dysfunction: a review of methods. J. Urol. 172(3, 2004):846-51; Sandip P. VASAVADA and Raymond R. Rackley. Electrical stimulation for storage and emptying disorders. Chapter 64 in Campbell-Walsh Urology, 9th ed., A J Wein, L R Kavoussi, A C Novick, A W Partin and C A Peters, eds. Philadelphia, Pa.: Saunders Elsevier; 2007. pp 2147-2167; YAMANISHI T, Kama T, Yoshida K I. Neuromodulation for the treatment of urinary incontinence. Int J Urol 15 (2008):665-672]. Sacral nerve electrical stimulation is currently the most common form of neuromodulation that is used to treat overactive bladder and incontinence, which requires an incision and placement of electrodes in the sacrum, in the lower portion of the patient's spine. The procedure is expensive, and problems arise in up to a third of the patients, including change in bowel function, infection, lead movement, pain at implant sites, and/or unpleasant stimulation or sensation.

Percutaneous tibial nerve stimulation (PTNS, also known as posterior tibial nerve stimulation) offers a safer, less invasive treatment alternative for overactive bladder than sacral nerve neuromodulation. Rather than requiring an incision and placement of electrodes in the sacrum, PTNS stimulates sacral nerve roots a location much closer to the surface of the skin, by stimulating the posterior tibial nerve slightly above the ankle. To perform PTNS, a needle is inserted temporarily through the skin to allow introduction of an electrode that will stimulate tibial nerve at that location. However, this procedure may cause problems associated with needle insertion, and because significant training is required in order to perform PTNS, it must ordinarily be performed by professionals in an office setting.

Noninvasive PTNS can also be performed with surface electrodes, wherein the posterior tibial nerve is stimulated transcutaneously. This eliminates potential problems associated with needle insertion and reduces training requirements, such that the patient can sometimes perform the stimulation at home. However, the use of surface electrodes exacerbates the potential for pain from the electrical stimulation itself. This is because transcutaneous PTNS as it is currently performed is unable to stimulate the tibial nerve selectively, potentially causing pain through the stimulation of nearby tissue and other nerves, and because the tibial nerve itself can sense pain if the stimulation waveform is not properly designed. Accordingly, the electrical stimulus power must be limited to what is less than the threshold of pain from surrounding tissue and the tibial nerve itself, which in turn limits the ability of transcutaneous tibial nerve stimulation as it is currently performed to excite portions of the nervous system that may prevent or delay episodes of overactive bladder and urge incontinence. A related selectivity problem is that tibial nerve stimulation will induce movements and contractions of muscle in the toes and foot, such that the electrical stimulus power must also be limited to what is less than the threshold for such movement, thereby limiting the stimulus power that could otherwise be used to treat overactive bladder and urge incontinence.

An objective of the present invention is therefore to devise stimulation devices that are able to deliver higher electrical currents to nerves such as the posterior tibial nerve, selectively and noninvasively, without causing pain, and without inducing muscle movement, through a novel architecture and arrangement of electrodes within the devices, as well as through novel stimulation waveforms. The present invention also discloses a novel magnetic stimulator that may be applied to nerves such as the posterior tibial nerve. The magnetic stimulator has an architecture and stimulation waveforms that share features with the disclosed electrode-based stimulation devices.

Another aspect of the present invention is that it treats overactive bladder, incontinence, and/or related urological disorders through a novel method and mechanism that is based in part upon a particular theory for the origin of overactive bladder and urge incontinence. Currently, the best-known theories are the following four: myogenic, neurogenic, afferent, and integrative or autonomous [Henderson E, Drake M. Overactive bladder. Maturitas. 2010 66(3, 2010): 257-62; En MENG. Recent research advances in the pathophysiology of overactive bladder. Incont Pelvic Floor Dysfunct 3(Suppl 1, 2009): 5-7]. Unlike previous methods of neuromodulation for treating overactive bladder, the presently disclosed methods are based in part upon the integrative or autonomous theory, which attributes bladder muscle instability to abnormal synchronization and imbalanced excitation/inhibition of contractile modules within the bladder, each module of which may contain intramural ganglia and interstitial cells. According to the disclosed methods, the bladder modules may be represented as coupled nonlinear oscillators, leading to a characterization of the dynamics and treatment of the bladder in terms of predictable thresholds that separate different qualitatively different types of bladder dynamics. Implementation of the disclosed methods is intended to aid in evaluating whether an individual is a suitable candidate for the tibial nerve stimulation, in the selection of parameters for the electrical stimulation protocol, and in evaluating the extent to which the stimulation has had an effect.

SUMMARY OF THE INVENTION

In one aspect of the invention, devices and methods are described to produce therapeutic effects in a patient by utilizing an energy source that transmits energy non-invasively to nervous tissue. In particular, the disclosed devices can transmit energy to, or in close proximity to, a posterior tibial nerve near the ankle of the patient, in order to temporarily stimulate, block and/or modulate electrophysiological signals in that nerve. The methods that are disclosed herein comprise stimulating the tibial nerve with particular stimulation waveform parameters, preferably using the nerve stimulator devices that are also described herein.

A novel stimulator device is used to modulate electrical activity of a tibial nerve or other nerves or tissue. The stimulator comprises a source of electrical power and two or more remote electrodes that are configured to stimulate a deep nerve relative to the nerve axis. The device also comprises continuous electrically conducting media with which the electrodes are in contact. The conducting medium is also in contact with an interface element that makes physical contact with the patient's skin. The interface element may be electrically insulating (dielectric) material, such as a sheet of Mylar, in which case electrical coupling of the device to the patient is capacitive. In other embodiments, the interface element is electrically conducting material, such as an electrically conducting or permeable membrane, in which case electrical coupling of the device to the patient is ohmic. The interface element may have a shape that conforms to the contour of a target body surface of a patient when the medium is applied to the target body surface. In another aspect of the invention, a non-invasive magnetic stimulator device is used to modulate electrical activity of the tibial nerve or other nerves or tissue, without actually introducing a magnetic field into the patient.

For the present medical applications, the electrode-based device or a magnetic stimulation device is ordinarily applied to the vicinity of the patient's ankle. In one embodiment of the electrode-based invention, the stimulator comprises two electrodes that lie side-by-side within separate stimulator heads, wherein the electrodes are separated by electrically insulating material. Each electrode is in continuous contact with an electrically conducting medium that extends from the interface element of the stimulator to the electrode. The interface element also contacts the patient's skin when the device is in operation. The conducting media for different electrodes are also separated by electrically insulating material.

In another embodiment of the invention, a non-invasive magnetic stimulator device is ordinarily applied to the vicinity of the patient's ankle. In a preferred embodiment of the magnetic stimulator, the stimulator comprises two toroidal windings that lie side-by-side within separate stimulator heads, wherein the toroidal windings are separated by electrically insulating material. Each toroid is in continuous contact with an electrically conducting medium that extends from the patient's skin to the toroid.

A source of power supplies a pulse of electric charge to the electrodes or magnetic stimulator coil, such that the electrodes or magnetic stimulator produce an electric current and/or an electric field within the patient. The electrical or magnetic stimulator is configured to induce a peak pulse voltage sufficient to produce an electric field in the vicinity of a nerve such as a tibial nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m and an electrical field gradient of greater than 2 V/m/mm.

Current passing through an electrode may be about 0 to 40 mA, with voltage across the electrodes of 0 to 30 volts. The current is passed through the electrodes in bursts of pulses. There may be 1 to 20 pulses per burst, preferably five pulses. Each pulse within a burst has a duration of 20 to 1000 microseconds, preferably 200 microseconds. A burst followed by a silent inter-burst interval repeats at 1 to 5000 bursts per second (bps), preferably at 15-50 bps. The preferred shape of each pulse is a full sinusoidal wave. The preferred stimulator shapes an elongated electric field of effect that can be oriented parallel to a long nerve, such as a tibial nerve in the vicinity of the patient's ankle. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves that produce pain.

The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses as described above, shaping an elongated electrical field of effect as with the electrode-based stimulator.

The disclosure teaches methods for the treatment of urological problems, comprising overactive bladder, urge incontinence, urge frequency, non-obstructive urinary retention and interstitial cystitis/painful bladder syndrome. Teachings of the present invention demonstrate how to treat those conditions in a patient, by positioning the disclosed noninvasive stimulator devices against body surfaces, particularly at a location in the vicinity of the patient's ankle, where a posterior tibial nerve is located under the skin. The teachings also describe the production of beneficial, therapeutic effects in the patient following electrical stimulation at that location. In other embodiments, nerves that may be stimulated noninvasively comprise the pudendal nerve, sciatic nerve, superior gluteal nerve, lumbo-sacral trunk, inferior gluteal nerve, common fibular nerve, posterior femoral cutaneous nerve, obturator nerve, common peroneal nerve, plantar nerve, sacral nerves S1, S2, S3, or S4, or nerves of the S1, S2, S3, or S4 dermatome, and sacral anterior root nerves. The invention also contemplates sites of stimulation that comprise: urethral sphincter and pelvic floor muscles, the suprapubic area, rectum or anus, vagina or clitoris, penis, perineum, thigh, and foot.

The stimulation is performed with a sinusoidal burst waveform as described above, followed by silent inter-burst period repeats itself with a period of T. For example, the sinusoidal period τ may be 200 microseconds; the number of pulses per burst may be N=5; and the whole pattern of burst followed by silent inter-burst period may have a period of T=40000 microseconds, which is comparable to 25 Hz stimulation.

More generally, there may be 1 to 20 pulses per burst, preferably five pulses. Each pulse within a burst has a duration of 20 to 1000 microseconds, preferably 200 microseconds. A burst followed by a silent inter-burst interval repeats at 1 to 5000 bursts per second (bps), preferably at 5 to 50 bps, more preferably 10 to 25 bps stimulation (comparable to 10-25 Hz), and even more preferably at 20 bps. Although the preferred shape of each pulse is a full sinusoidal wave, triangular or other shapes known in the art may be used as well. The stimulation is performed typically for 30 minutes and the treatment is performed once a week for 12 weeks or longer. Treatment may be performed on the posterior tibial nerve near either or both ankles, and it may be performed alternately on the tibial nerves in the left and right legs.

Parameters of the stimulation protocol may be modified or varied to accommodate heterogeneous patient pathophysiology, so as to obtain a beneficial response without the sensation of pain, as indicated for example, by the patient experiencing on average fewer daily urinary voids, and/or fewer daily episodes of urge incontinence, and/or fewer urinary voids per night, and/or increased urinary volumes per void, and/or improved patient emotional well-being.

The individualized selection of parameters for the stimulation protocol may also be based on methods that are disclosed in connection with the description of the bladder wall as a set of semi-autonomous modules that may be described as coupled nonlinear oscillators. In brief, the bladder is described by a set of Coupled non-linear differential equations corresponding to coupled nonlinear oscillators (e.g., Van der Pol oscillators); preliminary measurements before and after tibial nerve stimulation, concerning the patient's bladder and urethra function, are made on individual segments of the patient's bladder, or ambulatory urodynamic measurements are made, or detailed logging of the patient's urinary tract sensations are recorded with the aid of an electronic diary and non-invasive bladder volume measurement; parameters of the equations are estimated using the measurements; many potential treatment protocols are simulated by numerically solving the differential equations, including treatments that vary stimulation parameters and that may preferentially stimulate the patient in different phases of bladder filling; and a treatment protocol is selected among the simulations to minimize unwanted bladder contractions or otherwise be predicted to be therapeutically beneficial.

However, it should be understood that application of the methods and devices is not limited to the examples that are given. The novel systems, devices and methods for treating conditions using the disclosed stimulator or other non-invasive stimulation devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 1 is a schematic view of magnetic and electrode-based nerve or tissue modulating devices according to the present invention, which supply controlled pulses of electrical current to magnetic coils or to electrodes, respectively, each of which are continuously in contact with a volume filled with electrically conducting material, and wherein the conducting material is also in contact with an interface element that, in operation, contacts the patient's skin.

FIG. 2 illustrates an exemplary electrical voltage/current profile for a blocking and/or modulating impulses that are applied to a portion or portions of a nerve, in accordance with an embodiment of the present invention.

FIG. 7 illustrates nerves that are seen from a lower posterior view of an individual, including nerves derived from axons from the lower lumbar (L) and sacral (S) spine nerve roots, the sciatic nerve and its branches (the common peroneal nerve and tibial nerve), as well as a branch of the tibial nerve (the posterior tibial nerve).

DETAILED DESCRIPTION OF THE PREFERRED EMBODIMENTS

Figure 3A:
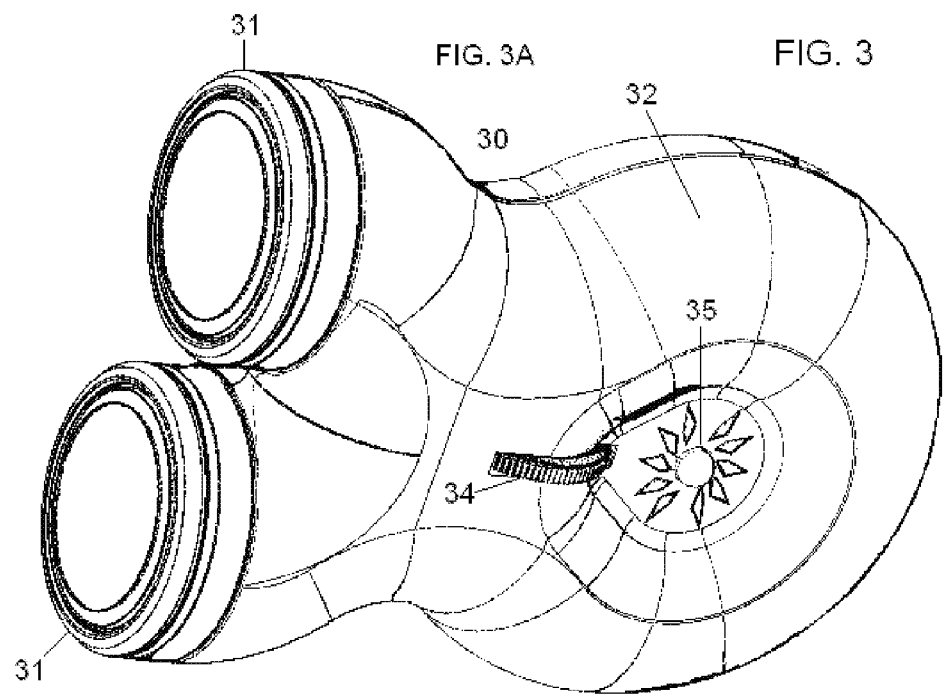
FIG. 3 illustrates a dual-electrode stimulator according to an embodiment of the present invention, which is shown to house the stimulator's electrodes and electronic components.

In the present invention, energy is transmitted non-invasively to a patient using novel electrode-based and/or magnetic stimulation devices that are designed to meet a long-felt but unsolved need to stimulate nerves electrically, totally non-invasively, selectively, and essentially without producing pain.
The invention is particularly useful for producing applied electrical impulses that interact with the signals of one or more nerves to achieve a therapeutic result. In particular, the present disclosure describes devices and methods to stimulate a posterior tibial nerve non-invasively at a location in the vicinity of a patient's ankle, in order to treat disorders of the lower urinary tract.

Transcutaneous electrical stimulation with electrodes, as well as with magnetic stimulators, can be unpleasant or painful, in the experience of patients that undergo such procedures. The quality of sensation caused by stimulation depends strongly on current and frequency, such that currents barely greater than the perception threshold generally cause painless sensations described as tingle, itch, vibration, buzz, touch, pressure, or pinch, but higher currents can cause sharp or burning pain. As the depth of penetration of the stimulus under the skin is increased, any pain will generally begin or increase. Strategies to reduce the pain include: use of anesthetics placed on or injected into the skin near the stimulation and placement of foam pads on the skin at the site of stimulation [Jeffrey J. BORCKARDT, Arthur R. Smith, Kelby Hutcheson, Kevin Johnson, Ziad Nahas, Berry Anderson, M. Bret Schneider, Scott T. Reeves, and Mark S. George. Reducing Pain and Unpleasantness During Repetitive Transcranial Magnetic Stimulation. Journal of ECT 2006; 22:259-264], use of nerve blockades [V. HAKKINEN, H. Eskola, A. Yli-Hankala, T. Nurmikko and S. Kolehmainen. Which structures are sensitive to painful transcranial stimulation? Electromyogr. clin. Neurophysiol. 1995, 35:377-383], the use of very short stimulation pulses [V. SUIHKO. Modelling the response of scalp sensory receptors to transcranial electrical stimulation. Med. Biol. Eng. Comput., 2002, 40, 395-401], decreasing current density by increasing electrode size [Kristof VERHOEVEN and J. Gert van Dijk. Decreasing pain in electrical nerve stimulation. Clinical Neurophysiology 117 (2006) 972-978], using a high impedance electrode [N. SHA, L. P. J. Kenney, B. W. Heller, A. T. Barker, D. Howard and W. Wang. The effect of the impedance of a thin hydrogel electrode on sensation during functional electrical stimulation. Medical Engineering & Physics 30 (2008): 739-746] and providing patients with the amount of information that suits their personalities [Anthony DELITTO, Michael J Strube, Arthur D Shulman, Scott D Minor. A Study of Discomfort with Electrical Stimulation. Phys. Ther. 1992; 72:410-424]. U.S. Pat. No. 7,614,996, entitled Reducing discomfort caused by electrical stimulation, to RIEHL discloses the application of a secondary stimulus to counteract what would otherwise be an uncomfortable primary stimulus. Other methods of reducing pain are intended to be used with invasive nerve stimulation [U.S. Pat. No. 7,904,176, entitled Techniques for reducing pain associated with nerve stimulation, to BEN-EZRA et al].

Additional considerations related to pain resulting from the stimulation are as follows. When stimulation is repeated over the course of multiple sessions, patients may adapt to the pain and exhibit progressively less discomfort. Patients may be heterogeneous with respect to their threshold for pain caused by stimulation, including heterogeneity related to gender and age. Electrical properties of an individual's skin vary from day to day and may be affected by cleaning, abrasion, and the application of various electrode gels and pastes. Skin properties may also be affected by the stimulation itself, as a function of the duration of stimulation, the recovery time between stimulation sessions, the transdermal voltage, the current density, and the power density. The application of multiple electrical pulses can result in different perception or pain thresholds and levels of sensation, depending on the spacing and rate at which pulses are applied. The separation distance between two electrodes determines whether sensations from the electrodes are separate, overlap, or merge. The limit for tolerable sensation is sometimes said to correspond to a current density of 0.5 mA/cm$^2$, but in reality the functional relationship between pain and current density is very complicated. Maximum local current density may be more important in producing pain than average current density, and local current density generally varies under an electrode, e.g., with greater current densities along edges of the electrode or at "hot spots." Furthermore, pain thresholds can have a thermal and/or electrochemical component, as well as a current density component. Pulse frequency plays a significant role in the perception of pain, with muscle contraction being involved at some frequencies and not others, and with the spatial extent of the pain sensation also being a function of frequency. The sensation is also a function of the waveform (square-wave, sinusoidal, trapezoidal, etc.), especially if pulses are less than a millisecond in duration [Mark R. PRAUSNITZ. The effects of electric current applied to skin: A review for transdermal drug delivery. Advanced Drug Delivery Reviews 18 (1996): 395-425].

Considering that there are so many variables that may influence the likelihood of pain during non-invasive electrical stimulation (detailed stimulus waveform, frequency, current density, electrode type and geometry, skin preparation, etc.), considering that these same variables must be simultaneously selected in order to independently produce a desired therapeutic outcome by nerve stimulation, and considering that one also wishes to selectively stimulate the nerve (e.g., avoid stimulating a nearby nerve), it is understandable that prior to the present disclosure, no one has described devices and methods for stimulating a nerve electrically, totally non-invasively, selectively, and without causing substantial pain.

Applicant discovered the disclosed electrode-based devices and methods in the course of experimentation with a magnetic stimulation device that was disclosed in Applicant's commonly assigned co-pending U.S. patent application Ser. No. 12/964,050 entitled Magnetic Stimulation Devices and Methods of Therapy, to SIMON et al. That stimulator used a magnetic coil, embedded in a safe and practical conducting medium that was in direct contact with arbitrarily-oriented patient's skin, which had not been described in its closest art [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999. (UMI Microform Number: 9940153, UMI Company, Ann Arbor Mich.)]. Existing magnetic stimulators are complex and expensive, use high currents that overheat and limit the possible duration of stimulation, and can produce stimulation pain. In contrast to existing magnetic stimulators, the stimulator that was disclosed in Applicant's above-cited co-pending patent application is relatively simple to construct and operates with low currents. Furthermore, the device confines the magnetic field to within the device itself, so that magnetic fields do not enter the patient's body. As a result, this design makes it possible to stimulate the patient's nerve over an extended period of time selectively and without producing pain.

FIG. 1A is a schematic diagram of Applicant's above-mentioned magnetic nerve stimulating/modulating device 301 for delivering impulses of energy to nerves for the treatment of medical conditions. As shown, device 301 may include an impulse generator 310; a power source 320 coupled to the impulse generator 310; a control unit 330 in communication with the impulse generator 310 and coupled to the power source 320; and a magnetic stimulator coil 341 coupled via wires to impulse generator coil 310. The stimulator coil 341 is toroidal in shape, due to its winding around a toroid of core material.

Although the magnetic stimulator coil 341 is shown in FIG. 1A to be a single coil, in practice the coil may also comprise two or more distinct coils, each of which is connected in series or in parallel to the impulse generator 310. Thus, the coil 341 that is shown in FIG. 1A represents all the magnetic stimulator coils of the device collectively. In a preferred embodiment that is discussed in connection with FIG. 5D below, coil 341 actually contains two coils that may be connected either in series or in parallel to the impulse generator 310.

The item labeled in FIG. 1A as 351 is a volume, surrounding the coil 341, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 351 corresponds also to sinuousness or curvature on the surface of the body, against which the conducting medium 351 is applied, so as to make the medium and body surface contiguous. As time-varying electrical current is passed through the coil 341, a magnetic field is produced, but because the coil winding is toroidal, the magnetic field is spatially restricted to the interior of the toroid. An electric field and eddy currents are also produced. The electric field extends beyond the toroidal space and into the patient's body, causing electrical currents and stimulation within the patient. The volume 351 is electrically connected to the patient at a target skin surface in order to significantly reduce the current passed through the coil 341 that is needed to accomplish stimulation of the patient's nerve or tissue. In a preferred embodiment of the magnetic stimulator that is discussed below in connection with FIG. 5D, the conducting medium with which the coil 341 is in contact need not completely surround the toroid.

The design of the magnetic stimulator 301, which is adapted herein for use with surface electrodes, makes it possible to shape the electric field that is used to selectively stimulate a relatively deep nerve such as a tibial nerve in the vicinity of the ankle of a patient. Furthermore, the design produces significantly less pain or discomfort (if any) to a patient than stimulator devices that are currently known in the art. Conversely, for a given amount of pain or discomfort on the part of the patient (e.g., the threshold at which such discomfort or pain begins), the design achieves a greater depth of penetration of the stimulus under the skin.

FIG. 1B is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either the magnetic stimulator 301 or the electrode-based stimulator 302, allowing the user to change parameter settings depending on whether coils 341 or the electrodes 340 are attached.

Although a pair of electrodes 340 is shown in FIG. 1B, in practice the electrodes may also comprise three or more distinct electrode elements, each of which is connected in series or in parallel to the impulse generator 310. Thus, the electrodes 340 that are shown in FIG. 1B represent all electrodes of the device collectively.

The item labeled in FIG. 1B as 350 is a volume, contiguous with an electrode 340, that is filled with electrically conducting medium. As described below in connection with embodiments of the invention, conducting medium in which the electrode 340 is embedded need not completely surround an electrode. As also described below in connection with a preferred embodiment, the volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In a preferred embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the coil 341 or electrodes 340. It is noted that nerve stimulating/modulating device 301 or 302 may be referred to by its function as a pulse generator. Patent application publications US2005/0075701 and US2005/0075702, both to SHAFER, both of which are incorporated herein by reference, relating to stimulation of neurons of the sympathetic nervous system to attenuate an immune response, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard and computer mouse as well as any externally supplied physiological signals, analog-to-digital converters for digitizing externally supplied analog signals, communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes or coils, as well as the spatial distribution of the electric field that is produced by the electrodes or coils. The rise time and peak energy are governed by the electrical characteristics of the stimulator and electrodes or coils, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurto, Przemystaw Plonecki, Jacek Starzyński, Stanistaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

FIG. 2A illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the coil 341 or electrodes 340 that deliver the stimulating, blocking and/or modulating impulse 410 to the nerve. Nerve stimulating/modulating device 301 or 302 may be externally powered and/or recharged may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes or coils, the device disclosed in patent publication No. US2005/0216062 (the entire disclosure of which is incorporated herein by reference) may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables.

Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type the user wishes, who can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 50 Hz, more preferably around 25 Hz. The modulation signal may have a pulse width selected to influence the therapeutic result, such as about 20 microseconds or greater, such as about 20 microseconds to about 1000 microseconds. For example, the electric field induced by the device within tissue in the vicinity of a nerve is 10 to 600 V/m, preferably around 300 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz.

An objective of the disclosed stimulators is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J. Struijk. A comparative study of three techniques for diameter selective fiber activation in the vagal nerve: anodal block, depolarizing prepulses and slowly rising pulses. J. Neural Eng. (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2B and 2C. As seen there, individual sinusoidal pulses have a period $\tau$, and a burst consists of N such pulses. This is followed by a period with no signal (the inter-burst period). The pattern of a burst followed by silent inter-burst period repeats itself with a period of T. For example, the sinusoidal period may be 200 microseconds; the number of pulses per burst may be N=5; and the whole pattern of burst followed by silent inter-burst period may have a period of T=40000 microseconds (a much smaller value of T is shown in FIG. 2C to make the bursts discernable). When these exemplary values are used for T and $\tau$, the waveform contains significant Fourier components at higher frequencies ($\frac{1}{200}$ microseconds=5000/sec), as compared with those contained in transcutaneous nerve stimulation waveforms, as currently practiced.

Applicant is unaware of such a waveform having been used with therapeutic nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters $\tau$, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10 (1989):187-191;

Alex R WARD, Nataliya Shkuratova. Russian Electrical Stimulation The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008):1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2B and 2C may have an $E_{max}$ value of 17 V/m, which is sufficient to stimulate the nerve but is significantly lower than the threshold needed to stimulate surrounding muscle.

In order to compare the electrical stimulator that is disclosed herein with existing electrodes and stimulators used for non-invasive electrical stimulation, it is useful to first summarize the relevant physics of electric fields and currents that are produced by the electrodes. According to Maxwell's equation (Ampere's law with Maxwell correction): $\nabla \times B = J + \in(\partial E/\partial t)$, where B is the magnetic field, J is the electrical current density, E is the electric field, E is the permittivity, and t is time [Richard P. FEYNMAN, Robert B. Leighton, and Matthew Sands. The Feynman Lectures on Physics. Volume Addison-Wesley Publ. Co. (Reading Mass., 1964), page 15-15].

According to Faraday's law, $\nabla \times = -\partial B/\partial t$. However, for present purposes, changes in the magnetic field B may be ignored, so $\nabla \times E = 0$, and E may therefore be obtained from the gradient of a scalar potential $\Phi$: $E = -\nabla \Phi$. In general, the scalar potential $\Phi$ and the electric field E are functions of position (r) and time (t).

The electrical current density J is also a function of position (r) and time (t), and it is determined by the electric field and conductivity as follows, where the conductivity $\sigma$ is generally a tensor and a function of position (r): $J = \sigma E = -\sigma \nabla \Phi$.

Because $\nabla \cdot \nabla \times B = 0$, Ampere's law with Maxwell's correction may be written as: $\nabla \cdot J + \nabla \cdot \in (\partial E/\partial t) = 0$. If the current flows in material that is essentially unpolarizable (i.e., is presumed not to be a dielectric so that $\in = 0$), substitution of the expression for J into the above expression for Ampere's law gives $-\nabla \cdot (\sigma \nabla \Phi) = 0$, which is a form of Laplace's equation. If the conductivity of material in the device (or patient) is itself a function of the electric field or potential, then the equation becomes non-linear, which could exhibit multiple solutions, frequency multiplication, and other such non-linear behavior. The equation has been solved analytically for special electrode configurations, but for more general electrode configurations, it must be solved numerically [Petrus J. CILLIERS. Analysis of the current density distribution due to surface electrode stimulation of the human body. Ph.D. Dissertation, Ohio State University, 1988. (UMI Microform Number: 8820270, UMI Company, Ann Arbor Mich.); Martin REICHEL, Teresa Breyer, Winfried Mayr, and Frank Rattay. Simulation of the Three-Dimensional Electrical Field in the Course of Functional Electrical Stimulation. Artificial Organs 26(3, 2002):252-255; Cameron C. McINTYRE and Warren M. Grill. Finite Element Analysis of the Current-Density and Electric Field Generated by Metal Microelectrodes. Annals of Biomedical Engineering 29 (2001): 227-235; A. PATRICIU, T. P. DeMonte, M. L. G. Joy, J. J. Struijk. Investigation of current densities produced by surface electrodes using finite element modeling and current density imaging. Proceedings of the 23rd Annual EMBS International Conference, Oct. 25-28, 2001, Istanbul, Turkey: 2403-2406; Yong H U, X B Xie, L Y Pang, X H Li KDK Luk. Current Density Distribution Under Surface Electrode on Posterior Tibial Nerve Electrical Stimulation. Proceedings of the 2005 IEEE Engineering in Medicine and Biology 27th Annual Conference Shanghai, China, Sep. 1-4, 2005: 3650-3652].

The equation has also been solved numerically in order to compare different electrode shapes and numbers [Abhishek DATTA, Maged Elwassif, Fortunato Battaglia and Marom Bikson. Transcranial current stimulation focality using disc and ring electrode configurations: FEM analysis. J. Neural Eng. 5 (2008) 163-174; Jay T. RUBENSTEIN, Francis A. Spelman, Mani Soma and Michael F. Suesserman. Current Density Profiles of Surface Mounted and Recessed Electrodes for Neural Prostheses. IEEE Transactions on Biomedical Engineering BME-34 (11, 1987): 864-875; David A. KSIENSKI. A Minimum Profile Uniform Current Density Electrode. IEEE Transactions on Biomedical Engineering 39 (7, 1992): 682-692; Andreas KUHN, Thierry Keller, Silvestro Micera, Manfred Morari. Array electrode design for transcutaneous electrical stimulation: A simulation study. Medical Engineering & Physics 31(2009) 945-951]. The calculated electrical fields may be confirmed using measurements using a phantom [A. M. SAGI_DOLEV, D. Prutchi and R. H. Nathan. Three-dimensional current density distribution under surface stimulation electrodes. Med. and Biol. Eng. and Comput. 33 (1995): 403-408].

If capacitive effects cannot be ignored, an additional term involving the time-derivative of the gradient of the potential appears in the more general expression, as obtained by substituting the expressions for J and E into the divergence of Ampere's law with Maxwell's correction:

$$-\nabla \cdot (\sigma \nabla \Phi) - \nabla \cdot (\in \nabla (\partial \Phi / \partial t)) = 0$$

The permittivity $\in$ is a function of position (r) and is generally a tensor. It may result from properties of the body and may also be a property of the electrode design [L. A. GEDDES, M. Hinds and K. S. Foster. Stimulation with capacitor electrodes. Med. and Biol. Eng. and Comput. 25 (1987):359-360]. As a consequence of such a term, the waveform of the electrical potential at points within the body will generally be altered relative to the waveform of the voltage signal(s) applied to the electrode(s). Furthermore, if the permittivity of a material in the device itself (or patient) is a function of the electric field or potential, then the equation becomes non-linear, which could exhibit multiple solutions, frequency multiplication, and other such non-linear behavior. This time-dependent equation has been solved numerically [KUHN A, Keller T. A 3D transient model for transcutaneous functional electrical stimulation. Proc. 10th Annual Conference of the International FES Society July 2005—Montreal, Canada: pp. 1-3; Andreas KUHN, Thierry Keller, Marc Lawrence, Manfred Morari. A model for transcutaneous current stimulation: simulations and experiments. Med Biol Eng Comput 47 (2009):279-289; N. FILIPOVIC, M. Nedeljkovic, A. Peulic. Finite Element Modeling of a Transient Functional Electrical Stimulation. Journal of the Serbian Society for Computational Mechanics 1(1, 2007):154-163; Todd A. KUIKEN, Nikolay S. Stoykov, Milica Popovic, Madeleine Lowery and Allen Taflove. Finite Element Modeling of Electromagnetic Signal Propagation in a Phantom Arm. IEEE Transactions on Neural Systems and Rehabilitation Engineering 9 (4, 2001): 346-354].

In any case, Dirichlet (D) boundary conditions define voltage sources, and Neumann (N) boundary conditions describe the behavior of the electric field at the crossover boundary from skin to air, as follows:

$$N: \partial \Phi / \partial n = \sigma(r) \text{ and } D: \Phi = V(t)$$

where n denotes the outward pointing normal vector, i.e., the vector orthogonal to the boundary curve; and V(t) denotes the voltage applied to an electrode. Thus, no conduction current can flow across an air/conductor interface, so according to the interfacial boundary conditions, the component of any current normal to the an air/conductor interface must be zero. In constructing the above differential equation for Φ as a function of time, the divergence of J is taken, which satisfies the continuity equation: $\nabla \cdot J = -\partial \rho / \partial t$, where ρ is the charge density. Conservation of charge requires that sides of this equation equal zero everywhere except at the surface of the electrode where charge is impressed upon the system (injected or received).

It is an objective of the present invention to shape an elongated electric field of effect that can be oriented parallel to a long nerve such as the tibial nerve in the vicinity of the patient' ankle. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which current flow is restricted. Shaping of the electric field refers both to the circumscribing of regions within which there is a significant electric field and to configuring the directions of the electric field within those regions. Our invention does so by configuring elements that are present within the equations that were summarized above, comprising (but not limited to) the following exemplary configurations that may be used alone or in combination.

First, different contours or shapes of the electrodes affect $\nabla \cdot J$. For example, charge is impressed upon the system (injected or received) differently if an electrode is curved versus flat, or if there are more than two electrodes in the system.

Second, values of the voltage V(t) in the above boundary condition is manipulated to shape the electric field. For example, if the device contains two pairs of electrodes that are perpendicular or at a variable angle with respect to one another, the waveform of the voltage across one pair of electrodes may be different than the waveform of the voltage across the second pair, so that the superimposed electric fields that they produce may exhibit beat frequencies, as has been attempted with electrode-based stimulators [U.S. Pat. No. 5,512,057, entitled Interferential stimulator for applying localized stimulation, to REISS et al.], and acoustic stimulators [U.S. Pat. No. 5,903,516, entitled Acoustic force generator for detection, imaging and information transmission using the beat signal of multiple intersecting sonic beams, to GREENLEAF et al].

Third, the scalar potential Φ in the above equation $\partial \Phi / \partial n = \sigma(r)$ may be manipulated to shape the electric field. For example, this is accomplished by changing the boundaries of conductor/air (or non-conductor) interfaces, thereby creating different boundary conditions. For example, the conducting material may pass through conducting apertures in an insulated mesh before contacting the patient's skin, creating thereby an array of electric field maxima. As another example, an electrode may be disposed at the end of a long tube that is filled with conducting material, or the electrode may be situated at the bottom of a curved cup that is filled with conducting material. In those cases the dimensions of the tube or cup would affect the resulting electric fields and currents.

Fourth, the conductivity a (in the equation J=σE) may be varied spatially within the device by using two or more different conducting materials that are in contact with one another, for given boundary conditions. The conductivity may also be varied by constructing some conducting material from a semiconductor, which allows for adjustment of the conductivity in space and in time by exposure of the semiconductor to agents to which they are sensitive, such as electric fields, light at particular wavelengths, temperature, or some other environmental variable over which the user of the device has control. For the special case in which the semiconductor's conductivity may be made to approach zero, that would approximate the imposition of an interfacial boundary condition as described in the previous paragraph.

Fifth, a dielectric material having a high permittivity ∈, such as Mylar, neoprene, titanium dioxide, or strontium titanate, may be used in the device, for example, in order to permit capacitative electrical coupling to the patient's skin. Changing the permittivity in conjunction along with changing the waveform V(t) would especially affect operation of the device, because the permittivity appears in a term that is a function of the time-derivative of the electric potential: $\nabla \cdot (\in \nabla (\partial \Phi / \partial t))$.

In configurations of the present invention, an electrode is situated in a container that is filled with conducting material. The disclosure below applies as well to conducting material within the magnetic stimulation device. In one embodiment, the container contains holes so that the conducting material (e.g., a conducting gel) can make physical contact with the patient's skin through the holes. For example, the conducting medium 351 in FIG. 1A or 350 in FIG. 1B may comprise a chamber surrounding the electrode, filled with a conductive gel that has the approximate viscosity and mechanical consistency of gel deodorant (e.g., Right Guard Clear Gel from Dial Corporation, 15501N. Dial Boulevard, Scottsdale Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue.

Agar can also be used as part of the conducting medium, but it is not preferred, because agar degrades in time, is not ideal to use against skin, and presents difficulties with cleaning the patient. Rather than using agar as the conducting medium, an electrode can instead be in contact with in a conducting solution such as 1-10% NaCl that also contacts an electrically conducting interface to the human tissue. Such an interface is useful as it allows current to flow from the electrode into the tissue and supports the conducting medium, wherein the device can be completely sealed. Thus, the interface is material, interposed between the conducting medium and patient's skin, that allows the conducting medium (e.g., saline solution) to slowly leak through it, allowing current to flow to the skin. Several interfaces (351 in FIG. 1) are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J. Martens. Conducting polymer-hydrogels for medical electrode applications. Sci. Technol. Adv. Mater. 11 (2010) 014107 (13 pp)]. For example it may be the following hypoallergenic, bacteriostatic electrode gel: SIG-NAGEL Electrode Gel from Parker Laboratories, Inc., 286 Eldridge Rd., Fairfield N.J. 07004. Another example is the KM10T hydrogel from Katecho Inc., 4020 Gannett Ave., Des Moines Iowa 50321.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the electrode and conducting solution in from the tissue, yet allow current to pass.

The electrode-base based stimulator in FIG. 1B shows two equivalent electrodes 340, side-by-side, wherein electrical current would pass through the two electrodes in opposite directions. Thus, the current will flow from one electrode, through the tissue and back through the other electrode, completing the circuit within the electrodes' conducting media that are separated from one another. An advantage of using two equivalent electrodes in this configuration is that this design will increase the magnitude of the electric field gradient between them, which is crucial for exciting long, straight axons such as the tibial nerve in the vicinity of the patient's ankle and other deep peripheral nerves.

Figure 3B:
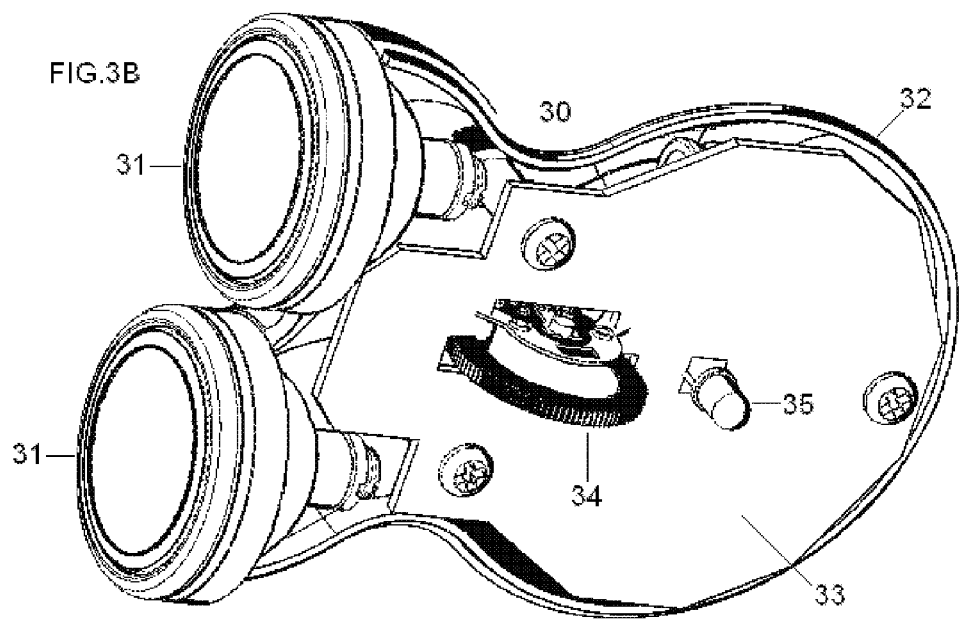

A preferred embodiment of the electrode-based stimulator is shown in FIG. 3A. A cross-sectional view of the stimulator along its long axis is shown in FIG. 3B. As shown, the stimulator (30) comprises two heads (31) and a body (32) that joins them. Each head (31) contains a stimulating electrode. The body of the stimulator (32) contains the electronic components and battery (not shown) that are used to generate the signals that drive the electrodes, which are located behind the insulating board (33) that is shown in FIG. 3B. However, in other embodiments of the invention, the electronic components that generate the signals that are applied to the electrodes may be separate, but connected to the electrode head (31) using wires. Furthermore, other embodiments of the invention may contain a single such head or more than two heads.

Heads of the stimulator (31) are applied to a surface of the patient's body, during which time the stimulator may be held in place by straps or frames (not shown), or the stimulator may be held against the patient's body by hand. In either case, the level of stimulation power may be adjusted with a wheel (34) that also serves as an on/off switch. A light (35) is illuminated when power is being supplied to the stimulator. An optional cap may be provided to cover each of the stimulator heads (31), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate.

Construction of different embodiments of the stimulator head is shown in more detail in FIG. 4. Referring now to the exploded view shown in FIG. 4A, the electrode head is assembled from a snap-on cap (41) that serves as a tambour for a dielectric or conducting membrane (42), a disc without fenestration (43) or alternatively with fenestration (43'), the head-cup (44), and the electrode which is also a screw (45). Two embodiments of the disc (43) are shown. The preferred embodiment (43) is a solid, ordinarily uniformly conducting disc (e.g., metal such as stainless steel), which is possibly flexible in some embodiments. An alternate embodiment of the disc (43') is also shown, which is a non-conducting (e.g., plastic) aperture screen that permits electrical current to pass through its apertures. The electrode (45, also 340 in FIG. 1) seen in each stimulator head has the shape of a screw that is flattened on its tip. Pointing of the tip would make the electrode more of a point source, such that the above-mentioned equations for the electrical potential may have a solution corresponding more closely to a far-field approximation. Rounding of the electrode surface or making the surface with another shape will likewise affect the boundary conditions. Completed assembly of the stimulator head is shown in FIG. 4B, which also shows how the head is attached to the body of the stimulator (47).

The membrane (42) ordinarily serves as the interface shown as 351 in FIG. 1. For example, the membrane (42) may be made of a dielectric (non-conducting) material, such as a thin sheet of Mylar (biaxially-oriented polyethylene terephthalate, also known as BoPET). In other embodiments, it may be made of conducting material, such as a sheet of Tecophlic material from Lubrizol Corporation, 29400 Lakeland Boulevard, Wickliffe, Ohio 44092. In one embodiment shown in FIG. 4A, apertures of the alternate disc (43') may be open, or they may be plugged with conducting material, for example, KM10T hydrogel from Katecho Inc., 4020 Gannett Ave., Des Moines Iowa 50321. If the apertures are so-plugged, and the membrane (42) is made of conducting material, the membrane becomes optional, and the plug serves as the interface 351 shown in FIG. 1.

The head-cup (44) is filled with conducting material (350 in FIG. 1), for example, SIGNAGEL Electrode Gel from Parker Laboratories, Inc., 286 Eldridge Rd., Fairfield N.J. 07004. The snap-on cap (41), aperture screen disc (43'), head-cup (44) and body of the stimulator are made of a non-conducting material, such as acrylonitrile butadiene styrene. The depth of the head-cup from its top surface to the electrode may be between one and six centimeters. The head-cup may have a different curvature than what is shown in FIG. 4, or it may be tubular or conical or have some other inner surface geometry that will affect the Neumann boundary conditions.

The alternate embodiment of the stimulator head that is shown in FIG. 4C also contains a snap-on cap (41), membrane (42) that is made of a dielectric or a conducting material, the head-cup (44), and the electrode which is also a screw (45).

Figure 4A:
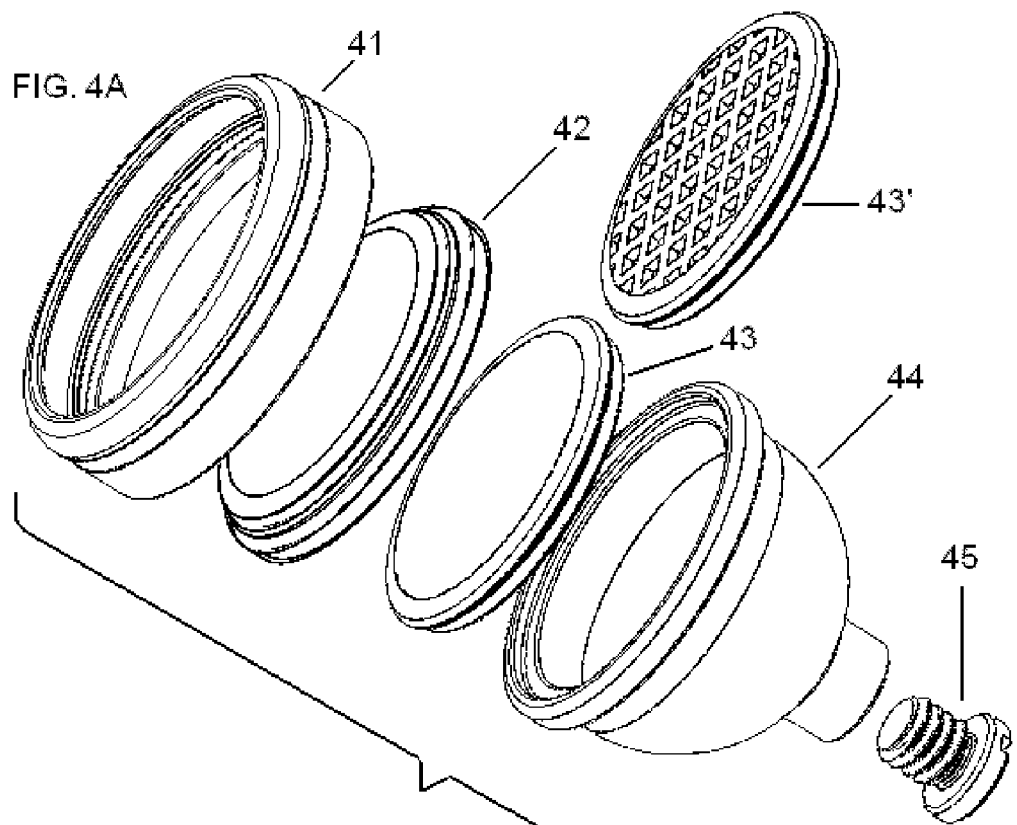
FIG. 4 illustrates preferred and alternate embodiments of the head of the dual-electrode stimulator that is shown in FIG. 3.
Figure 4B:
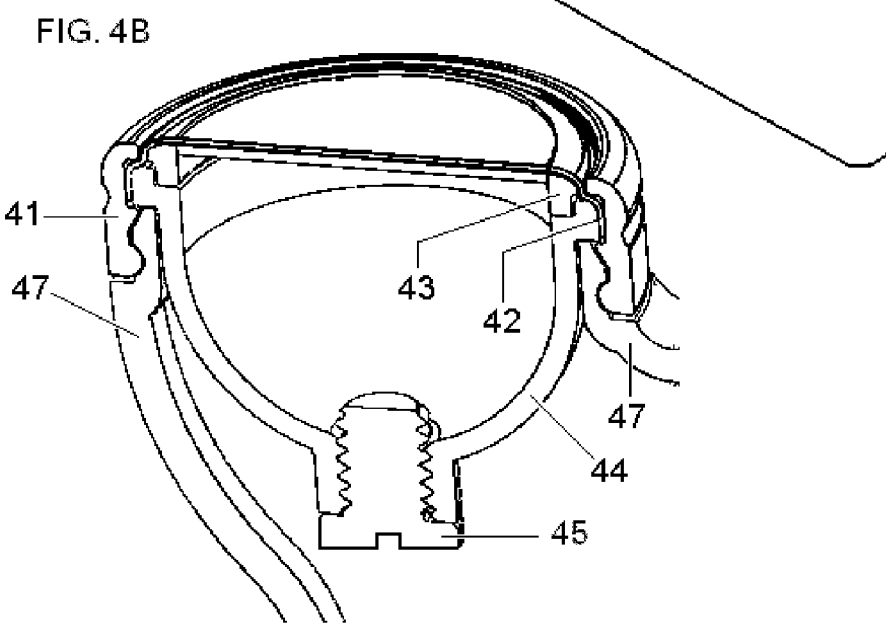

This alternate embodiment differs from the embodiment shown in FIGS. 4A and 4B in regard to the mechanical support that is provided to the membrane (42). Whereas the disc (43) or (43') had provided mechanical support to the membrane in the other embodiment, in the alternate embodiment a reinforcing ring (40) is provided to the membrane. That reinforcement ring rests on non-conducting struts (49) that are placed in the head-cup (44), and a non-conducting strut-ring (48) is placed within notches in the struts (49) to hold the struts in place. An advantage of the alternate embodiment is that without a disc (43) or (43'), current flow may be less restricted through the membrane (42), especially if the membrane is made of a conducting material. Furthermore, although the struts and strut-ring are made of non-conducting material in this alternate embodiment, the design may be adapted to position additional electrode or other conducting elements within the head-cup for other more specialized configurations of the stimulator head, the inclusion of which will influence the electric fields that are generated by the device. Completed assembly of the alternate stimulator head is shown in FIG. 4D, without showing its attachment to the body of the stimulator. In fact, it is possible to insert a lead under the head of the electrode (45), and many other methods of attaching the electrode to the signal-generating electronics of the stimulator are known in the art.

Figure 4E:
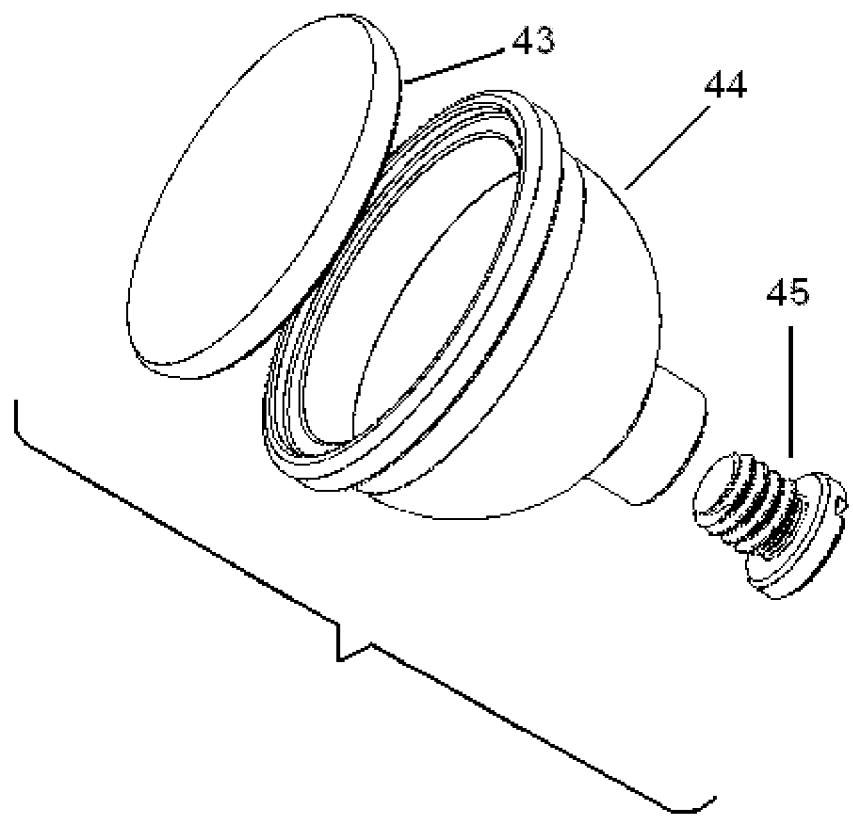
Figure 4F:
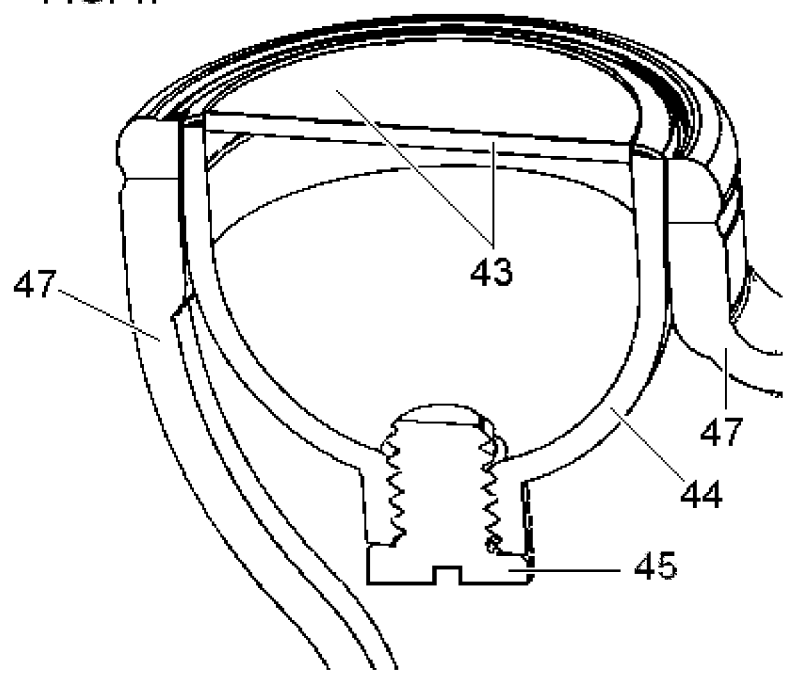

If the membrane (42) is made of conducting materials, and the disc (43) in FIG. 4A is made of solid conducting materials such as stainless steel, the membrane becomes optional, and the disc serves as the interface 351 shown in FIG. 1. Thus, an embodiment without the membrane is shown in FIGS. 4E and 4F. FIG. 4E shows that this version of the device comprises a solid (but possibly flexible in some embodiments) conducting disc that cannot absorb fluid (43), the non-conducting stimulator head (44) into or onto which the disc is placed, and the electrode (45), which is also a screw. It is understood that the disc (43) may have an anisotropic material or electrical structure, for example, wherein a disc of stainless steel has a grain, such that the grain of the disc should be rotated about its location on the stimulator head, in order to achieve optimal electrical stimulation of the patient. As seen in FIG. 4F, these items are assembled to become a sealed stimulator head that is attached to the body of the stimulator (47). The disc (43) may screw into the stimulator head (44), it may be attached to the head with adhesive, or it may be attached by other methods that are known in the art. The chamber of the stimulator head-cup is filled with a conducting gel, fluid, or paste, and because the disc (43) and electrode (45) are tightly sealed against the stimulator head-cup (44), the conducting material within the stimulator head cannot leak out.

In some embodiments, the interface and/or its underlying mechanical support comprise materials that will also provide a substantial or complete seal of the interior of the device. This inhibits any leakage of conducting material, such as gel, from the interior of the device and also inhibits any fluids from entering the device. In addition, this feature allows the user to easily clean the outer surface of the device (e.g., with isopropyl alcohol or similar disinfectant), avoiding potential contamination during subsequent uses of the device.

In some embodiments, the interface comprises a fluid permeable material that allows for passage of current through the permeable portions of the material. In these embodiments, a conductive medium (such as a gel) is preferably situated between the electrode(s) and the permeable interface: The conductive medium provides a conductive pathway for electrons to pass through the permeable interface to the outer surface of the interface and to the patient's skin.

In other embodiments of the present invention, the interface (351 in FIG. 1, or 42 in FIG. 4) is made from a very thin material with a high dielectric constant, such as material used to make capacitors. For example, it may be Mylar having a submicron thickness (preferably in the range 0.5 to 1.5 microns) having a dielectric constant of about 3. Because one side of Mylar is slick, and the other side is microscopically rough, the present invention contemplates two different configurations: one in which the slick side is oriented towards the patient's skin, and the other in which the rough side is so-oriented. Thus, at stimulation Fourier frequencies of several kilohertz or greater, the dielectric interface will capacitively couple the signal through itself, because it will have an impedance comparable to that of the skin. Thus, the dielectric interface will isolate the stimulator's electrode from the tissue, yet allow current to pass. In a preferred embodiment of the present invention, non-invasive electrical stimulation of a nerve is accomplished essentially substantially capacitively, which reduces the amount of ohmic stimulation, thereby reducing the sensation the patient feels on the tissue surface. This would correspond to a situation, for example, in which at least 30%, preferably at least 50%, of the energy stimulating the nerve comes from capacitive coupling through the stimulator interface, rather than from ohmic coupling. In other words, a substantial portion (e.g., 50%) of the voltage drop is across the dielectric interface, while the remaining portion is through the tissue.

The selection of the material for the dielectric constant involves at least two important variables: (1) the thickness of the interface; and (2) the dielectric constant of the material. The thinner the interface and/or the higher the dielectric constant of the material, the lower the voltage drop across the dielectric interface (and thus the lower the driving voltage required). For example, with Mylar, the thickness could be about 0.5 to 5 microns (preferably about 1 micron) with a dielectric constant of about 3. For a piezoelectric material like barium titanate or PZT (lead zirconate titanate), the thickness could be about 100-400 microns (preferably about 200 microns or 0.2 mm) because the dielectric constant is >1000.

One of the novelties of the embodiment that is a non-invasive capacitive stimulator (hereinafter referred to more generally as a capacitive electrode) arises in that it uses a low voltage (generally less than 100 volt) power source, which is made possible by the use of a suitable stimulation waveform, such as the waveform that is disclosed herein (FIGS. 2B and 2C). In addition, the capacitive electrode allows for the use of an interface that provides a more adequate seal of the interior of the device. The capacitive electrode may be used by applying a small amount of conductive material (e.g., conductive gel as described above) to its outer surface. In some embodiments, it may also be used by contacting dry skin, thereby avoiding the inconvenience of applying an electrode gel, paste, or other electrolytic material to the patient's skin and avoiding the problems associated with the drying of electrode pastes and gels. Such a dry electrode would be particularly suitable for use with a patient who exhibits dermatitis after the electrode gel is placed in contact with the skin [Ralph J. COSKEY. Contact dermatitis caused by ECG electrode jelly. Arch Dermatol 113 (1977): 839-840]. The capacitive electrode may also be used to contact skin that has been wetted (e.g., with tap water or a more conventional electrolyte material) to make the electrode-skin contact (here the dielectric constant) more uniform [A L ALEXELONESCU, G Barbero, F C M Freire, and R Merletti. Effect of composition on the dielectric properties of hydrogels for biomedical applications. Physiol. Meas. 31(2010) S169-S182].

As described below, capacitive biomedical electrodes are known in the art, but when used to stimulate a nerve noninvasively, a high voltage power supply is currently used to perform the stimulation. Otherwise, prior use of capacitive biomedical electrodes has been limited to invasive, implanted applications; to non-invasive applications that involve monitoring or recording of a signal, but not stimulation of tissue; to non-invasive applications that involve the stimulation of something other than a nerve (e.g., tumor); or as the dispersive electrode in electrosurgery.

Evidence of a long-felt but unsolved need, and evidence of failure of others to solve the problem that is solved by the this embodiment of the present invention (low-voltage, non-invasive capacitive stimulation of a nerve), is provided by KELLER and Kuhn, who review the previous high-voltage capacitive stimulating electrode of GEDDES et al and write that "Capacitive stimulation would be a preferred way of activating muscle nerves and fibers, when the inherent danger of high voltage breakdowns of the dielectric material can be eliminated. Goal of future research could be the development of improved and ultra-thin dielectric foils, such that the high stimulation voltage can be lowered." [L. A. GEDDES, M. Hinds, and K. S. Foster. Stimulation with capacitor electrodes. Medical and Biological Engineering and Computing 25 (1987): 359-360; Thierry KELLER and Andreas Kuhn. Electrodes for transcutaneous (surface) electrical stimulation. Journal of Automatic Control, University of Belgrade 18(2, 2008):35-45, on page 39]. It is understood that in the United States, according to the 2005 National Electrical Code, high voltage is any voltage over 600 volts. U.S. Pat. No. 3,077,884, entitled Electro-physiotherapy apparatus, to BARTROW et al, U.S. Pat. No. 4,144,893, entitled Neuromuscular therapy device, to HICKEY and U.S. Pat. No. 7,933,648, entitled High voltage transcutaneous electrical stimulation device and method, to TANRISEVER, also describe high voltage capacitive stimulation electrodes. U.S. Pat. No. 7,904,180, entitled Capacitive medical electrode, to JUOLA et al, describes a capacitive electrode that includes transcutaneous nerve stimulation as one intended application, but that patent does not describe stimulation voltages or stimulation waveforms and frequencies that are to be used for the transcutaneous stimulation. U.S. Pat. No. 7,715,921, entitled Electrodes for applying an electric field in-vivo over an extended period of time, to PALTI, and U.S. Pat. No. 7,805,201, entitled Treating a tumor or the like with an electric field, to PALTI, also describe capacitive stimulation electrodes, but they are intended for the treatment of tumors, do not disclose uses involving nerves, and teach stimulation frequencies in the range of 50 kHz to about 500 kHz.

This embodiment of the present invention uses a different method to lower the high stimulation voltage than developing ultra-thin dielectric foils, namely, to use a suitable stimulation waveform, such as the waveform that is disclosed herein (FIGS. 2B and 2C). That waveform has significant Fourier components at higher frequencies than waveforms used for transcutaneous nerve stimulation as currently practiced. Thus, one of ordinary skill in the art would not have combined the claimed elements, because transcutaneous nerve stimulation is performed with waveforms having significant Fourier components only at lower frequencies, and noninvasive capacitive nerve stimulation is performed at higher voltages. In fact, the elements in combination do not merely perform the function that each element performs separately. The dielectric material alone may be placed in contact with the skin in order to perform pasteless or dry stimulation, with a more uniform current density than is associated with ohmic stimulation, albeit with high stimulation voltages [L. A. GEDDES, M. Hinds, and K. S. Foster. Stimulation with capacitor electrodes. Medical and Biological Engineering and Computing 25 (1987): 359-360; Yongmin KIM, H. Gunter Zieber, and Frank A. Yang. Uniformity of current density under stimulating electrodes. Critical Reviews in Biomedical Engineering 17(1990, 6): 585-619]. With regard to the waveform element, a waveform that has significant Fourier components at higher frequencies than waveforms currently used for transcutaneous nerve stimulation may be used to selectively stimulate a deep nerve and avoid stimulating other nerves, as disclosed herein for both noncapacitive and capacitive electrodes. But it is the combination of the two elements (dielectric interface and waveform) that makes it possible to stimulate a nerve capacitively without using the high stimulation voltage as is currently practiced.

Another embodiment of the electrode-based stimulator is shown in FIG. 5, showing a device in which electrically conducting material is dispensed from the device to the patient's skin. In this embodiment, the interface (351 in FIG. 1) is the conducting material itself. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

Figure 5A:
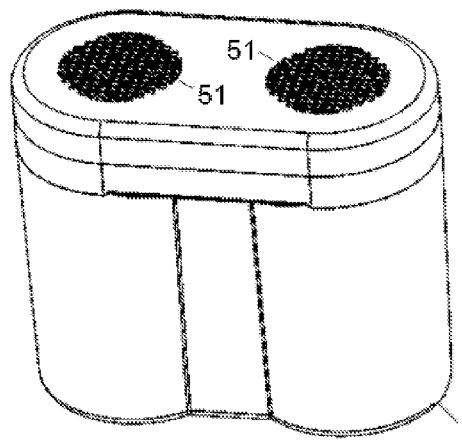
FIG. 5 illustrates an alternate embodiment of the dual-electrode stimulator, also comparing it with an embodiment of the magnetic stimulator according to the present invention.
Figure 5B:
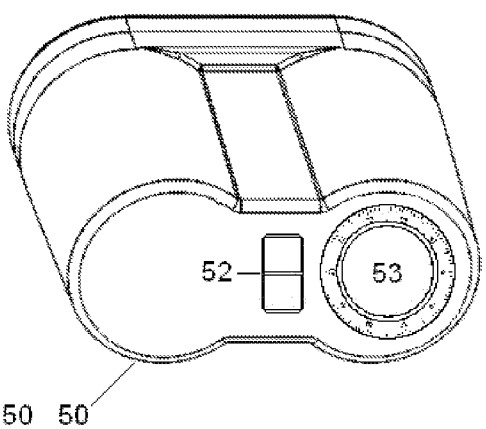
Figure 5C:
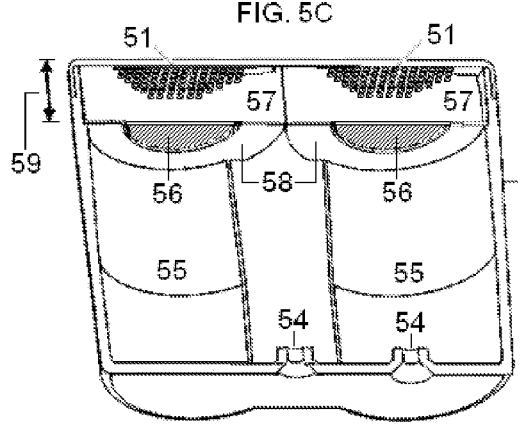

FIGS. 5A and 5C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 5A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 5B and 5C show the bottom of the self-contained stimulator 50. An on/off switch 52 is attached through a port 54, and a power-level controller 53 is attached through another port 54. The switch is connected to a battery power source (320 in FIG. 1B), and the power-level controller is attached to the control unit (330 in FIG. 1B) of the device. The power source battery and power-level controller, as well as the impulse generator (310 in FIG. 1B) are located (but not shown) in the rear compartment 55 of the housing of the stimulator 50.

Individual wires (not shown) connect the impulse generator (310 in FIG. 1B) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (350 in FIG. 1B) to each head compartment 57. An optional non-conducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another. Although the embodiment in FIG. 5 is shown to be a non-capacitive stimulator, it is understood that it may be converted into a capacitive stimulator by replacing the mesh openings 51 with a dielectric material, such as a sheet of Mylar, or by covering the mesh openings 51 with a sheet of such dielectric material.

In a preferred embodiment, the magnetic stimulator coil 341 in FIG. 1A has a body that is similar to the electrode-based stimulator shown in FIG. 5C. To compare the electrode-based stimulator with the magnetic stimulator, refer to FIG. 5D, which shows the magnetic stimulator 530 sectioned along its long axis to reveal its inner structure. As described below, it reduces the volume of conducting material that must surround a toroidal coil, by using two toroids, side-by-side, and passing electrical current through the two toroidal coils in opposite directions. In this configuration, the induced electrical current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

Figure 5D:
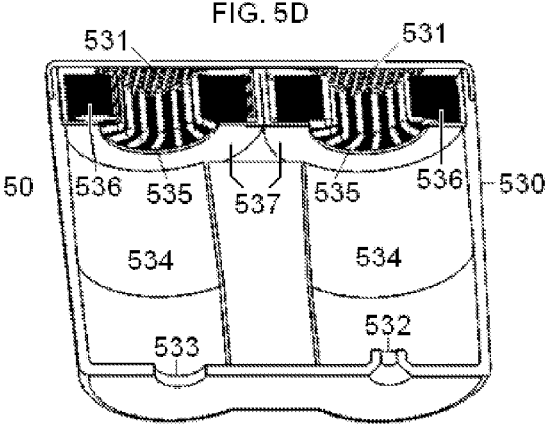

As seen in FIG. 5D, a mesh 531 has openings that permit a conducting gel (within 351 in FIG. 1A) to pass from the inside of the stimulator to the surface of the patient's skin at the location of nerve or tissue stimulation. Thus, the mesh with openings 531 is the part of the magnetic stimulator that is applied to the skin of the patient.

FIG. 5D also shows openings at the opposite end of the magnetic stimulator 530. One of the openings is an electronics port 532 through which wires pass from the stimulator coil(s) to the impulse generator (310 in FIG. 1A). The second opening is a conducting gel port 533 through which conducting gel (351 in FIG. 1A) may be introduced into the magnetic stimulator 530 and through which a screw-driven piston arm may be introduced to dispense conducting gel through the mesh 531. The gel itself is contained within cylindrical-shaped but interconnected conducting medium chambers 534 that are shown in FIG. 5D. The depth of the conducting medium chambers 534, which is approximately the height of the long axis of the stimulator, affects the magnitude of the electric fields and currents that are induced by the magnetic stimulator device [Rafael CARBUNARU and Dominique M. Durand. Toroidal coil models for transcutaneous magnetic stimulation of nerves. IEEE Transactions on Biomedical Engineering. 48 (4, 2001): 434-441].

FIG. 5D also show the coils of wire 535 that are wound around toroidal cores 536, consisting of high-permeability material (e.g., Supermendur). Lead wires (not shown) for the coils 535 pass from the stimulator coil(s) to the impulse generator (310 in FIG. 1A) via the electronics port 532. Different circuit configurations are contemplated. If separate lead wires for each of the coils 535 connect to the impulse generator (i.e., parallel connection), and if the pair of coils is wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As also seen in FIG. 5D, the coils 535 and cores 536 around which they are wound are mounted as close as practical to the corresponding mesh 531 with openings through which conducting gel passes to the surface of the patient's skin. As shown, each coil and the core around which it is wound is mounted in its own housing 537, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium. A difference between the structure of the electrode-based stimulator shown in FIG. 5C and the magnetic stimulator shown in FIG. 5D is that the conducting gel is maintained within the chambers 57 of the electrode-based stimulator, which is generally closed on the back side of the chamber because of the presence of the electrode 56; but in the magnetic stimulator, the hole of each toroidal core and winding is open, permitting the conducting gel to enter the interconnected chambers 534.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance. The currents passing through the coils of the magnetic stimulator will saturate the core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described in connection with FIG. 2. Additional disclosure of the magnetic stimulator shown in FIG. 1A is provided in Applicant's commonly assigned co-pending U.S. patent application Ser. No. 12/964,050, entitled Magnetic Stimulation Devices and Methods of Therapy, to SIMON et al., which is hereby incorporated by reference for all purposes.

In preferred embodiments of the electrode-based stimulator shown in FIG. 1B, electrodes are made of a metal, such as stainless steel, platinum, or a platinum-iridium alloy. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18(2, 2008):35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20(1, 1994):29-35].

For example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71 (1991):746-751].

Although the electrode may consist of arrays of conducting material, the embodiments shown in FIGS. 3 to 5 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6, 2005):448-452; Dejan B. POPOVIC and Mirjana B. Popovic. Automatic determination of the optimal shape of a surface electrode: Selective stimulation. Journal of Neuroscience Methods 178 (2009) 174-181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 3 to 5 provide a uniform surface current density; which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stødkilde-Jørgensen. Current Density Imaging and Electrically Induced Skin Burns Under Surface Electrodes. IEEE Transactions on Biomedical Engineering 52 (12, 2005): 2024-2031; R. H. GEUZE. Two methods for homogeneous field defibrillation and stimulation. Med. and Biol. Eng. and Comput. 21 (1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6, 2006): 368-381; Russell G. MAUS, Erin M. McDonald, and R. Mark Wightman. Imaging of Nonuniform Current Density at Microelectrodes by Electrogenerated Chemiluminescence. Anal. Chem. 71 (1999): 4944-4950]. In fact, patients found the design shown in FIGS. 3 to 5 to be less painful in a direct comparison with a commercially available grid-pattern electrode [UltraStim grid-pattern electrode, Axelggard Manufacturing Company, 520 Industrial Way, Fallbrook Calif., 2011]. The embodiment of the electrode that uses capacitive coupling is particularly suited to the generation of uniform stimulation currents [Yongmin KIM, H. Gunter Zieber, and Frank A. Yang. Uniformity of current density under stimulating electrodes. Critical Reviews in Biomedical Engineering 17(1990, 6): 585-619].

The electrode-based stimulator designs shown in FIGS. 3 to 5 situate the electrode remotely from the surface of the skin within a chamber, with conducting material placed in the chamber between the skin and electrode. Such a chamber design had been used prior to the availability of flexible, flat, disposable electrodes [U.S. Pat. No. 3,659,614, entitled Adjustable headband carrying electrodes for electrically stimulating the facial and mandibular nerves, to Jankelson; U.S. Pat. No. 3,590,810, entitled Biomedical body electrode, to Kopecky; U.S. Pat. No. 3,279,468, entitled Electrotherapeutic facial mask apparatus, to Le Vine; U.S. Pat. No. 6,757,556, entitled Electrode sensor, to Gopinathan et al; U.S. Pat. No. 4,383,529, entitled Iontophoretic electrode device, method and gel insert, to Webster; U.S. Pat. No. 4,220,159, entitled Electrode, to Francis et al. U.S. Pat. No. 3,862,633, U.S. Pat. No. 4,182,346, and U.S. Pat. No. 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 3 to 5 are also self-contained units, housing the electrodes, signal electronics, and power supply. Portable stimulators are also known in the art, for example, U.S. Pat. No. 7,171,266, entitled Electro-acupuncture device with stimulation electrode assembly, to Gruzdowich. One of the novelties of the designs shown in FIGS. 3 to 5 is that the stimulator, along with a correspondingly suitable stimulation waveform, shapes the electric field, producing a selective physiological response by stimulating that nerve, but avoiding substantial stimulation of nerves and tissue other than the target nerve, particularly avoiding the stimulation of nerves that produce pain.

Examples in the remaining disclosure will be directed to methods for using the disclosed electrode-based and magnetic stimulation devices for treating a patient. Selected nerve fibers are stimulated in different embodiments of methods that make use of the stimulation devices. In particular, exemplary methods involve stimulation of the posterior tibial nerve at a location above the patient's ankle in order to treat urine voiding and storage disorders. Among disorders of the lower urinary tract that are described below, the present invention is intended primarily to treat overactive bladder, stress incontinence, urge incontinence, urge frequency, and non-obstructive urinary retention (ischuria). However, other urological disorders may be treated by the disclosed devices and methods as well, such as interstitial cystitis/painful bladder syndrome, which is associated with painful but relatively infrequent urination or with very frequent urination with relatively less pain.

The storage (continence) and voiding (micturition) of urine are performed by the urinary bladder and urethra, which are muscular structures controlled by the nervous system. The lower urinary tract has two phases of activity: the storage phase, when urine is stored in the bladder, and the voiding phase, when urine is released through the urethra. The urethra has two sphincters, an internal smooth muscle sphincter and an external skeletal muscle sphincter. During the storage phase, the sphincters of the urethra contract (blocking flow of urine), and the detrusor smooth muscle of the bladder wall is relaxed. During the voiding phase, the reverse happens—the sphincters of the urethra relax, permitting flow of urine, and the detrusor muscle of the bladder contracts to force urine out through the urethra.

Nerve signals from stretch-sensitive receptors in the bladder wall are sent via the spinal cord to the pontine micturition center in the brainstem and to the cerebrum where voluntary actions are initiated. When the bladder fills and the bladder's stretch-sensitive receptors are actively signaling that filled state, the conscious urge to urinate becomes difficult to ignore. Once the voluntary nerve signal to begin urination has been issued, that signal is sent from the brain via the spinal cord to the lower urinary tract, causing the smooth muscle of the bladder to contract and the urethral sphincter muscle to relax. The flow of urine through the urethra is then sensed by its receptors, and they send nerve signals which help sustain urination until the bladder is empty and the storage phase begins again.

Urinary incontinence is defined by the International Continence Society as "the complaint of any involuntary leakage of urine." There are several types of incontinence, the most common being stress, urge, and overflow incontinence. Stress incontinence is the loss of small amounts of urine as the result of coughing, laughing, sneezing, exercising or other movements that increase intra-abdominal pressure. Urge incontinence is the involuntary loss of urine while suddenly feeling the need or urge to urinate, which is often associated with overactive bladder. Overflow (dribbling) incontinence usually occurs when the patient's bladder is always full so that it frequently leaks urine. It is often caused by obstruction of the urethra, e.g. by an enlarged prostate, but may be associated with non-obstructive urinary retention as well.

Individuals with an overactive bladder exhibit a sudden urge to urinate and a high frequency of urination, especially at night (nocturia). They often, but not always, also exhibit urge incontinence that is associated with the leakage of urine due to bladder muscles that contract or spasm inappropriately. Often these contractions occur regardless of the amount of urine that is in the bladder. Urge incontinence may result from bladder outlet obstruction from an enlarged prostate, inflammation or infection, or neurological disorders, as described below. However, in most cases of urge incontinence, no specific cause can be identified.

Individuals with urge incontinence and mixed incontinence (stress and urge incontinence combined) have overactive bladder (OAB), because they exhibit sudden urges to urinate. However, individuals with OAB do not always exhibit incontinence. Thus, a distinction is made between wet and dry OAB. The prevalence of these conditions depends on the particulars of their definition, which only in the last decade has become standardized. It may also be useful to distinguish subtypes according to storage sympotoms (nocturia, urgency, frequency, urge urinary incontinence, mixed urinary incontinence, stress urinary incontinence), voiding symptoms (intermittency, slow stream, straining, terminal dribble), and post-micturition symptoms (incomplete emptying, post-micturition dribble). The prevalence of OAB is approximately 11-19% in men and 13-17% in women. OAB prevalence increases with age and tends to be more prevalent in women at ages less than 60 years but more prevalent in men at ages greater than 60. In the year 2000, the costs in the United States of urinary incontinence and overactive bladder were estimated to be 19.5 and 12.6 billion dollars, respectively, taking into account costs associated with diagnosis and treatment, as well as consequent costs such as predisposition to urinary tract infections, ulcers, perineal rashes and other skin conditions, infections, falls and broken bones, and premature nursing home admissions. Psychologically, overactive bladder and incontinence are associated with embarrassment, isolation, stigmatization, depression, and the fear of institutionalization [ABRAMS P, Cardozo L, Fall M, Griffiths D, Rosier P, Ulmsten U, van Kerrebroeck P, Victor A, Wein A, and Standardisation Sub-committee of the International Continence Society. The standardisation of terminology of lower urinary tract function: report from the Standardisation Sub-committee of the International Continence Society. Neurourol Urodyn. 21(2, 2002): 167-78; TYAGI S, Thomas C A, Hayashi Y, Chancellor M B. The overactive bladder: Epidemiology and morbidity. Urol Clin North Am. 33(4, 2006): 433-8; HU T W, Wagner T H, Bentkover J D, Leblanc K, Zhou S Z, Hunt T. Costs of urinary incontinence and overactive bladder in the United States: a comparative study. Urology. 63(3, 2004): 461-465; IRWIN D E, Milsom I, Hunskaar S, Reilly K, Kopp Z, Herschorn S, Coyne K, Kelleher C, Hampel C, Artibani W, Abrams P. Population-based survey of urinary incontinence, overactive bladder, and other lower urinary tract symptoms in five countries: results of the EPIC study. Eur Urol. 50(6, 2006): 1306-14; IRWIN D E, Abrams P, Milsom I, Kopp Z, Reilly K; EPIC Study Group. Understanding the elements of overactive bladder: questions raised by the EPIC study. JU Int. 101(11, 2008):1381-7].

A diagnosis of overactive bladder, urge incontinence, and related urological disorders is made preliminarily on the basis of a patient history, aided by the use of questionnaires and micturition diaries that the patient is requested to record. A postvoid residual volume may also be measured, e.g. by ultrasonography. A definitive diagnosis of the etiology of the disorder requires a full urodynamic evaluation, but this is not always necessary to treat the patient. The urodynamic evaluation may be a relatively simple cystometric procedure, wherein a urethral catheter is inserted into the bladder, a syringe is connected to the catheter so that the bladder can be filled, and bladder pressure is recorded during filling and storage, among other measurements. Urodynamic evaluation may instead involve ambulatory urodynamics, wherein microtransducer catheters and a portable recording device are used to record bladder and abdominal pressures during natural bladder filling and emptying, over the course of up to a day during normal daily activities.

As disclosed below, for a patient who might be a candidate for posterior tibial nerve stimulation as a treatment, preliminary ambulatory urodynamic measurements may be useful for designing the nerve stimulation protocol. As also described below, a micturition diary that is more complete than the conventional diary may instead or also be useful for designing the nerve stimulation protocol, especially if it is accompanied by noninvasive, ambulatory measurement of bladder volume. In either case, the preliminary data so acquired may be useful as a reference for how successful any form of treatment has been.

Management options for overactive bladder include lifestyle adjustments, bladder retraining, pelvic floor exercises, biofeedback, and pharmacotherapy (e.g., anticholinergic antimuscarinic medications as the mainstay of treatment, such as oxybutynin, tolterodine, trospium chloride, derifenacin, solifenacin, and fesoterodine fumarate). However, side effects and urinary retention occur in approximately 20% of those who use these medications. In other patients, the medications are ineffective, such that 75% of patients discontinue the use of anticholinergic medications within one year. Major surgical procedures (e.g., bladder augmentation, Burch colposuspension and the pubovaginal sling) are considered last resorts for certain types of incontinence, as they potentially lead to serious side effects. Having failed conservative and drug-based therapies for incontinence, some patients resign themselves to a lifetime of containment devices and pads, rather than resort to surgery [Victor W. NITTI and Jerry G. Blaivas. Urinary Incontinence: Epidemiology, Pathophysiology, Evaluation, and Management Overview. Chapter 60 In: Campbell-Walsh Urology, 9th ed., A J Wein, L R Kavoussi, A C Novick, A W Partin and C A Peters, eds. Philadelphia, Pa.: Saunders Elsevier; 2007. pp 2046-2078; LENTZ G M. Urogynecology: physiology of micturition, diagnosis of voiding dysfunction, and incontinence: surgical and nonsurgical treatment. In: Katz V L, Lentz G M, Lobo R A, Gershenson D M, eds. Comprehensive Gynecology. 5th ed. Philadelphia, Pa.: Mosby Elsevier; 2007: chap 21, pp. 537-568; ANDERSSON K E, Chapple C R, Cardozo L, Cruz F, Hashim H, Michel M C, Tannenbaum C, Wein A J. Pharmacological treatment of overactive bladder: report from the International Consultation on Incontinence. Curr Opin Urol. 19(4, 2009):380-94; ATHANASOPOULOS A, Perimenis P.

Pharmacotherapy of urinary incontinence. Int Urogynecol 1 Pelvic Floor Dysfunct. 20(4, 2009):475-82; GOPAL M, Haynes K, Bellamy S L, Arya L A. Discontinuation rates of anticholinergic medications used for the treatment of lower urinary tract symptoms. Obstet Gynecol. 112(6, 2008):1311-8; HARTMANN K E, McPheeters M L, Biller D H, Ward R M, McKoy J N, Jerome R N, Micucci S R, Meints L, Fisher J A, Scott T A, Slaughter J C, Blume J D. Treatment of overactive bladder in women. Evid Rep Technol Assess (Full Rep). 187 (2009): 1-120; GOODE P S, Burgio K L, Richter H E, Markland A D. Incontinence in older women. JAMA. 303(21, 2010): 2172-81; Courtney L. LEE and Howard B. Goldman. The overactive bladder: new concepts of etiology and treatment. Curr Bladder Dysfunct Rep 5 (2010): 126-134; Eng-Kian LIM and Hann-Chomg Kuo. The treatment of overactive bladder syndrome refractive to antimuscarinic therapy. Incont Pelvic Floor Dysfunct 2(Suppl. 1, 2008) 29-32; CHERNIACK E P. Biofeedback and other therapies for the treatment of urinary incontinence in the elderly. Altern Med Rev. 11(3, 2006):224-31; PRICE N, Dawood R, Jackson S R. Pelvic floor exercise for urinary incontinence: a systematic literature review. Maturitas. 67(4, 2010): 309-15; STARKMAN J S, Smith C P, Staskin D R. Surgical options for drug-refractory overactive bladder patients. Rev Urol 12(2-3, 2010):e97-e110; WAI C Y. Surgical treatment for stress and urge urinary incontinence. Obstet Gynecol Clin North Am. 36(3, 2009):509-19].

If pharmacotherapy is unsuccessful and surgery is not being considered, patients with an overactive bladder or incontinence are increasingly treated by neuromodulation. Many nerves at many anatomical locations have been electrically stimulated in an attempt to treat such urological disorders. Attempts have been made to improve bladder function by stimulating: the bladder wall via a catheter (intravesical stimulation), the bladder directly, the pudendal nerve (transvaginally or using an anal plug or on the perineum or on the clitoris or on the penis or on the periurethral muscle), on a suprapubic area transcutaneously, over the S2 or S3 dermatome transcutaneously, on the tibial nerve transcutaneously or percutaneously, on the sacral spine directly, on the sacral anterior root, on the thigh muscle, and on the foot.

Some such nerve stimulation investigations were originally performed in an attempt to treat patients with neurological problems such as spinal cord injury, spina bifida, or multiple sclerosis, but later investigations were directed to the treatment of non-neurogenic overactive bladder and incontinence that is prevalent in the population at large. For example, in contrast to Brindley's sacral anterior root stimulator that is used to control bladder function in patients with injured spinal cords, sacral neuromodulation for treating overactive bladder uses low amplitude stimulation at or below the sensory threshold, low modulation frequencies, and an almost continuous pulse generator. Thus, "stimulation" sometimes refers to a method that gives an almost immediate effect, whereas "modulation" is intended to cause one neural pathway to influence the pre-existing activity of another pathway through synaptic modulation. The present invention is directed primarily to neuromodulation, although it might nevertheless produce a nearly immediate effect, so in the present context the terms stimulation and neuromodulation are used interchangeably. Furthermore, although the present invention is intended primarily to be used to stimulate the posterior tibial nerve transcutaneously, it is understood that the disclosed devices or their adaptations may also be used to perform transcutaneous neuromodulation on other nerves and at other anatomical locations, including nerves and locations that are described above and in the following publications, and including the sacral nerves S1, S2, S3, S4, or the pudendal nerve, superior gluteal nerve, lumbo-sacral trunk, inferior gluteal nerve, common fibular nerve, tibial nerve, posterior femoral cutaneous nerve, sciatic nerve, and obturator nerve [VAN BALKEN M R, Vergunst H, Bemelmans B L. The use of electrical devices for the treatment of bladder dysfunction: a review of methods. J. Urol. 172(3, 2004):846-51; GAUNT R A, Prochazka A. Control of urinary bladder function with devices: successes and failures. Prog Brain Res. 152 (2006): 163-94; Sandip P. VASAVADA and Raymond R. Rackley. Electrical stimulation for storage and emptying disorders. Chapter 64 in Campbell-Walsh Urology, 9th ed., A J Wein, L R Kavoussi, A C Novick, A W Partin and C A Peters, eds. Philadelphia, Pa.: Saunders Elsevier; 2007. pp 2147-2167; YAMANISHI T, Kama T, Yoshida K I. Neuromodulation for the treatment of urinary incontinence. Int J Urol 15 (2008): 665-672; AL-SHAIJI T F, Banakhar M, Hassouna M M. Pelvic electrical neuromodulation for the treatment of overactive bladder symptoms. Adv Urol. 2011; 2011:757454. Epub 2011 May 14; D E GENNARO M, Capitanucci M L, Mosiello G, Zaccara A. Current state of nerve stimulation technique for lower urinary tract dysfunction in children. J. Urol. 185(May 2011): 1571-7; BURKS F N, Bui D T, Peters K M. Neuromodulation and the neurogenic bladder. Urol Clin North Am. 37(4, 2010): 559-65; OKADA N, Igawa Y, Ogawa A, Nishizawa O. Transcutaneous electrical stimulation of thigh muscles in the treatment of detrusor overactivity. Br J. Urol. 81(4, 1998):560-4; TAI C, Shen B, Chen M, Wang J, Liu H, Roppolo J R, de Groat W C. Suppression of bladder overactivity by activation of somatic afferent nerves in the foot. JU Int. 107(2, 2011):303-9; Bary BERGHMANS, Kari Bo, Erik Hendriks, Rob de Bie, Marijke van Kampen. Electrical stimulation with non-implanted electrodes for urinary incontinence in adults. Cochrane database of systematic reviews 2004 (updated 2009), Issue 3, Art. No. CD001202, pp 1-9].

Sacral nerve electrical stimulation is currently the most common form of neuromodulation that is used to treat overactive bladder and incontinence. Humans have 31 left-right pairs of spinal nerves, each roughly corresponding to a segment of the vertebral column: 8 cervical spinal nerve pairs (C1-C8), 12 thoracic pairs (T1-T12), 5 lumbar pairs (L1-L5), 5 sacral pairs (S1-S5) and 1 coccygeal pair. Sacral nerve modulation was developed based on the observation that the S2-S4 nerve roots provide the primary innervation to the bladder and urethra. With sacral nerve modulation, patients first undergo a screening with percutaneous nerve evaluation, in which a temporary wire electrode is inserted in the S3 foramen. Patients who show a 50% or greater improvement in one or more urine voiding parameters after 3-7 days of electrode stimulation are offered a permanent implant. The permanent electrode is then implanted as follows. A midline sacral incision is made, the paravertebral muscles are separated, and an insulated electrode is placed in the S3 sacral foramen. Another incision is made over the upper buttock, creating a pocket in which the neurostimulator is placed. The electrode and stimulator are connected with leads, the incisions are closed, and after a week, the stimulator is programmed for therapeutic use. The procedure is expensive, and problems arise in up to a third of the patients, including change in bowel function, infection, lead movement, pain at implant sites, and/or unpleasant stimulation or sensation.

Percutaneous tibial nerve stimulation (PINS, also known as posterior tibial nerve stimulation) offers a safer, less invasive treatment alternative for overactive bladder than sacral nerve neuromodulation. Rather than requiring an incision and placement of electrodes in the sacrum, PINS stimulates sacral nerve roots, but at a location much closer to the surface of the skin, at the posterior tibial nerve slightly above the ankle. The rationale is that the tibial nerve, a branch of the sciatic nerve, is derived from spinal nerves L4 through S3, which are known to be involved in the control of the bladder. Direct electrical stimulation of the tibial nerve was reported by McGuire and colleagues in 1983, but its use for treating bladder and incontinence problems was developed by Stoller beginning in 1987 [GOVIER F E, Litwiller 5, Nitti V, Kreder K J Jr, Rosenblatt P. Percutaneous afferent neuromodulation for the refractory overactive bladder: results of a multicenter study. J. Urol. 165(4, 2001):1193-8].

PTNS must be distinguished from acupuncture with electrical stimulation. In electrical acupuncture, needles are also inserted just below the skin, but the placement of needles is based on specific theories regarding energy flow throughout the human body. Thus in PTNS, the location of stimulation is the posterior tibial nerve directly, rather than a location using the theories of energy flow that guide placement of stimulation for acupuncture. Many acupuncture points have been used to treat urinary incontinence, including the SP6 point that is near the one used for PTNS [BERGSTROM K, Carlsson C P, Lindholm C, Widengren R. Improvement of urge- and mixed-type incontinence after acupuncture treatment among elderly women—a pilot study. J Auton Nery Syst. 79(2-3, 2000):173-80].

To perform PTNS, a sensitive pressure point is identified approximately 3 finger breadths cephalad from the medial malleolus and about 1 finger breadth posterior from the edge of the tibia. A needle is inserted through the skin approximately 3 to 4 cm posterior to the tibia. The angle of the needle is 60 degrees cephalad from a perpendicular line along the length of the tibia. A ground pad is placed over the medial aspect of the calcaneus. A stimulator is then connected to the needle and the ground pad. A current 0.5-9 mA at 20 Hz provides stimulation. Each treatment session lasts 30 minutes, and the sessions are conducted weekly. After 12 months, statistically significant improvements compared with baseline are seen for frequency (2.8 fewer voids daily), urge incontinence (1.6 fewer episodes daily), nocturia (0.8 fewer void per night), and voided volume (39 more mL per void) and on subjective questionnaires [GOVIER F E, Litwiller S, Nitti V, Kreder K J Jr, Rosenblatt P. Percutaneous afferent neuromodulation for the refractory overactive bladder: results of a multicenter study. J Urol 165(4, 2001): 1193-8; MACDIARMID S A, Peters K M, Shobeiri A, et al. Long-term Durability of Percutaneous Tibial Nerve Stimulation for the Treatment of Overactive Bladder. J Urol 183 (2010):234-240; FINAZZI-AGRO E, Petta F, Sciobica F, Pasqualetti P, Musco S, Bove P. Percutaneous tibial nerve stimulation effects on detrusor overactivity incontinence are not due to a placebo effect: a randomized, double-blind, placebo controlled trial. J. Urol. 184(5, 2010): 2001-6].

The following patents or patent applications also include the tibial nerve as one of their points of stimulation to treat urological problems, but they are concerned only with implanted, invasive stimulation devices: U.S. Pat. No. 6,941, 171 to MANN et al, entitled Implantable stimulator systems and methods for treatment of incontinence and pain; U.S. Pat. No. 7,729,772 to WILLIAMS et al, entitled Implantable neuromodulation system and method; and U.S. Pat. No. 6,735, 474 to LOEB Implantable stimulator system and method for treatment of incontinence and pain; and patent applications US20060122660 to BOVEJA et al, entitled Method and system for modulating sacral nerves and/or its branches in a patient to provide therapy for urological disorders and/or fecal incontinence, using rectangular and/or complex electrical pulses; and US20090326602 to GLUKHOVSHY et al, entitled Treatment of indications using electrical stimulation. PTNS has also been used in combination with other modalities for the treatment of incontinence [Patent application US20090076565 to SURWIT, entitled Methods for treating urinary and fecal incontinence].

A therapeutic application of the disclosed electrode-based and toroidal magnetic stimulation devices is to treat urinary incontinence and/or overactive bladder by stimulating the tibial nerve noninvasively, at or near the site where the above-described percutaneous tibial nerve stimulation is performed. Noninvasive stimulation of the posterior tibial nerve has been performed with conventional surface electrodes, as described in the following publications, thereby eliminating problems associated with needle insertion. However, the use of surface electrodes as performed in those publications does not eliminate the possibility of pain from the electrical stimulation itself at higher stimulation power, which is a problem that the present invention addresses. It also does not eliminate the potential limitation on therapeutic stimulus power that is due to a low threshold for unwanted, concomitant stimulation of muscles in the foot, which the present invention also addresses [NAKAMURA M, Sakurai T, Tsujimoto Y, Tada Y. Transcutaneous electrical stimulation for the control of frequency and urge incontinence. Hinyokika Kiyo. 29(9, 1983): 1053-9; GEIRSSON G, Wang Y H, Lindstrom S, Fall M. Traditional acupuncture and electrical stimulation of the posterior tibial nerve. A trial in chronic interstitial cystitis. Scand J Urol Nephrol. 27(1, 1993):67-70; AMARENCO G, Ismael S S, Even-Schneider A, Raibaut P, Demaille-Wlodyka S, Parratte B, Kerdraon J. Urodynamic effect of acute transcutaneous posterior tibial nerve stimulation in overactive bladder. J. Urol. 169(6, 2003):2210-5; SCHREINER L, dos Santos T G, Knorst M R, da Silva Filho I G. Randomized trial of transcutaneous tibial nerve stimulation to treat urge urinary incontinence in older women. Int Urogynecol J. 21(9, 2010): 1065-70; DE SEZE M, Raibaut P, Gallien P, Even-Schneider A, Denys P, Bonniaud V, Game X, Amarenco G. Transcutaneous posterior tibial nerve stimulation for treatment of the overactive bladder syndrome in multiple sclerosis: results of a multicenter prospective study. Neurourol Urodyn. 30(3, 2011):306-11].

The present invention differs from these applications of transcutaneous posterior tibial nerve stimulation in several respects. First, the invention discloses electrode configurations that differ from those used previously. Unlike the earlier reports of transcutaneous PTNS, the present disclosure uses a configuration that is applied axially along the nerve course, which is also recommended for a different application, namely, the measurement of somatosensory evoked potentials [HU Y, Xie X B, Pang L Y, Li X H, Luk K D. Current density distribution under surface electrode on posterior tibial nerve electrical stimulation. Conf Proc IEEE Eng Med Biol Soc. 4 (2005):3650-2]. An advantage of the present invention is that its stimulator designs permit transcutaneous stimulation of a long, straight segment of the tibial nerve at a location that lies relatively deep under the skin, rather than limiting successful stimulation to only a location corresponding to the approximately shortest distance from the tibial nerve to the skin, as had been described in previous reports of percutaneous and transcutaneous tibial nerve stimulation. Furthermore, the disclosed devices shape an elongated electric field of effect that can be oriented parallel to the posterior tibial nerve. In contrast, the above-cited applications of transcutaneous posterior tibial nerve stimulation simply use two conventional self-adhesive surface stimulation electrodes, with one of the electrodes not lying over the tibial nerve with any certainty, and without shaping of the electric field as defined herein.

Second, the devices disclosed here are able to deliver higher currents without causing pain, owing to the geometry and configuration of the electrodes within the devices shown in FIGS. 3 to 5, as well as the novel stimulation waveform that is illustrated in FIG. 2. They may also achieve higher stimulation currents without causing movement of the toes and foot, provided that suitable parameters of the stimulation waveform are selected. Thus, higher power of stimulation is possible with the disclosed devices, in part, because the waveforms described herein are significantly different than the waveforms used in the above-cited applications of transcutaneous tibial nerve stimulation.

Third, the present invention contemplates stimulation during particular phases of respiration as a method for eliminating a potential contributor to pain. This is because stimulation during expiration may not be perceived as painful, even though the same stimulus delivered during inspiration would be perceived as painful [GREEN D A, Bowtell J, Turner D L. Electrical percutaneous tibial stimulation modulates within-a-breath respiratory drive in man. Respir Physiol Neurobiol. 161(2, 2008):214-7]. More generally, the present invention uses different stimulation waveforms than those used in previous reports of transcutaneous tibial nerve stimulation, and that stimulation may be delivered preferentially during particular physiological phases, as also described below in connection with phases of bladder filling.

Fourth, the present invention treats overactive bladder, incontinence, and related urological disorders through a novel method and mechanism that is disclosed below in connection with a discussion of the physiological basis of tibial nerve stimulation. Unlike the above-cited publications that make use of transcutaneous posterior tibial nerve stimulation, the present invention contemplates individualizing the selection of parameters of the stimulation protocol for each patient, based upon the disclosed method.

Fifth, the present invention discloses use of a novel magnetic stimulator that may be applied to the posterior tibial nerve, as an alternative to electrode-based stimulation devices. Conventional magnetic stimulation has also been used previously to treat urinary incontinence and overactive bladder, as described in the publications cited below, but those investigations did not involve stimulation of the tibial nerve near the ankle as in PTNS. Furthermore, the magnetic stimulation device that is disclosed herein is designed to not generate a magnetic field within bodily tissue, in contrast to previous magnetic stimulation devices that create eddy currents through the introduction of a magnetic field within the body [GALLOWAY N T, EI-Galley R E, Sand P K, Appell R A, Russell H W, Carlin S J. Extracorporeal magnetic innervation therapy for stress urinary incontinence. Urology 53 (1999): 1108-11; FUJISHIRO T, Takahashi S, Enomoto H, Ugawa Y, Ueno S, Kitamura T. Magnetic stimulation of the sacral roots for the treatment of urinary frequency and urge incontinence: an investigational study and placebo controlled trial. J Urol 168(3, 2002):1036-9; TAKAHASHI S and Kitamura T. Overactive bladder: magnetic versus electrical stimulation. Current Opinion in Obstetrics & Gynecology 15(5, 2003): 429-33; BUT I. Conservative treatment of female urinary incontinence with functional magnetic stimulation. Urology 61(3, 2003): 558-61; GILLING P J, Wilson L C, Westenberg A M, McAllister W J, Kennett K M, Frampton C M, et al. A double-blind randomized controlled trial of electromagnetic stimulation of the pelvic floor vs sham therapy in the treatment of women with stress urinary incontinence. BJU International 103 (10, 2009): 1386-1390; Nobuyuki KAI, Masakazu KAWAJIRI, Narihito SEKI, Naruaki TAKANO, Jun-ichi KIRA, Shozo TOBIMATSU, and Seiji NAITO. Efficacy of High-frequency Magnetic Stimulation of the Sacral Root in Patients with Urinary Incontinence Following a Radical Prostatectomy. LUTS (2010) DOI: 10.1111/j.1757-5672.2010.00062.x, pp. 1-5].

Sixth, the present invention provides a novel treatment algorithm wherein electrical impulses are transmitted to the patient in a treatment session having a period of between about 3 minutes and three hours, followed by a period of about three hours to one week wherein the electrical impulses are not transmitted to the patient. In a preferred embodiment, the electrical impulses are transmitted when the patient's bladder-filling is in a phase selected from among: a refractory phase following urination wherein the patient has no desire to urinate, a phase beginning with a first desire to urinate and ending before a strong desire to urinate and a phase beginning with strong desire to urinate that cannot be ignored by the patient. The electrical impulses are preferably transmitted when the bladder of the patient has a bladder filling-volume that is within a predetermined range of volumes.

The method and devices disclosed in the following patents also deal with the treatment of incontinence using magnetic stimulation, but they are not designed to stimulate the tibial nerve as in the PTNS method described above: U.S. Pat. No. 5,984,854, entitled Method for treating urinary incontinence and an apparatus therefor, to Ishikawa; and U.S. Pat. No. 6,086,525, entitled Magnetic nerve stimulator for exciting peripheral nerves to Davey et al. A family of applications related to patent application US20100222629, entitled Method and apparatus for magnetic induction therapy, to BURNETT et al; and application US20100222630, entitled Method and apparatus for low frequency induction therapy for the treatment of urinary incontinence and overactive bladder, to MANGRUM et al, uses an unconventional adjustable coil that neither passes high current through the coil nor uses a magnetic core to increase the stimulus. It is therefore not designed to stimulate the tibial nerve as deeply, powerfully or selectively as the device disclosed herein. Furthermore, the device disclosed herein does not generate a magnetic field within bodily tissue, in contrast to the other devices that create eddy currents through the application of a magnetic field within the body.

Although devices disclosed herein are intended for the treatment of overactive bladder and incontinence by stimulating the tibial nerve, it is understood that the devices may also be used for other disorders that may be treated by stimulating the tibial nerve. Those other disorders include fecal incontinence [FINDLAY J M, Maxwell-Armstrong C. Posterior tibial nerve stimulation and faecal incontinence: a review. Int J Colorectal Dis. 26(3, 2011):265-73], spasticity [AYDIN G, Tomruk S, Keles I, Demir S O, Orkun S. Transcutaneous electrical nerve stimulation versus baclofen in spasticity: clinical and electrophysiologic comparison. Am J Phys Med Rehabil. 84(8, 2005): 584-92], and chronic pelvic pain [VAN BALKEN M R, Vandoninck V, Messelink B J, Vergunst H, Heesakkers J P, Debruyne F M, Bemelmans B L. Percutaneous tibial nerve stimulation as neuromodulative treatment of chronic pelvic pain. Eur Urol. 43(2, 2003):158-63; Patent application US20110071594 to BAROLAT et al, entitled Posterior tibial nerve and/or other nerve stimulation system and method].

Figure 6:
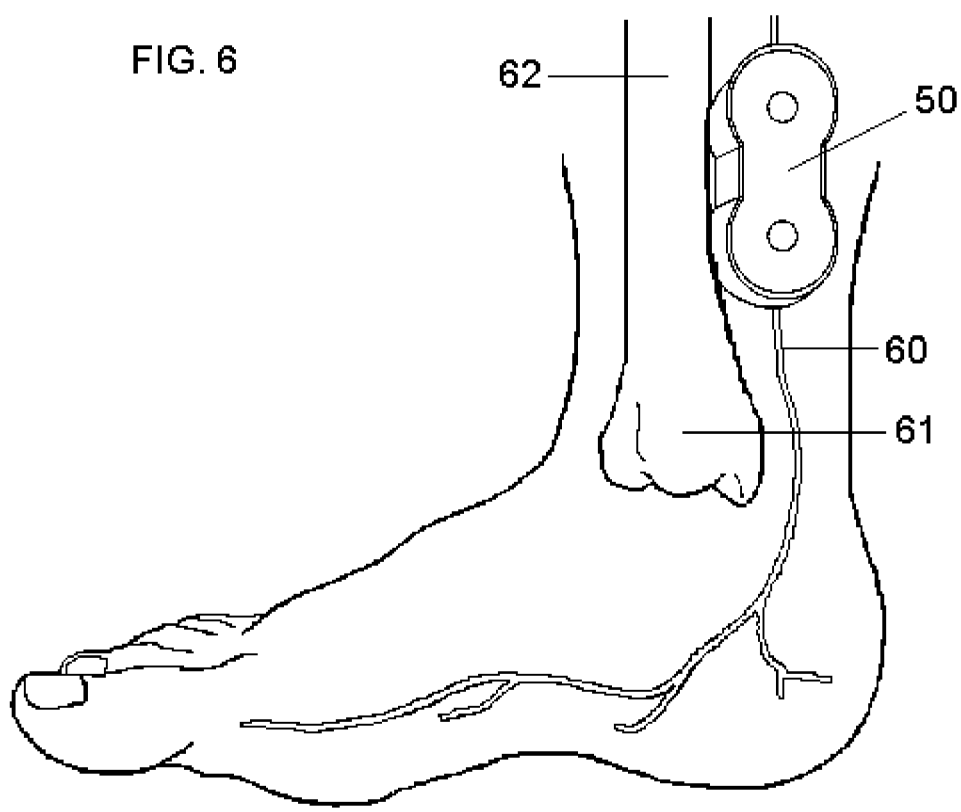
FIG. 6 illustrates the approximate position of the housing of a dual-electrode or magnetic stimulator according the present invention, when the stimulator is used to stimulate the posterior tibial nerve above the ankle of a patient.

FIG. 6 illustrates use of the devices shown in FIGS. 3 to 5 to stimulate the posterior tibial nerve, in which the stimulator device 50, shown also in FIG. 5, is shown to be applied to an exemplary target location above the patient's ankle. The illustration would also apply to the application of the magnetic stimulator device 530 in FIG. 5D. In a preferred embodiment, the method stimulates the posterior tibial nerve 60, which runs down the lower leg (crus) and into the foot as indicated in FIG. 6. To perform the stimulation, a stimulation device of the present invention is positioned approximately 3 finger breadths cephalad from the protruding medial malleolus 61 and about 1 finger breadth posterior from the edge of the tibia 62. It is understood that the device is connected via wires or cables (not shown) to an impulse generator 310 as in FIG. 1. Conducting medium (e.g., conducting gel) may also be dispensed to the patient's skin if desired.

The position and angular orientation of the device are then adjusted about that location until the patient perceives a maximum of stimulation when current is passed through the electrodes or magnetic coil. The applied current is increased gradually, first to a level where the patient feels sensation anywhere that there is innervation of the tibial nerve, as indicated, for example, by flexing of the big toe and/or fanning or plantar toe flexion of ipsilateral digits 2 through 5. The parameters of stimulation are then adjusted in an attempt to eliminate that muscular movement, yet maintain the increasing applied current. The power is ultimately set to a level that is less than one at which the patient first indicates any discomfort and less than one at which there is movement of the muscles. Straps, harnesses, or frames are used to maintain the stimulator in position (not shown in FIG. 6).

The stimulation is then performed with a sinusoidal burst waveform like that shown in FIG. 2. The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse within a burst has a duration of 20 to 1000 microseconds, preferably 200 microseconds. A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well. The stimulation is then performed typically for 30 minutes and the treatment is performed once a week for 12 weeks or longer. However, it is understood that parameters of the stimulation protocol may be varied in response to heterogeneity in the pathophysiology of patients.

The individualized selection of parameters for the stimulation protocol may based on trial and error in order to obtain a beneficial response without the sensation of pain or muscle twitches, as indicated for example, by the patient experiencing on average fewer daily urinary voids, and/or fewer daily episodes of urge incontinence, and/or fewer urinary voids per night, and/or increased urinary volumes per void, and/or improved patient emotional well-being. Ordinarily, the amplitude of the stimulation signal is set to the maximum that is comfortable for the patient, and then the other stimulation parameters are adjusted.

Individualized treatment may also be based on the methods that are described below in connection with the description of the bladder as a set of semi-autonomous muscular modules that may be described as coupled nonlinear oscillators. In brief, the bladder is described by a set of coupled non-linear differential equations corresponding to coupled nonlinear oscillators (e.g., Van der Pol limit cycle oscillators); preliminary measurements, concerning the patient's bladder and urethra function, are made on individual segments of the patient's bladder, or ambulatory urodynamic measurements are made, or detailed logging of the patient's urinary tract sensations are recorded with the aid of an electronic diary and noninvasive bladder volume measurement; parameters of the equations are estimated using the measurements; many potential treatment protocols are simulated by solving the differential equations, including treatments that vary stimulation parameters and that preferentially stimulate at different phases of bladder filling; and a treatment protocol is selected from the simulations that will minimize unwanted bladder contractions or other undesired events.

Treatment may be performed on the posterior tibial nerve 60 near either or both ankles, and it may be performed alternately on the tibial nerves in the left and right legs. If treatment is performed on only one leg, the selected leg is ordinarily the one that is used in daily activities, such as kicking a football. If the treatment of is performed on both legs, an alternating stimulation protocol may be one that is timed to inhibit nerve signals that would be associated with walking movements, according to the methods that are described below in connection with the relation between the tibial nerve and locomotive central pattern generators in the spine, and their supraspinal control.

If it is desired to maintain a constant power of stimulation in the vicinity of the tibial nerve (or any other nerve or tissue that is being stimulated), methods may also be employed to modulate the power of the stimulator in order to compensate for patient motion or other mechanisms that would otherwise give rise to variability in the power of stimulation. Methods for compensating for motion and other confounding factors were disclosed by the present Applicant in commonly assigned co-pending application Ser. No. 12/859,568 entitled Non-Invasive Treatment of Bronchial Constriction, to SIMON et al, which is hereby incorporated by reference.

In other embodiments of the invention, pairing of tibial nerve stimulation may be with a time-varying sensory stimulation. The paired sensory stimulation may be bright light, sound, tactile stimulation, or electrical stimulation, e.g., pulsating with the same frequency as the tibial nerve electrical stimulation. The rationale for paired sensory stimulation is the same as paired stimulation of both left and right tibial nerves, namely, that the pair of signals interacting with one another in the spinal column or brain may result in the formation of larger and more coherent neural ensembles than the neural ensembles associated with the individual signals, thereby enhancing the therapeutic effect. For example, the hypothalamus is well known to be responsive to the presence of bright light, so exposing the patient to bright light that is fluctuating with the same stimulation frequency as the tibial nerve (or a multiple of that frequency) may be performed in an attempt to enhance the role of the hypothalamus in producing the desired therapeutic effect. As another example, electrical stimulation of the tibial nerve may be paired with stimulation of the pudendal nerve. Such paired stimulation does not necessarily rely upon neuronal plasticity and is in that sense different from other reports of paired stimulation [Navzer D. ENGINEER, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature 470(7332, 2011): 101-4].

To understand a novel mechanism by which the disclosed stimulation of the tibial nerve modulates urinary voiding and incontinence, consider first the anatomy of the tibial and related nerves, as illustrated in FIG. 7, which shows nerves in a posterior view of an individual. After the spinal cord terminates in the lower thoracic spine, nerve roots from the lumbar and sacral levels come off the bottom of the spinal cord like a "horse's tail" (cauda equina) and exit the spine. Fanning-out of the caudia equina in the sacral plexus is illustrated in FIG. 7B, showing nerves derived from axons from the fourth and fifth lumbar (L4 and L5) and first through fifth sacral (S1, S2, S3, S4 and S5) spine nerve roots, as well as the single coccygeal nerve root. Correspondence of the nerve roots to the locations of the fourth lumbar vertebra and coccyx (tailbone) is indicated in FIG. 7A. The L5 and S1 to S5 vertebra are located successively between the fourth lumbar vertebra and coccyx, but their locations are not marked in FIG. 7A. Note that the sacrum, which is located between the lumbar vertebrae and coccyx, consists of five fused vertebrae with holes (sacral foramina) through which spinal nerves exit.

The tibial nerve 77 is derived from axons from fourth and fifth lumbar (L4 and L5) and first, second, and third sacral (S1, S2, and S3) spine nerve roots. Near the spine nerve roots, the tibial nerve 77 is a branch of the sciatic nerve 76, which has the common peroneal nerve 78 as its other main branch. Descending into the thigh, the anterior component of the tibial nerve 77 supplies muscles of the posterior thigh, except for the short head of the biceps, which is supplied by peroneal nerve 78. The tibial nerve passes through the popliteal fossa (knee pit) to pass below the arch of soleus. In the popliteal fossa the tibial nerve gives off branches to gastrocnemius, popliteus, soleus and plantaris muscles, an articular branch to the knee joint, and a cutaneous branch that will become the sural nerve. The tibial nerve 77 then passes into the posterior compartment of leg to lie deep to the transverse crural septum to become the posterior tibial nerve 60, where it supplies the tibialis posterior, flexor hallucis longus and flexor digitorum longus muscles. The posterior tibial nerve 60 passes behind medial malleolus 61 (see also 61 in FIG. 6) to the plantar side of the foot and divides within the tarsal tunnel into the medial and lateral calcaneal nerves (sensory nerves to the heel of the sole), medial plantar nerve (sensory nerve to the medial three toes and innervating the abductor hallucis brevis, flexor hallucis brevis, flexor digitorum brevis and lumbricales muscles) and lateral plantar nerve (sensory nerve for the little and lateral fourth toe, and innervating the abductor digiti quinti brevis, flexor digitorum brevis and quadratus plantae muscles).

Also shown in FIG. 7A are the principal bones of the leg: the femur 79, tibia 62 and fibula 63. The pudendal nerve 75 is also shown in FIG. 7B, branches of which are seen to accompany the tibial nerve 77 (and therefore the sciatic nerve 76) at S2 and S3. The pudendal nerve is a somatic nerve in the pelvic region that innervates the external genitalia of both sexes, as well as sphincters for the bladder and the rectum. It originates in Onuf's nucleus in the sacral region of the spinal cord, as described below in connection with FIG. 8.

Figure 8:
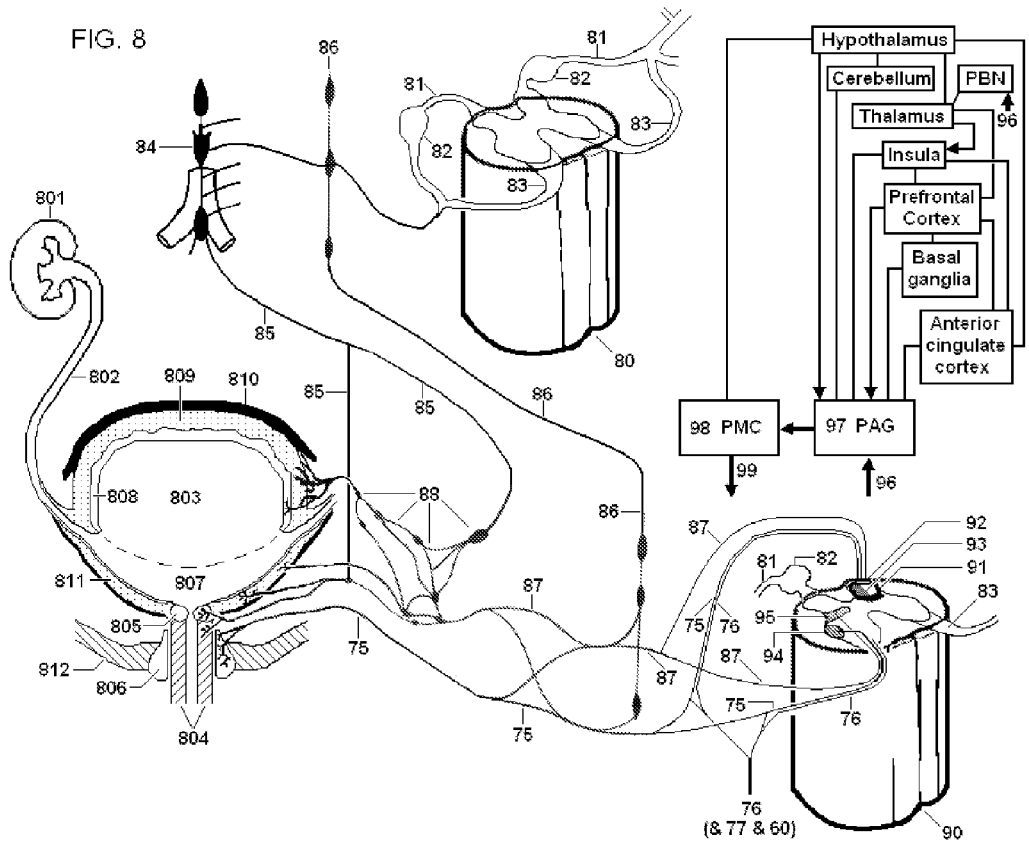
FIG. 8 illustrates components of the bladder and urethra, as well as peripheral, spinal and supraspinal components of the nervous system that control continence and micturition by the bladder and urethra.

Referring now to FIG. 8, urine is formed in a kidney 801 and is then propelled by a muscular tube, the ureter 802, to the urinary bladder 803. The urethra 804 is a muscular tube at the base of the bladder that connects the urinary bladder 803 to the genitals for the removal of urine from body. In males, the urethra travels through the penis, and in females, the urethra emerges above the vaginal opening. Although the bladder 803 shown in FIG. 8 is shown to have relatively regular oblate shape, in fact it has a complex, irregular shape that changes during filling and voiding [Naoki YOSHIMURA and Michael B. Chancellor. Physiology and pharmacology of the bladder and urethra. Chapter 56 in Campbell-Walsh Urology, 9th ed., A J Wein, L R Kavoussi, A C Novick, A W Partin and CA Peters, eds. Philadelphia, Pa.: Saunders Elsevier; 2007. pp 1922-1972]. This fact is relevant to the present invention in connection with the micro-motion that modules or segments of bladder muscle can exhibit.

For urine to exit the bladder through the urethra 804, both an autonomically controlled internal sphincter 805 and a voluntarily controlled external sphincter 806 must be relaxed in an opened position. The trigone 807 is a smooth triangular region of the internal urinary bladder formed at its vertices by the internal urethral sphincter 805 and the two ureter orifices (bounded at its top by dashed lines in FIG. 8). The trigone is very sensitive to expansion, and once it is stretched, nerves ending there send signals to the brain communicating the need to urinate (see below).

Proceeding outwards from the lumen of the bladder, the bladder wall contains three main layers: the mucosal layer 808 (mucosa/submucosa layer, comprising urothelium and lamina propria), the detrusor muscle layer 809 (comprising sublayers of inner longitudinal, circular, and outer longitudinal muscle), and a serosa layer 810 (comprising the serosa/peritoneum for lubrication, adventitia for connection to surrounding tissue, and perivesical fat). Within the wall of the upper dome to equatorial region of the urinary bladder (called simply the dome region, to contrast it with the trigone and bladder neck base region), detrusor smooth muscle 809 contracts during urination to force urine through the open lumen of the urethra 804. Otherwise, when the spincters are constricted, the detrusor muscle 809 remains relatively relaxed to allow the bladder to fill, except for local contractions as described below. Smooth muscle 811 is also found within the base of the bladder and proximal urethra, the internal sphincter 805 being integrally connected to that muscle. Detrusor muscle within the dome of the bladder 809 differs from smooth muscle within the base of the bladder 811 in that the dome muscle is primarily under beta-adrenergic and muscarinic (M2 and M3) control, whereas the base muscle is primarily under alpha-adrenergic control. This difference in control of dome-versus-base musculature allows the dome muscle to contract while the base muscle is relaxed, and vice versa.

The urinary bladder sits on the pelvic floor 812, which is composed of muscle fibers and connective tissue, through which the urethra 804 passes. Because contraction of the muscles of the pelvic floor may assist contraction of muscle of the external sphincter 806, pelvic floor exercise may assist incontinent individuals.

Coordination between the bladder and its outlet (bladder neck, urethra, and urethral sphincters) is mediated primarily by sympathetic (hypogastric 85), parasympathetic (pelvic 87) and somatic (pudendal 75) nerves. All three of those nerves relay afferent sensory information from the bladder or its outlet to spinal and supraspinal centers where the information is processed. They also send efferent signals back from those centers to the bladder and its outlet, e.g., to cause the detrusor muscle 809 to contract and sphincters (805 and 806) to open during urination [KANAI A and Andersson K E. Bladder Afferent Signaling: Recent Findings. J Urol 183(4, 2010): 1288-95; L. BIRDER and M. Drake, eds. Neural Control (Committee 3), In: Incontinence (International Consultation on Incontinence, 4th edition, 2009), Paul Abrams, Linda Cardozo, Saad Khoury, and Alan Wein, eds. Health Publications, Ltd., distributed by EDITIONS 21, 76 Rue de la Pompe 75016 France., pp. 167-254]. As described below, according to the present invention, that coordination may be modulated through stimulation of the sciatic nerve 76, tibial nerve 77, or posterior tibial nerve 60 (see also FIG. 7).

Nerves that approach the spine, such as L4 through S5 shown in FIG. 7B, form branches (as in the top forks of a Y), to enter the back (dorsal) and front (ventral) sides of the spine through small openings called intervertebral foramen. Those nerve branches are known as dorsal (or posterior or sensory) and ventral (or anterior or motor) roots, respectively. A nodule is present on the dorsal root, known as a dorsal root ganglion, which contains cell bodies of neurons in afferent spinal nerves. Thus, the bodies of sensory nerve cells are not located in the spinal cord, but are instead located in small aggregations within dorsal root ganglia.

Because the nerves are paired as left and right, the dorsal and ventral roots at each segment of the spine are correspondingly paired. This is illustrated in FIG. 8, which shows two portions of the spine that are involved in the control of urine storage and micturition reflexes. The one labeled as 80 is the portion of the spine (T10, T11, T12, L1 and L2) that is associated with control via the sympathetic nervous system. For each of its segments, there are left and right dorsal roots 81, left and right dorsal root ganglia 82, and left and right ventral roots 83.

Sympathetic nerves originate in the T12-L2 segments of the spinal cord and run through the inferior mesenteric plexus 84 and the hypogastric nerve 85 or through the sympathetic chain 86 to enter the pelvic nerves 87. The pelvic plexus 88 (also known as the inferior hypogastric plexus) is a plexus of nerves that supplies the viscera of the pelvic cavity, which is supplied by the pelvic nerve 87, the hypogastric nerve 85, and the sympathetic chain 86. As illustrated in FIG. 8, nerves from the pelvic plexus, hypogastric nerve, and pelvic nerve innervate different layers of the wall of the bladder.

The sacral portion of the spine labeled as 90 in FIG. 8 is connected with the tibial nerve, particularly the sacral segments S1, S2, and S3, as seen in FIG. 7B. Thus, near the spine nerve roots, the tibial nerve 77 (including its lower segment, the posterior tibial nerve 60) is a branch of the sciatic nerve 76. As seen also in FIG. 7B, the pudendal nerve 75 has branches that merge with those of the tibial nerve (and therefore the sciatic nerve) as it approaches S2 and S3.

For clarity in FIG. 8, only the right dorsal root 81, right dorsal root ganglion 82, and left ventral root 83 are labeled within the sacral portion 90, so as to reveal particular nerves that emanate from the left dorsal root, left dorsal root ganglion, and right ventral root. For clarity of illustration, afferent (sensory) nerves are shown as emanating from the left dorsal root, and efferent (motor) nerves are shown as emanating from the right ventral root, although it is understood that afferent and efferent nerves actually emanate from both left and right sides, as shown for the spinal portion labeled as 80.

As also shown in 80 and 90 of FIG. 8, the center of the vertebrae of the spine is composed of gray matter nervous tissue, surrounded by white matter nervous tissue. In a cross-section, the gray matter has a characteristic H shape, and the tips of the H are known as horns. There are two dorsal horns and two ventral horns, which connect to the two dorsal and two ventral roots, respectively. Somatic motor neurons that supply skeletal muscles (e.g., of the external urethral sphincter 806) are located primarily in the ventral horn. The motor neurons that are closest to the midline of the spinal cord innervate muscles of the trunk, while those that are more lateral innervate the extremities (e.g., leg, foot and toe innervations of the tibial nerve motor neurons). As indicated above, the bodies of sensory neurons are found in the dorsal root ganglia. Their axons enter the spinal cord through the dorsal root and often synapse on small interneurons in the gray matter of the dorsal horn, which relay incoming sensory signals to both motor neurons and other sensory neurons.

Regions of nervous tissue within the sacral horns that are particularly relevant to the control of urine storage and micturition reflexes are labeled within 90. For clarity of illustration, afferent components are shown only on the patient's left side, and efferent and somatic components are shown only on the patient's right side. However, it is understood that in reality, all components are distributed bilaterally and that they overlap extensively. Components that process signals from afferent fibers of the bladder, external urethral sphincter, urethra, and genitals are labeled as 91. Within the sacral segment 90, those afferent fibers are delivered primarily via the pelvic nerve 87 and pudendal nerve 75. For example, pelvic nerve afferents sense the volume and contraction of the bladder, and they consist of myelinated Aδ and unmyelinated C axons.

These afferent fibers enter the cord and travel rostrocaudally within Lissauer's tract 92, which is adjacent to one side of the component 91. The opposite side of 91 is connected via lateral and medial projections, such that the component 91 is roughly ring-shaped. Within the ring, a cutaneous perineal component 93 connects to afferent fibers of the perineal nerve (arising from the pudendal nerve) that innervate the perineal skin, i.e., the surface skin region between the anus and the scrotum or vaginal opening. The external urethral sphincter motoneurons are located along the lateral border of the ventral horn in a region known as Onuf's nucleus 94, which is the origin of the pudendal nerve 75. The sacral parasympathetic nucleus 95 is located in a region that is symmetric with the lateral/central portion of the afferent component 91 between the ventral and dorsal horns. Parasympathetic preangionic neurons send axons through the ventral roots to peripheral ganglia of the pelvic plexus via the pelvic nerve.

Some of the sacral interneurons also send ascending projections to the brain. The dorsal commissure, superficial dorsal horn and sacral parasympathetic nucleus 95 all contain interneurons with rostral projections that are activated during stimulation of the bladder and urethra. These interneurons are the site of origin of ascending pathways 96 that project to structures in the brainstem via spinal paths that include the dorso-lateral funiculus.

The periaqueductal gray (PAG) 97 and pontine micturition center (PMC) 98 are two regions of the brainstem that are central to the control of urine storage and voiding. The ventrolateral portion of the PAG receives afferent input 96 that is derived from the bladder and urethra afferents. As shown in FIG. 8, the PAG also communicates with other parts of the brain, as has been revealed by functional imaging studies during micturition. The hypothalamus, insula, dorsal anterior cingulate and lateral prefrontal cortex are involved in the learned, voluntary control of micturition. The medial prefrontal cortex exerts a tonic inhibition of the periaqueductal gray 97. Some such communications are primarily unidirectional (shown with arrowheads), but most are possibly bidirectional (connections shown without arrowheads). For example, some ascending afferent projections also terminate in the medial parabrachial nucleus (PBN in FIG. 8). The PBN relays the afferent signal to the insula via the thalamus, which in turn connects to the PAG 97. The PAG 97 then sends input to the PMC 98, with additional input from the hypothalamus. The PMC 98 sends descending projections 99 to the spinal cord (80 and 90) via the lateral funiculus [DASGUPTA R, Kavia R B, Fowler C J. Cerebral mechanisms and voiding function. BJU Int 99(4, 2007):731-4].

In its most basic conception, control of urination (micturition) and bladder filling (continence) are controlled by the nervous system as follows. The bladder and internal urethral sphincter receive sympathetic innervation from the hypogastric nerve and parasympathetic innervation from the pelvic nerve. The external urethral sphincter receives somatic innervation from the pudendal nerve. When the bladder is filling, (1) sympathetic nerves with alpha adrenergic receptors constrict the internal sphincter, and sympathetic nerves with beta adrenergic receptors relax the detrusor muscle of the bladder; (2) somatic nerves with nicotinic receptors constrict the external urethral sphincter; and (3) parasympathetic nerves to the bladder are relatively inactive. During urination, the reverse occurs: (1) parasympathetic nerves with muscarinic receptors (M3) cause the bladder's detrusor muscle to contract, and (2) the sympathetic and somatic nerves to the bladder and urethra are relatively inactive, allowing the internal and external urethral sphincters to relax to their open state, thereby allowing the urine to pass through the urethra.

The voluntary act of urination (as well as the voluntary suppression of urination urge), is controlled by the pontine micturition center (PMC 98) as follows. The periaqueductal region (PAG 97) in the midbrain receives afferent bladder and urethral signals from the pelvic, hypogastric, and pudendal nerves via the spinal cord, processes that information with input from other centers of the brain, including higher volitional centers, then activates the PMC 98 according to whether there is a perceived need to urinate. To initiate urination, the M region of the PMC 98 sends signals down the spinal cord to parasympathetic motoneurons 95 causing contraction of the bladder detrusor muscle 809. The M region of the PMC 98 also inhibits the pudendal nerve (at its origin in the nucleus of Onuf 94), causing external sphincter relaxation, and it inhibits thoracolumbar preganglionic sympathetic neurons that in turn exert their control via the hypogastric nerve. When urination is complete, the M region of the PMC 98 becomes relatively silent, and the previously relatively silent L region of the PMC activates the nucleus of Onuf 94, causing the external sphincter 806 to constrict. As the M region of the PMC becomes relatively silent, contraction of the detrusor muscle 809 comes to an end, and the ensuing relative uninhibition of the thoracolumbar preganglionic sympathetic neurons results in relaxation of the detrusor and constriction of the internal urethral sphincter 805.

The control of bladder filling and micturition is in reality much more elaborate than what was summarized in the previous two paragraphs. Viewed at the level of the whole bladder, normal detrusor activity is a sacral balance under suprasacral influences of the sympathetic and parasympathetic nervous systems, as influenced by the L and M regions of the PMC, respectively. Most of the time, during the filling phase, sympathetic activity is dominant. When the parasympathetic activity becomes dominant, the detrusor contracts and the bladder empties. However, it should be understood that sympathetic/parasympathetic balance may also be important within small individual segments of the detrusor, such that during the filling phase, small individual segments are contracting then relaxing (oscillating in tension), as described below.

Furthermore, there are multiple individual reflex pathways that may contribute to the overall control of continence and micturition, including voluntary pathways that involve learned supraspinal influences and involuntary pathways that involve primarily the spinal cord. Important reflexes are the guarding reflexes, the bladder loop reflexes (which promotes filling) and bladder-to-bladder and bladder-to-urethra reflexes (which promote micturition). The guarding reflex prevents the loss of urine during coughing and mechanical stresses during exercise. The bladder loop reflex activates pudendal efferents that cause the external bladder sphincter to close. During the filling that is sensed by bladder afferents, activity of a sphincter myogram increases, reflecting increased reflex pudendal nerve firing and increased sphincter resistance (bladder to sphincter reflex). Contraction of the external urethral sphincter, and possibly other pelvic floor striated muscle, stimulate firing in muscle proprioceptive afferents, which then activate central inhibitory mechanisms to inhibit micturition, suppressing detrusor contraction (sphincter to bladder reflex). As a result of this sphincter to bladder reflex, deliberate, voluntary contraction of the external urethral sphincter may also suppress detrusor contraction.

The bladder-to-bladder reflex causes the detrusor to contract continuously throughout urination, and the bladder-to-urethra reflex relaxes the urethra to permit urine to flow during the urination. Relaxation of the urethral smooth muscle during micturition is mediated by bladder afferents that activate a parasympathetic pathway to the urethra that triggers the release of nitric oxide (bladder to urethra reflex). Urine flow or stimulation of the urethra excites afferent nerves that facilitate reflex bladder contractions (urethra to bladder reflex). The filling and micturition reflexes are antagonistic to one another, so these reflexes must mutually inhibit one another, depending on whether filling or micturition is occurring, and different neurotransmitters are involved in the different reflexes [GARRY R C, Roberts T D M, Todd J K. Reflexes involving the external urethral sphincter in the cat. J. Physiol. 149 (1959):653-65; DE GROAT W C. Integrative control of the lower urinary tract: preclinical perspective. Br J Pharmacol. 147(Suppl 2, 2006):525-40; PARK J M, Bloom D A, McGuire E J. The guarding reflex revisited. Br J. Urol. 80(6, 1997):940-5; Naoki YOSHIMURA and Michael B. Chancellor. Physiology and pharmacology of the bladder and urethra. Chapter 56 in Campbell-Walsh Urology, 9th ed., A J Wein, L R Kavoussi, A C Novick, A W Partin and C A Peters, eds. Philadelphia, Pa.: Saunders Elsevier; 2007. pp 1922-1972; KINDER M V, Bastiaanssen E H, Janknegt R A, Marani E. Neuronal circuitry of the lower urinary tract; central and peripheral neuronal control of the micturition cycle. Anat Embryol (Berl). 1995 September; 192(3):195-209; CHAI T C, Steers W D. Neurophysiology of micturition and continence. Urol Clin North Am. 23(2, 1996): 221-36; ROBERTS M M. Neurophysiology in neurourology. Muscle Nerve. 38(1, 2008): 815-36; DE GROAT W C, Yoshimura N. Pharmacology of the lower urinary tract. Annu Rev Pharmacol Toxicol. 41 (2001): 691-721; ANDERSSON K E, Wein A J. Pharmacology of the lower urinary tract: basis for current and future treatments of urinary incontinence. Pharmacol Rev. 56(4, 2004):581-631].

Overactive bladder and urge incontinence may be explained in part as disturbance to or within the normal physiology described above. It is convenient to distinguish four types of overactive bladder. (1) The patient has overactive bladder symptoms, but no involuntary detrusor contractions are sensed before an incontinence event. (2) The patient has involuntary detrusor contractions but can contract the external sphincter and abort the contraction (using the filling urethra-to-bladder reflex described above). (3) The patient has involuntary detrusor contractions and can briefly contract the external sphincter, but it fatigues and detrusor contraction is not aborted (failed filling urethra-to-bladder reflex). (4) The patient has involuntary detrusor contractions and cannot contract the external sphincter, leading to an involuntary urination.

Only the first of these types of overactive bladder/incontinence does not involve multiple involuntary detrusor contractions. The first type may have an urethrogenic origin, in which a single, terminal bladder contraction is triggered by urine entering the urethra at an inappropriate time. This mechanism may explain stress-induced involuntary detrusor contraction that is triggered by coughing or exercise. Urinary urgency and frequency for this type may also be caused by excessive urine production (polyuria) that is in turn caused by diabetes or excessive fluid drinking (polydipsia) or medications that affect diuresis. The urgency and frequency may also be caused by a low bladder compliance, in which there is a high incremental rise in bladder pressure with filling, due to abnormal elastic and viscoelastic properties of the bladder.

The remaining types of overactive bladder involve multiple involuntary detrusor contractions, so most theories for the cause of overactive bladder focus their explanation on the origin of the involuntary contractions. The most well known theories are the following four, which are not necessarily mutually exclusive. (1) The myogenic theory attributes detrusor instability to changes in the bladder's structure, particularly its musculature. This may be due to obstruction, often caused in men by a benign hyperplastic prostate and in women by pelvic organ prolapse, a diverticulum, and primary bladder neck obstruction, as well as strictures, bladder stones, a foreign body, or a bladder tumor in both men and women. The prolonged obstruction results in weakened detrusor muscle, compensatory muscle hypertrophy, and reduced functional innervations, all of which predispose to involuntary contractions. The myogenic theory also accounts for low bladder compliance in terms of abnormally high detrusor muscle tone. (2) The neurogenic theory attributes detrusor instability to changes in the neural pathways that control the bladder and urethra, particularly pathways in the brain. The changes may be due to spinal cord injury or tumor, multiple sclerosis, Parkinson's disease, stroke, hydrocephalus, a brain tumor, traumatic brain injury, myelodysplasia, transverse myelitis and other neurological conditions, or they may be idiopathic, for example, wherein normally silent bladder C-fiber afferents generate new reflexes or unmask previously silent primitive reflexes that are present before a child learns to control voiding voluntarily. (3) The afferent theory attributes detrusor instability to increased afferent signaling from the bladder, including the urothelium, leading to excessive afferent noise that the brain has difficulty processing, or to increased awareness of filling. The increased afferent signaling may be due to inflammation (e.g., interstitial cystitis) or bladder infection that reduces the threshold for bladder afferents, thereby inducing bladder hyperactivity. (4) The integrative or autonomous theory attributes detrusor instability to abnormal synchronization and imbalanced excitation/inhibition of contractile modules within the detrusor, those modules containing intramural ganglia and interstitial cells. Methods according to the present invention are most closely related to this fourth theory, although the disclosed methods introduce new concepts to it [HENDERSON E, Drake M. Overactive bladder. Maturitas. 2010 66(3, 2010):257-62; En MENG. Recent research advances in the pathophysiology of overactive bladder. Incont Pelvic Floor Dysfunct 3(Suppl 1, 2009): 5-7; BRADING A F. A myogenic basis for the overactive bladder. Urology 50(6A Suppl, 1997):57-67; KANAI A and Andersson K E. Bladder Afferent Signaling: Recent Findings. J Urol 183(4, 2010):1288-95; DE GROAT W C. A neurologic basis for the overactive bladder. Urology 50(6A Suppl, 1997):36-52; discussion 53-6; Naoki YOSHIMURA and Michael B. Chancellor. Physiology and pharmacology of the bladder and urethra. Chapter 56 in Campbell-Walsh Urology, 9th ed., A J Wein, L R Kavoussi, A C Novick, A W Partin and C A Peters, eds. Philadelphia, Pa.: Saunders Elsevier; 2007. pp 1922-1972; Marcus John DRAKE. The Integrative Physiology of the Bladder. Ann R Coll Surg Engl. 89(6, 2007): 580-585; DRAKE M J, Mills I W, Gillespie J I. Model of peripheral autonomous modules and a myovesical plexus in normal and overactive bladder function. Lancet 358(9279, 2001):401-3; STEERS W D. Pathophysiology of overactive bladder and urge urinary incontinence. Rev Urol. 4 (Supp) 4, 2002):S7-S18; Karl-Erik ANDERSSON. Storage and voiding symptoms: pathophysiologic aspects. Urology 62 (5, Supp. 2, 2003): 3-10; RAHN D D, Roshanravan S M. Pathophysiology of urinary incontinence, voiding dysfunction, and overactive bladder. Obstet Gynecol Clin North Am. 36(3, 2009):463-74].

The mechanism of neuromodulation to treat bladder dysfunction, including neuromodulation through stimulation of the posterior tibial nerve, may also be considered in view of the physiology that was summarized in connection with FIGS. 7 and 8 and in view of the above-mentioned theories about the mechanisms of overactive bladder and incontinence. Little is known about the physiological mechanism of tibial nerve stimulation, and much of what is reported about neuromodulation to treat bladder dysfunction is concerned with sacral nerve stimulation neuromodulation. LENG and CHANCELLOR note that the mechanism of sacral nerve stimulation is obscured by the fact that it can be used to treat not only urinary urge incontinence (a filling disorder), but also seemingly disparate disorders such as dysfunctional voiding and urinary retention (i.e., a voiding disorder, such as dyssynergic action between the detrusor and the external sphincter). They suggest that sacral nerve stimulation inhibits overactive bladder by stimulating afferent neural pathways that (1) inhibit sacral interneuronal transmission and/or (2) directly inhibit bladder preganglionic neurons of the efferent limb of the micturition reflex circuit. The source of the afferent input is said to be somatic, visceral, or both: sphincter muscles, distal colon, rectum, anal canal, vagina, uterine cervix, and cutaneous innervation from the perineum. They suggest that pudendal afferents are the most important and that of the two suggested mechanisms, (1) is the more likely because it would block the transfer of signaling input from the bladder to the pontine micturition center, preventing involuntary micturition, but not suppress voluntary voiding. With regard to the converse disorders of urinary retention and dysfunctional voiding, they suggest that sacral nerve stimulation inhibits guarding reflexes, by (1) direct inhibition of bladder preganglionic neurons and/or (2) inhibition of interneuronal transmission in the afferent limb of the micturition reflex. They interpret tibial nerve stimulation as the use of that nerve as the source of afferent input, with the same general mechanism as stimulation of the rectum, vagina, perineum, etc., wherein the stimulation blocks the processing of visceral afferent signals being delivered to the same region of the spinal cord [LENG W W, Chancellor M B. How sacral nerve stimulation neuromodulation works. Urol Clin North Am. 32(1, 2005): 11-8].

VASAVADA and RACKLEY, YOSHIMURA and CHANCELLOR, and ELKELINI et al. suggest much the same mechanisms. VAN DER PAL et al. also suggest these mechanisms, but add that stress incontinence may be treated by sacral nerve stimulation because it produces pelvic floor muscle and external sphincter hypertrophy. AMEND et al., summarizing the consensus of experts, say that "we are still too distant from the understanding of sacral neuromodulation," but indicate that there are differences between the acute and chronic effects of sacral nerve stimulation and emphasize the role of suprapontine centers in the neural pathways that control bladder function. FINAZZI-AGRO et al. as well as APOSTOLIDIS suggest that plastic reorganization of cortical networks triggered by peripheral neuromodulation is a mechanism of action of sacral nerve stimulation and PTNS. Because PINS is administered intermittently, but sacral nerve stimulation is ordinarily applied continuously, PTNS is said to be advantageous in that intermittent stimulation produces more long-lasting effects through such plastic reorganization [Sandip P. VASAVADA and Raymond R. Rackley. Electrical stimulation for storage and emptying disorders. Chapter 64 in Campbell-Walsh Urology, 9th ed., A J Wein, L R Kavoussi, A C Novick, A W Partin and C A Peters, eds. Philadelphia, Pa.: Saunders Elsevier; 2007. pp 2147-2167; Naoki YOSHIMURA and Michael B. Chancellor. Physiology and pharmacology of the bladder and urethra. Chapter 56 in Campbell-Walsh Urology, 9th ed., A J Wein, L R Kavoussi, A C Novick, A W Partin and C A Peters, eds. Philadelphia, Pa.: Saunders Elsevier; 2007. pp 1922-1972; ELKELINI M S, Abuzgaya A, Hassouna M M. Mechanisms of action of sacral neuromodulation. Int Urogynecol J. 21 (Suppl 2, 2010): S439-46; VAN DER PAL F, Heesakkers J P, Bemelmans B L. Current opinion on the working mechanisms of neuromodulation in the treatment of lower urinary tract dysfunction. Curr Opin Urol. 16(4, 2006):261-7; AMEND B, Matzel K E, Abrams P, de Groat W C, Sievert K D. How does neuromodulation work. Neurourol Urodyn. 30(5, 2011):762-5; FINAZZI-AGRO E, Rocchi C, Pachatz C, Petta F, Spera E, Mori F, Sciobica F, Marfia G A. Percutaneous tibial nerve stimulation produces effects on brain activity: study on the modifications of the long latency somatosensory evoked potentials. Neurourol Urodyn. 28(4, 2009): 320-4; APOSTOLIDIS A. Neuromodulation for intractable OAB. Neurourol Urodyn. 2011 June; 30(5):766-70].

In an animal model, TAI et al showed that stimulation of the tibial nerve for 3 to 5 minutes inhibits bladder contractions and that the inhibition persists for up to an hour after stimulation ceases, the expected duration of which is a function of the stimulation voltage. The stimulation voltages that were investigated were two to four times more than those needed to induce toe movement. Stimulation for thirty minutes resulted in an inhibition of contraction for up to two hours. During the inhibition that followed a stimulation, further stimulation increases the length of the inhibition, but this additional inhibition is a function of the stimulation frequency. The mechanism of tibial nerve stimulation was found to be different than pudendal nerve stimulation, because with pudendal nerve stimulation, bladder inhibition occurs at low frequencies and bladder contraction is excited at higher frequencies. Furthermore, pudendal nerve stimulation does not result in persistent inhibition of bladder contraction. TAI et al suggest that tibial nerve stimulation affects bladder reflexes by either direct modulation of the pontine micturition center or the suppression of afferent input to that center, with a role played by the thalamus, at which extensive viscero-somatic signals converge [TAI C, Shen B, Chen M, Wang J, Roppolo J R, de Groat W C. Prolonged poststimulation inhibition of bladder activity induced by tibial nerve stimulation in cats. Am J Physiol Renal Physiol. 300(2, 2011):F385-92].

Overactive bladder represents a disruption in the storage function of the lower urinary tract, so methods according to the present invention begin with a description of the storage phase. The present invention discloses mechanisms for treating bladder dysfunction with posterior tibial nerve stimulation that are different from those reported in the publications cited above. In particular, whereas the previous methods consider the bladder detrusor muscle to be a homogeneous entity that either contracts during micturition or does not contract during filling, and that is acted on uniformly by neural influences, methods according to the present invention also consider distinct contractions within localized regions of the bladder wall. Thus, according to the present invention, neurostimulation mechanisms may also make use of the integrative or autonomous theory of overactive bladder, not just the neurogenic or afferent theories that are invoked in the publications cited above in connection with proposed mechanisms of sacral and tibial nerve stimulation.

There are actually two different contractile phenomena in bladder detrusor muscle, one being spontaneous, multifocal, localized, rhythmic activity exhibited during the filling phase (with which the present invention is primarily concerned), and the other being the voiding contraction during the voiding phase (with which the literature on purported mechanisms for sacral or tibal neuromodulation has been concerned, and which a special case according to the present invention). Thus, the filling bladder of many species, including man, is rhythmically active, even within small muscular segments of the bladder wall. When the bladder is filling with urine, travelling waves of contraction and localized stretches of the bladder wall can be measured by cystometry and micromotion detectors, and imaged using voltage-sensitive fluorescent dyes. Such spontaneous, phasic, localized bladder wall movement can be large, even though there may be little accompanying average pressure change in the bladder lumen during filling, and even though an individual may not always sense that the movements are occurring. These small localized movements of detrusor muscle may be related to the continuous formation of an optimal (e.g., minimum surface area) irregular bladder shape during filling, mediated by pacemaker cells (interstitial cells, analogous to an interstitial cell of Cajal in the gastrointestinal tract) that are located throughout the bladder wall [J. J. GILLESPIE. The autonomous bladder: a view of the origin of bladder overactivity and sensory urge. BJU Int 93(4, 2004):478-83; DRAKE M J, Harvey I J, Gillespie J I, Van Duyl W A. Localized contractions in the normal human bladder and in urinary urgency. BJU Int. 95(7, 2005):1002-5; LAGOU M, Gillespie J, Kirkwood T, Harvey I, Drake M J, Muscarinic stimulation of the mouse isolated whole bladder: physiological responses in young and ageing mice. Auton Autacoid Pharmacol. 26(3, 2006):253-60; KANAI A, Roppolo J, Ikeda Y, Zabbarova I, Tai C, Birder L, Griffiths D, de Groat W, Fry C. Origin of spontaneous activity in neonatal and adult rat bladders and its enhancement by stretch and muscarinic agonists. Am J Physiol Renal Physiol 292(3, 2007):F1065-72; COLLINS C, Klausner A P, Herrick B, Koo H P, Miner A S, Henderson S C, Ratz P H. Potential for control of detrusor smooth muscle spontaneous rhythmic contraction by cyclooxygenase products released by interstitial cells of Cajal. J Cell Mol Med 13(9B, 2009):3236-50].

The localized bladder contractions may also be functionally related to spontaneous peristaltic movements of the renal pelvis and ureter that propel urine to the bladder, which are also mediated by pacemaker cells [CONSTANTINOU C E, Yamaguchi O. Multiple-coupled pacemaker system in renal pelvis of the unicalyceal kidney. Am J. Physiol. 241(5, 1981): R412-8; LANG R J, Davidson M E, Exintaris B. Pyeloureteral motility and ureteral peristalsis: essential role of sensory nerves and endogenous prostaglandins. Exp Physiol. 87(2, 2002):129-46; WEISS R M, Tamarkin F J, Wheeler M A. Pacemaker activity in the upper urinary tract. J Smooth Muscle Res. 42(4, 2006):103-15].

The amplitude and frequency of this localized rhythmic bladder activity during filling is increased by muscarinic or nicotinic agonists, so the local contractions and stretches are not entirely myogenic in origin. Furthermore, because nicotinic agonists are effective in increasing their amplitude, the localized contractions are not entirely due to the parasympathetic mechanisms that are thought to underlie contraction during bladder voiding. Thus, filling and voiding contractions of the detrusor muscle are at least partly under different control by the nervous system. Mechanical fluctuations within any given small segment of the detrusor muscle (a so-called module) will affect rhythmicity of neighboring smooth muscle segments, at a minimum through the mechanical connection of the neighboring muscle segments within the wall of the bladder. Similarly, the afferent nerves from these fluctuating segments of bladder muscle will affect the behavior of connections to afferent nerves from other such muscle segments, at a minimum through communication of those nerves within segments of the spinal cord and brainstem. Thus, the detrusor smooth muscle of the filling bladder, as well as its afferent nerves and their connections, may be regarded as a set of semi-autonomous oscillators, coupled to one another.

Local mechanical oscillations of the bladder would damp themselves out through friction, were they not sustained by a source of metabolic energy, i.e., the equation describing the oscillation will generally be non-conservative. Furthermore, because the velocities of displacement of muscle segments relative to their average or resting position are generally not linearly proportional to the displacements themselves, because the period of oscillation may be a function of the oscillation amplitude rather than a simple constant, and because the tension and compression that segments exert upon one another are likewise generally more complicated than a simple spring constant, then equations that characterize the bladder's oscillators and their interactions must generally be non-linear.

The properties of such non-linear oscillators are currently understood through the analysis of non-linear differential equation prototypes, such as Van der Pol's equation, $$\frac{d^2x}{dt^2} - m(1-x^2)\frac{dx}{dt} + x = 0,$$

where x is the displacement and m is a damping parameter. This much-studied equation describes self-sustaining oscillations in the displacement x that are qualitatively different than those exhibited by a linear, harmonic oscillator. A network of coupled oscillators is constructed by making the displacement of one oscillator be a function of one or more of the other oscillators' displacements, i.e., by coupling each oscillator to other oscillators. Other well-studied non-linear oscillators include FitzHugh-Nagumo (which is a simplified version of the Hodgkin-Huxley model, for which Van der Pol's oscillator is a special case), Morris-Lecar, Ellias-Grossberg, and Stuart-Landau.

Although the detailed oscillations described by such prototypical equations are dependent on the detailed form of the equations and their initial conditions, the qualitative behaviors of such non-linear coupled oscillator equations may often be understood independently of the particular form of the non-linear equation. For example, it is well understood in general that non-linear oscillators, including a set of coupled non-linear oscillators, may exhibit qualitatively different behaviors when the parameters of their equations lie within certain bounds. When graphs are drawn showing the value of one parameter on one axis, and the value of another parameter on another axis, regions of this parameter space may be circumscribed to show what sets of parameter values correspond to each type of qualitatively different dynamics, i.e, a phase diagram. Examples of such phase diagrams are given by MATTHEWS and STROGATZ, that circumscribe different regions of phase space having qualitatively different dynamics, and which are also described below in connection with FIG. 9 [Paul C. MATTHEWS and Steven H. Strogatz. Phase diagram for the collective behavior of limit-cycle oscillators. Phys. Rev. Lett. 65 (1990): 1701-1704].

In the case of the Van der Pol oscillator that was mentioned above, the displacement x undergoes a sustained oscillation, known as a limit cycle, when the parameter m is greater than zero. But when the parameter m is equal to zero, the equation describes a simple harmonic oscillator, and when m is less than or equal to zero, there may be "negative resistance". Van der Pol discovered that when his oscillator was driven (by replacing the zero on the right hand side of his equation with a sinusoidal driving function), then depending on the range of values for m, the oscillator may have a period that locks to p/q of the driving period, where p and q are integers. He also found already in 1927 that when the parameter m lies within another range, the oscillator exhibits irregular, non-periodic displacement, which is today known as deterministic chaos.

When dealing with coupled nonlinear oscillators, such as coupled Van der Pol oscillators (each of which can in general have different values of m, and which can have different forms of local or non-local coupling), the two or more oscillators may eventually all oscillate with the same phase or they may prefer to oscillate with unrelated phases, again depending on the range in which the parameter values lie. Chimera states, in which part of the system is phase locked and simultaneously another part of the system exhibits oscillators with unrelated phases, are also possible. When parameters lie within another range, the coupled oscillators may also exhibit amplitude death, in which the oscillators counteract one another's displacements in such a way that they all stop oscillating (i.e., the amplitude is zero for all oscillators, onto make the physiological correspondence, the oscillators exhibit a type of tonic or tetanic contraction). These qualitatively different types of dynamic behavior are influenced by the presence of noise, and they are exhibited by coupled limit cycle oscillators generally, of which the Van der Pol oscillator is only one example [GUEVARA M. R. Bifurcations involving fixed points and limit cycles in biological systems. In: "Nonlinear Dynamics in Physiology and Medicine", edited by Beuter A., Glass L., Mackey M. C., Titcombe M. S. Springer-Verlag, New York, pp. 41-85 (2003); LEE, Wai Shing; Restrepo, Juan G.; Ott, Edward; Antonsen, Thomas M. Dynamics and pattern formation in large systems of spatially-coupled oscillators with finite response times. Chaos 21(2, 2011), pp. 023122-023122-14; Hiroshi KORI and Alexander S. Mikhailov. Entrainment of Randomly Coupled Oscillator Networks by a Pacemaker. Phys. Rev. Lett. 93 (2004), 254101, pp 1-4; M. CISZAK, A. Montina, and F. T. Arecchi. Sharp versus smooth synchronization transition of locally coupled oscillators. Phys. Rev. E 78 (2008), 016202, pp 1-4; Daniel M. ABRAMS and Steven H. Strogatz. Chimera States for Coupled Oscillators. Phys. Rev. Lett. 93 (2004), 174102, pp 1-4; KONISHI K. Experimental evidence foramplitude death induced by dynamic coupling: van der Pol oscillators. Proc. ISCAS (4, 2004) 792-795; Shinji DOI, Yohei Isotani, Ken-ichiro Sugimoto and Sadatoshi Kumagai. Noise-induced critical breakdown of phase lockings in a forced van der Pol oscillator. Physics Letters A 310 (5-6, 2003): 407-414].

Figure 9A:
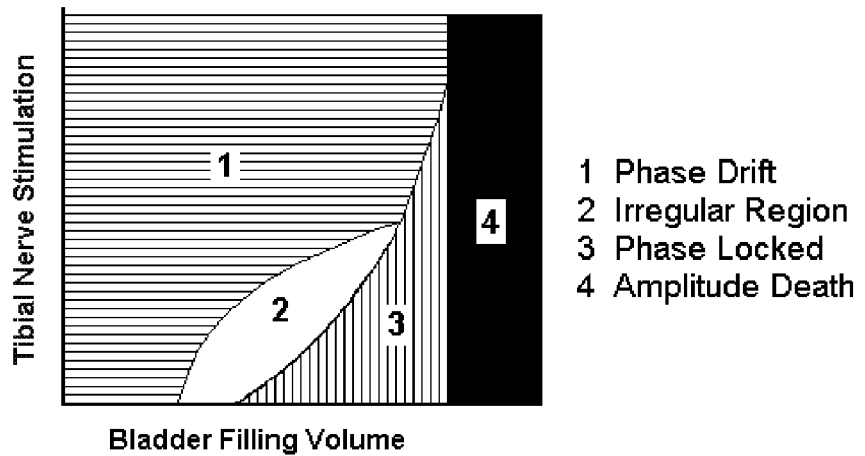
FIG. 9 illustrates a phase diagram according to the present invention, which circumscribes regions where coupled nonlinear oscillators within the wall of the bladder exhibit qualitatively different types of dynamics, as the bladder volume and cumulative magnitude of tibial nerve stimulations are varied.
Figure 9B:
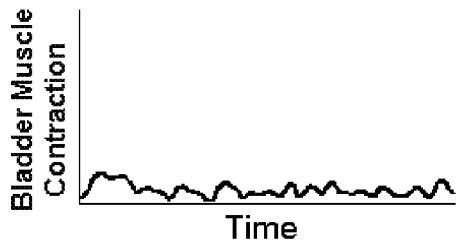
Figure 9B:
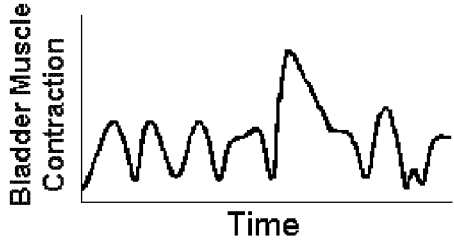
Figure 9B:
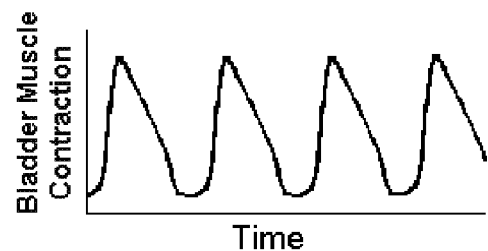
Figure 9B:
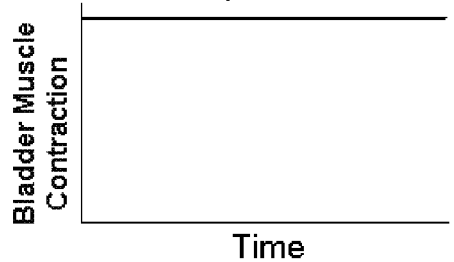

When one or more of the parameters of the set of coupled nonlinear oscillators may be varied under external influences to produce qualitative changes of phase in the system, the parameter is said to be an order parameter. According to the present invention, modules of the bladder wall may be represented mathematically as nonlinear oscillators that are coupled to one another, and an order parameter for the system is the volume of urine in the bladder, as shown in FIG. 9A. Another order parameter is related to the magnitude and duration of tibial nerve stimulation, which will be described below. Consider first only the changes in phase that occur as the bladder volume increases, beginning with the essentially zero volume that obtains after micturition is just finished (or more generally, a postvoid residual volume). Moving along the lower axis in FIG. 9A at increasing volume, the successive phases that are encountered as the bladder filling volume is increased are called successively: phase drift, irregular region, phase locked, and amplitude death. The dynamics of the system in each of those phases is represented in FIG. 9B, in which the average, over multiple detrusor muscle modules, of the bladder's contraction is shown as a function of time. Within the phase drift phase, there are only small fluctuations of contraction amplitude. Within the irregular phase, there are small fluctuations along with occasional irregularly-timed large amplitude contractions. The dynamics are not periodic, but may instead exhibit aperiodic dynamics such as deterministic chaos, Hopf oscillation, quasiperiodicity, and large oscillation [Paul C. MATTHEWS and Steven H. Strogatz. Phase diagram for the collective behavior of limit-cycle oscillators. Phys. Rev. Lett. 65 (1990): 1701-1704; Paul C. MATTHEWS, Renato E. Mirollo, and Steven H. Strogatz. Dynamics of a large system of coupled nonlinear oscillators. Physica D: Nonlinear Phenomena 52 (2-3, 1991): 293-331]. During the phase-locked phase, there are regularly-timed large amplitude contractions. During the amplitude death phase, fluctuations in the amplitude of contractions disappear, such that the contraction would be considered to be tonic.

Continuous ambulatory urodynamics, measuring detrusor contractions and leakage, show that an individual with a unstable detrusor may exhibit the irregularly-timed contraction peaks, with urine leakage whenever the peaks exceed a threshold, as well as the periods in which there are only small fluctuations in detrusor contraction and no urine leakage [BRISTOW S E, Neal D E. Ambulatory urodynamics. Br J. Urol. 77(3, 1996): 333-8]. These correspond to the irregular phase and phase drift phase of FIG. 9, respectively. It is also possible to observe periodic bladder contractions or bladder pressure variations when the bladder is deliberately filled nearly to its capacity [TAI C, Shen B, Chen M, Wang J, Roppolo J R, de Groat W C. Prolonged poststimulation inhibition of bladder activity induced by tibial nerve stimulation in cats. Am J Physiol Renal Physiol 300(2, 2011):F385-92]. These oscillations correspond to the phase locked phase in FIG. 9. The amplitude death phase corresponds to maximum detrusor contraction, as can be estimated, for example, with stop tests [TAN T L, Bergmann M A, Griffiths D, Resnick N M. Which stop test is best? Measuring detrusor contractility in older females. J. Urol. 169(3, 2003): 1023-7].

Micturition is under voluntary control, so that an individual can urinate well before the bladder reaches the phases of sustained oscillations or amplitude death. Thus, as the bladder fills, an individual will have sensations as follows: (1) Possibly a vague sensation of bladder filling that waxes and wanes, and that can be easily ignored; (2) A first desire to void that gets stronger with more bladder filling, that can be mentally ignored only for a short time after the first desire; and (3) A strong desire to void with an uncomfortable sensation [WYNDAELE J J. The normal pattern& perception of bladder filling during cystometry studied in 38 young healthy volunteers. J. Urol. 160(2, 1998): 479-81]. Because of the voluntary nature of micturition, most voids are often therefore not truly urgent [DE WACHTER S, Wyndaele J J Frequency-volume charts: a tool to evaluate bladder sensation. Neurourol Urodyn. 22(7, 2003):638-42; DE WACHTER S, Wyndaele J J. How sudden is a compelling desire to void? An observational cystometric study on the suddenness of this sensation. BJU Int. 101(8, 2008):1000-3]. The situation is described by CHAPPLE et al as follows. As the bladder fills after a void, a normal individual will exhibit a refractory period in which any sensation of filling can be easily ignored, followed by a first desire to void, followed by irregularly-timed periods of increasingly intense feelings of the need to void, which can be aborted at the individual's convenience by voiding. The individual with an overactive bladder may have a shortened refractory period, followed by the irregularly-timed periods of increasingly intense feelings of the need to void, followed by a "warning period" during which there is a sensation of urgency (as in the above-mentioned sensation 3), followed by a voluntary or an incontinent void, depending on sphincter and pelvic floor strength or weakness, the duration of the warning time, access to a toilet, etc. [CHAPPLE C R, Artibani W, Cardozo L D, Castro-Diaz D, Craggs M, Haab F, Khullar V, Versi E. The role of urinary urgency and its measurement in the overactive bladder symptom syndrome: current concepts and future prospects. BJU Int. 95(3, 2005):335-40]. Thus, the phase drift in FIG. 9 may also be considered to be a refractory phase, the irregular phase may be considered to be the time period including the first desire to void and the increasingly intense, but not urgent, need to void, and the phase locked and amplitude death phases correspond to the "warning period" sense of urgency and discomfort. It is understood that the shapes of phase diagrams shown in FIG. 9 will vary from individual to individual, such that for example, an individual with overactive bladder may have a relatively brief phase-drift phase as the bladder fills, or another individual may have a small or non-existent phase locked phase. It is also understood that conscious effort may move an individual from one phase to another, for example, by urinating to reduce the bladder's volume, or by deliberately constricting the external urethral sphincter so as to produce a urethra-to-bladder reflex that suppresses detrusor contraction.

The disclosure above described only the filling bladder's detrusor muscle in terms of coupled non-linear oscillators, and this may be sufficient for individuals who void voluntarily. For individuals who void involuntarily, the involuntary urination can be included in the invention's equations as well. Thus, the description in terms of non-linear oscillators can be expanded to describe other components of the lower urinary tract. One component is the trigone (807 in FIG. 8), which also contains pacemaker cells that can cause spontaneous oscillation [ROOSEN A, Wu C, Sui G, Chowdhury R A, Patel P M, Fry C H. Characteristics of spontaneous activity in the bladder trigone. Eur Urol. 56(2, 2009):346-53]. Another component is the urethra, for which it is a well-established physical principle that collapsible tubes undergo flow-induced oscillation and even deterministic chaos [BERTRAM C. Flow phenomena in floppy tubes. Contemporary Physics 45 (1, 2004): 45-60; BERTRAM C D, Timmer J, Müller T G, Maiwald T, Winterhalder M, Voss H U. Aperiodic flow-induced oscillations of collapsible tubes: a critical reappraisal. Med Eng Phys. 26(3, 2004):201-14].

Oscillations in the urethra can also involve oscillatory contraction of muscle, including sphincter muscle. Such oscillations in the rodent urethra muscle are well known. Urethral oscillations in humans are less well known, but have been reported, and they are likely to result in at least small amplitude flow oscillation superimposed upon a continuous urine stream. Such oscillations have also been documented in larger animals, e.g., cats in connection with the mechanism of coordination between bladder and urethral function. The oscillations may originate with urethral pacemaker cells that have been identified. However unlike the detrusor, as the bladder begins to fill, urethral oscillators cause tonic rather than phasic urethral contraction. When considered as a collection of coupled oscillators, the urethral oscillators may therefore have a phase diagram that is the reverse of the one shown in FIG. 9 for detrusor muscle. That is to say, with low bladder volume, they may exhibit amplitude death (tonic contraction), and as the bladder fills, they may give rise to phase-locked or irregular fluctuations, until ultimately phase drift of the oscillators would cause the urethra smooth musculature to largely relax [A F BRADING. Spontaneous activity of lower urinary tract smooth muscles: correlation between ion channels and tissue function. J. Physiol. 570(Pt 1, 2006): 13-22; KULSENG-HANSSEN S. Prevalence and pattern of unstable urethral pressure in one hundred seventy-four gynecologic patients referred for urodynamic investigation. Am J Obstet Gynecol. 146(8, 1983): 895-900; VEREECKEN R L, Das J. Urethral instability: related to stress and/or urge incontinence? J. Urol. 134(4, 1985): 698-701; KULSENG-HANSSEN S, Kristoffersen M. Urethral pressure variations in females with and without neurourological symptoms. Scand J Urol Nephrol Suppl. 114 (1988):48-52; L E FEBER J, van Asselt E. Pudendal nerve stimulation induces urethral contraction and relaxation. Am J. Physiol. 1999 November; 277(5 Pt 2):R1368-75; Derek GRIFFITHS, Gert Holstege, Eddie Dalm, Hans De Wall. Control and coordination of bladder and urethral function in the brainstem of the cat. Neurourology and Urodynamics 9 (1, 1990): 63-82].

Coupling between the activities of the urethral pacemaker cell-oscillators occurs not only through mechanical attachments to one another, but also through control by the nervous system as illustrated in FIG. 8. Thus, detrusor and urethral oscillators are all coupled through the nervous system and its reflexes, and this introduces coupling to oscillators that are not necessarily in proximity to one another, as well as additional non-linearity to the system as a whole [PAPA PETROS P E. Detrusor instability and low compliance may represent different levels of disturbance in peripheral feedback control of the micturition reflex. Neurourol Urodyn. 18(2, 1999):81-91; Peter E PAPA PETROS. The female pelvic floor: function, dysfunction and management according to the integral theory. 3rd ed. Chapter 6: Mapping the Dynamics of Connective Tissue Dysfunction. Dordrecht: Springer, 2010].

According to the present invention, the mechanism of tibial nerve stimulation may be different from that proposed in publications cited above. Those publications interpret tibial nerve stimulation as the use of that nerve as the source of afferent input, with the same general mechanism as stimulation of the distal colon, rectum, anal canal, vagina, uterine cervix, penis, cutaneous innervation from the perineum, etc., wherein the stimulation blocks the processing of visceral afferent signals being delivered to the same region of the spinal cord as the one participating in continence and voiding reflexes. However, the tibial nerve is different in at least one important respect from the nerves innervating those other anatomical locations. The difference is that the tibial nerve participates in walking and other forms of locomotion that are produced by central pattern generators.

A central pattern generator (CPG) is a neural network that generates the rhythm and shapes the motor bursts of motoneurons spontaneously, and also when electrically stimulated or when stimulated with drugs. It is generally assumed that there is at least one set of CPG for each limb and that these CPGs are located in the spinal cord. The CPGs for each limb are connected, such that the spinal cord can generate spontaneous bouts of rhythmic alternating ventral root discharge. However, the commands for initiating and terminating these rhythm generators come from supraspinal neurons. Afferents deliver movement-related information to the spinal and supraspinal levels, which then varies CPG control to meet environmental demands. Thus, experimental tibial nerve stimulation of low power induces a change between flexing and extending a hindlimb, and the afferent signal that is being sent apparently represents a detection of footfall or a similar gait-related event [DUYSENS J, Van de Crommert H W. Neural control of locomotion; The central pattern generator from cats to humans. Gait Posture. 7(2, 1998):131-141; WHELAN P, Bonnot A, O'Donovan M J. Properties of rhythmic activity generated by the isolated spinal cord of the neonatal mouse. J. Neurophysiol. 84(6, 2000):2821-33]. The cerebellum may be important in adapting locomotion in varying environments. It receives information about the state of spinal pattern generating circuits through ventral spincerebellar pathways and the state of the limbs bilaterally through doral spinocerebellar pathways, allowing it to compare intended leg movements with actual leg movements and elicit corrections.

It has long been known that distention of the bladder may depress or enhance somatic reflexes in the hindlimbs of cats [M. H. EVANS and A. McPherson. The effects of distention of the bladder on somatic reflexes in the cat. J. Physiol. 146 (1959): 438-458]. Thus, bladder distention induces walking movements in spinal cats. Conversely, spasm in the limbs of patients with myelitis induces bladder contractions [Gregory BOCK and Julie Whelan, eds. CIBA Foundation Symposium 151. Neurobiology of Incontinence. (1990) New York: Wiley, p. 107]. Stimulation of the cut central ends of the posterior tibial nerve inhibit bladder contractions. In paraplegic patients, flexion movements of the feet are caused by bladder distension, and those movements can be consciously antagonized or prevented by the patient to delay micturition [Angus McPHERSON. The effects of somatic stimuli on the bladder in the cat. J. Physiol. 185 (1966): 185-196]. Therefore, the bladder's oscillators and the oscillators for locomotion are naturally coupled, if not in the spinal cord, then supraspinally, for example, in the cerebellum (FIG. 8). Consequently, according to the present invention, one objective of tibial nerve stimulation is to inhibit a central pattern generator that generates oscillatory limb movement, and thereby inhibit bladder contractions.

In an animal model, TAI et al showed that stimulation of the tibial nerve for 3 to 5 minutes inhibits bladder contractions and that the inhibition persists for up to an hour after stimulation ceases, the expected duration of which is a function of the stimulation power. The stimulation intensities that were investigated were two to four times that needed to induce toe movement. Stimulation for thirty minutes resulted in an inhibition of contraction for up to two hours. During the inhibition, further stimulation increases the length of the inhibition, but this additional inhibition is a function of the stimulation frequency. TAI et al suggest that tibial nerve stimulation affects bladder reflexes by either direct modulation of the pontine micturition center or the suppression of afferent input to that center, with a role played by the thalamus [TAI C, Shen B, Chen M, Wang J, Roppolo J R, de Groat W C. Prolonged poststimulation inhibition of bladder activity induced by tibial nerve stimulation in cats. Am J Physiol Renal Physiol. 300(2, 2011):F385-92]. However, according to foregoing disclosure, modulation of the pontine micturition center by tibial nerve stimulation may instead or in addition be via a pathway involving the cerebellum (FIG. 8). Furthermore, because the spinal cord can generate spontaneous bouts of rhythmic alternating ventral root discharge to drive locomotion, according to the present invention, the effects of tibial nerve stimulation may be enhanced by performing tibial stimulation bilaterally, wherein stimulation to one leg may be delayed relative to stimulation of the other leg, in order to antagonize the rhythmic alternating ventral root discharge that is associated with bipedal locomotion.

Turning now to the phase diagram in FIG. 9A, note that the vertical axis is labeled as "Tibial Nerve Stimulation." According to the above-mentioned experiment, the effectiveness of tibial nerve stimulation in inhibiting bladder contraction is a function of the stimulation voltage, the duration of the stimulation, and if stimulation has ceased, the time since cessation of the last stimulation. Accordingly, the numerical value of the accumulated "Tibial Nerve stimulation" with a particular waveform is denoted as S(t) and may for present purposes be represented as one that increases at a rate proportional to the stimulation voltage V and decays with a time constant $\tau_P$, such that after prolonged stimulation, the accumulated stimulation effectiveness will saturate at a value equal to the product of V and $\tau_P$. Thus, if $T_P$ is the duration of a stimulus pulse, then for time $t<T_P$, $S(t)=V\tau_P[1-\exp(-t/\tau_P)]+S_0\exp(-t/\tau_P)$, and for $t>T_P$, $S(t)=S(T_P)\exp(-[t-T_P]/\tau_P)$, where the time t is measured from the start of a pulse, $S_0$ is the value of S when $t=0$, and the stimulation voltage V may be expressed in units of the value needed to first elicit toe movement. Then, according to FIG. 9, as stimuli to the tibial nerve are applied, it is possible for the system to switch from one phase of detrusor contraction to another, even if the bladder had a constant volume.

In terms of FIG. 9A, in the experiments of TAI et al, the system began in the phase locked phase, was simulated up and out of that phase into the phase drift phase, and after stimulus ceased, the system decayed back into the phase locked phase. The situation with any given individual would depend upon that individual's particular phase diagram, but if the individual has a diagram like that shown in FIG. 9A, then the best strategy for preventing unwanted detrusor contractions would be to stimulate the tibial nerve for as long as possible with as high a voltage as possible, so as to drive the system out of its current phase and into the phase drift phase (or maintain it in the drift phase) for as long as possible, until filling of the bladder eventually forces the detrusor into tonic contraction and voiding (the amplitude death phase). However, that strategy may not be practical, because at some voltage, the stimulus would be too painful or cause unwanted muscle twitches, and the stimulation is not intended to be continuous, as could have been the case with an implanted stimulator. Furthermore, because of decay of the accumulated stimulus effect, additional stimulation would be ineffective as the effect saturates at a level determined by the stimulation voltage V and decay time constant $\tau_P$.

One aspect of the disclosed tibial nerve stimulation method is that it is a method for explaining and teaching the origin of thresholds and qualitatively different dynamical behaviors of the bladder, which heretofore could be regarded only as empirical facts. For example, according to the present invention, the fact that the detrusor can undergo periodic coordinated contractions, as the bladder volume reaches a threshold value and tibial nerve stimulation effects have decayed or been limited, is a mathematically derived consequence of the existence of interacting pacemaker cells and their associated contractile modules within the bladder. This prediction emerges from the disclosed discovery that, mathematically speaking, the bladder modules behave as coupled nonlinear oscillators. As another example, according to the present invention, the erratic detrusor contractions that are experienced by the patient with overactive bladder may be to some extent mathematically predictable and are therefore not truly erratic, as in the irregular region of FIG. 9 when the system may exhibit a deterministic chaos dynamics.

Another aspect of the disclosed tibial nerve stimulation method is that its implementation may aid in evaluating whether an individual is a suitable candidate for the stimulation, in the selection of parameters for the stimulation protocol, and in evaluating the extent to which the stimulation has had an effect. Parameters for the stimulation protocol include not only waveform parameters such as those shown in FIG. 2, but also the number and duration of stimulation episodes during a single stimulation session, the time interval between those episodes, and when the stimulation episodes begin relative to the last micturition. Implementation of these evaluation aids requires a mathematical embodiment of the invention. For example, in one simple embodiment, the bladder oscillators are represented as coupled Van der Pol oscillators, as in the following equations with two oscillators. Such a representation can be expanded to any number of oscillators by making all oscillators coupled to all other oscillators so as to emphasize neural feedback loops, or only to oscillators in proximity to one another so as to emphasize local mechanical effects, or some intermediate coupling configuration.

$$\frac{d^2 x_1}{dt^2} - m_1(1 - x_1^2)\frac{dx_1}{dt} + x_1 = a(x_2 - x_1) \text{ and}$$

$$\frac{d^2 x_2}{dt^2} - m_2(1 - x_2^2)\frac{dx_2}{dt} + (1 + b)x_2 = a(x_1 - x_2)$$

where t is time, $x_1$ and $x_2$ represent displacements of the first and second bladder oscillators, respectively, relative to their resting positions, m is a damping parameter, $\alpha$ is a coupling parameter, and b is a detuning parameter. In general, $m_1$ and $m_2$ will not be equal, so the natural periods of the oscillators need not be the same, although according to the dynamics, the oscillators can nevertheless entrain one another. Coupling in the example above is linear, although the coupling can also be assumed to be nonlinear by replacing $\alpha(x_1-x_2)$ with $\alpha_1(x_1-x_2)+\alpha_2(x_1-x_2)^2+\ldots$, or by replacing the term $\alpha(x_1-x_2)$ with a more general function of displacements of all of the oscillators. The changing volume of urine in the bladder U may be introduced by letting parameters such as the coupling parameter $\alpha$ be a function of U(t). The tibial nerve stimulation S(t), which was defined above, may also be introduced through the parameters. For example, $\alpha=a_{00}+\alpha_{10}U+\alpha_{01}S+\alpha_{11}US+\alpha_{20}U^2+\alpha_{02}S^2+\ldots$. Functions of the oscillator displacements, such as the average displacement $(x_1+x_2)/2$, may enter the coupling parameter and would also be useful for comparison with measurements. The coupling parameter(s) may also be made to be a function of multiple oscillator values, possibly at a previous time $t-\Delta$, so as to account for the time delay $\Delta$ in neural reflexes between afferent signals and efferent effects that couple oscillators to one another [Paul C. MATTHEWS and Steven H. Strogatz. Phase diagram for the collective behavior of limit-cycle oscillators. Phys. Rev. Lett. 65 (1990): 1701-1704; Frank SCHILDER and Bruce B. Peckham. Computing Arnold Tongue Scenarios. Journal of Computational Physics 220 (2007): 932-951; Abhijit SEN, Ramana Dodla and George L Johnston. Collective dynamics of delay-coupled limit cycle oscillators. PRAMANA (64, 2005): 465-482].

Coupled nonlinear oscillator equations of the type written above may also be used to model the urethra, if incontinence is a major clinical concern for the patient. It is understood that the urethral equations will have different parameter values than the detrusor equations, and in particular, the parametric influence of bladder volume U will be such that the urethra is normally closed when the bladder volume is small. Coupled oscillator equations may also be constructed to represent the pattern generator with which the tibial nerve is connected. Alternatively, an existing dynamical model for a central pattern generator may be used, the phases of which may correspond to gait patterns such as walk, run, two-legged hop, two-legged jump, skip, gallop, asymmetric hop, and one-legged hop [PINTO C M, Golubitsky M. Central pattern generators for bipedal locomotion. J Math Biol. 53(3, 2006): 474-89]. For these more elaborate models, coupling of the subcomponents within the overall model is performed by including oscillator variables from one subcomponent into the coupling term in equations for another subcomponent's oscillators.

Usefulness of this method is dependent on the extent to which the patient is willing to undergo urodynamic measurement to allow estimation of an embodiment of the method's equations' parameters. It is understood that the measurement will consist of a period of baseline monitoring, followed by a period during which the tibial nerve is stimulated using a default stimulation protocol or during which tibial nerve stimulation parameters are varied. The most useful measurements would be ones in which micro-motions of individual bladder segments are measured, so as to be able to estimate parameters for oscillators individually [DRAKE M J, Harvey I J, Gillespie J I, Van Duyl W A. Localized contractions in the normal human bladder and in urinary urgency. BJU Int. 95(7, 2005):1002-5].

More conventional, but less detailed, measurements would involve ambulatory urodynamics [BRISTOW S E, Neal D E. Ambulatory urodynamics. Br J. Urol. 77(3, 1996): 333-8; Ernst S. C. van Waalwijk VAN DOORN, Aswin H. P. Meier, Anton W. Ambergen, Ruud A. Janknegt. Ambulatory urodynamics: extramural testing of the lower and upper urinary tract by Holter monitoring of cystometrogram, uroflowmetry, and renal pelvic pressures. Urologic Clinics of North America 23(3, 1996):*345-371]. In that case, continuous bladder pressure measurements over the course of preferably 24 hours are used as a surrogate for the average oscillator displacement. Alternatively, measurement of intravesical pressure with an external pressure transducer connected to a suprapubic catheter may also be applied in some patients when urethral activity is of no interest. It should be noted that a potential confounding variable in the interpretation of the ambulatory recording of successive detrusor contractions is the voluntary posture and activity of the patient [AL-HAYEK S, Belal M, Abrams P. Does the patient's position influence the detection of detrusor overactivity? Neurourol Urodyn. 27(4, 2008): 279-86]. Thus, it would be useful to include an accelerometer/inclinometer in the ambulatory monitoring equipment to account for the effects of posture and activity. Furthermore, bladder volume is not conventionally measured in such ambulatory techniques, but it can be estimated in real-time by impedance measurement [LIAO W C, Jaw F S. Noninvasive electrical impedance analysis to measure human urinary bladder volume. J Obstet Gynaecol Res. 37(8, 2011):1071-5]. Alternatively, portable ultrasound devices are available to obtain intermittent bladder volume values. Otherwise, bladder volume as a function of time may be estimated from urine output volume measurements after urination, assuming that the urine is being delivered via the ureters to the bladder at a constant rate between voids, or using curve-fitting interpolation of multiple successive urine volumes to estimate a non-constant rate between voids, which would be attributable to the bolus consumption of fluids and substances containing diuretics.

Even if ambulatory urodynamics is not performed, estimates of ranges on parameters in the equations might still be possible if the patient is willing to maintain a log of bladder events that is even more complete than the ones that are now ordinarily requested. Thus, electronic diaries are now available for the patient to record what had been previously recorded only on paper, but the electronic diaries may be expanded to use push buttons to conveniently record in real time things such as a first desire to void; subsequent feelings of the need to void, their urgency, their subsiding, and voluntary suppression of those feelings; times of urination; detailed data concerning fluid intake and urine output (voluntary or involuntary); posture and activity data (e.g. using accelerometers); and when a tibial nerve stimulation protocol is in place, the timing of the stimulation onset, cessation, stimulus voltage, and any sensations such as pain or muscle twitching [QUINN P, Goka J, Richardson H. Assessment of an electronic daily diary in patients with overactive bladder. BJU Int. 91(7, 2003):647-52].

Estimation of parameters of the equations from continuously acquired data may be made using existing methods such as the multiple shooting and recursive (e.g., Kalman filter) approaches [Henning U. VOSS and Jens Timmer. Nonlinear dynamical system identification from uncertain and indirect measurements. International Journal of Bifurcation and Chaos 14(6, 2004):1905-1933], or synchronization methods [HDI ABARBANEL, D R Creveling, and J M Jeanne. Estimation of parameters in nonlinear systems using balanced synchronization. Physical Review E 77 (2008):016208, pp 1-14]. Methods are also available to estimate parameters when only a limited amount of experimental dynamical data are available for the system, for example, when information is only available about the timing of peak events, which in the present context would include the timing of successive detrusor contractions recorded in diaries [Carlo PICCARDI. Parameter estimation for systems with peak-to-peak dynamics. International Journal of Bifurcation and Chaos (IJBC) 18(3, 2008): 745-753].

After parameter estimation, repeated numerical simulation with the coupled-oscillator equations using different stimulation patterns may reveal an optimal treatment strategy, for example, by minimizing the number of detrusor contractions. Thus, by performing different simulations with the equations, the duration and power of the stimulation may be varied; the inter-stimulus period may be varied; the stimulation may be restricted to particular phases of bladder activity (e.g., only the refractory period, or only the period of irregular detrusor contractions or only a period immediately after the first urge to urinate is experienced).

By performing tibial nerve stimulation with the protocol that had been predicted by the simulations to produce the best outcome, then comparing the patient's medical history before and after the stimulation, the degree to which the method has improved the patient's symptoms may then be evaluated. On the other hand, patients for whom the equations' simulations predict that no particular protocol will reduce detrusor instability may also be judged to be poor candidates for tibial nerve stimulation. Because the stimulation sessions may be performed over the course of several months, it is understood that the method may produce changes in the patient's physiological control systems, such that it may be necessary to repeat the parameter estimation and prediction of optimal stimulation protocol that was described above. Changes in the equations' parameters after successive estimations may be used to characterize the effect that tibial stimulation is having on plasticity of the corresponding portions of the nervous system that control the lower urinary tract.

It is also understood that the method may be applied to the design of neuromodulation protocols that do not involve stimulation the tibial nerve. These include the noninvasive and invasive neuromodulation of other nerves, such as invasive sacral neuromodulation. The methods may also be adapted to design treatment protocols that do not involve neuromodulation, for example, treatment of lower urinary tract disorders with drugs. In that case, the equations would have to be supplemented with pharmacodynamic equations, and the tibial nerve stimulation parameters for voltage V and stimulus decay $\tau_P$ would be replaced by a drug concentration and its half-life, respectively.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating a disorder of a lower urinary tract in a patient, the method comprising:
    positioning a device adjacent to a skin surface of the patient;
    generating one or more electrical impulses with the device; and
    transmitting the one or more electrical impulses from the device to selected nerve fibers in the patient;
    wherein the one or more electrical impulses is sufficient to cause the selected nerve fibers to generate action potentials that at least partially relieve a symptom selected from a group of symptoms comprising urgent urination, frequent urination, urge incontinence, urgent urination with incontinence, frequent urination with incontinence, nocturia, ischuria, bladder discomfort, and bladder pain, and
    wherein the one or more electrical impulses is transmitted to the patient in a treatment session having a period from about 3 minutes to about three hours, followed by a period from about three hours to about one week wherein the one or more electrical impulses is not transmitted to the patient, and
    wherein the one or more electrical impulses is transmitted when the bladder of the patient has a bladder filling-volume that is within a predetermined range of volumes,
    wherein the one or more electrical impulses is transmitted transcutaneously through an outer skin surface of the patient to generate an electrical impulse at or near the selected nerve fibers,
    wherein the transmitting is carried out by generating a magnetic field via the device, wherein the magnetic field is exterior to the patient, wherein the magnetic field is sufficient to induce the one or more electrical impulses at or near the selected nerve fibers within the patient.

2. The method of claim 1, wherein an energy source within the device is configured to generate shaped electrical impulses and transmit the shaped electrical impulses to the patient through a conducting medium within the device.

3. The method of claim 1, wherein the transmitting is carried out by transcutaneously passing an electrical current through the outer skin surface of the patient to a target region within the patient.

4. The method of claim 3, further comprising:
    generating an electrical field at or near the device and shaping the electrical field such that the electrical field is sufficient to modulate a nerve at the target region; and
    wherein the electric field is not sufficient to modulate a nerve or a muscle between the outer skin surface and the target region.

5. The method of claim 4, wherein the electric field is not sufficient to produce movement of a skeletal muscle in a limb of the patient.

6. The method of claim 1, wherein at least one of the nerve fibers is at least from about 0.5 cm to about 2 cm below the outer skin surface of the patient.

7. The method of claim 1, wherein the one or more electrical impulses is constrained from modulating one or more nerves in a region between the skin surface and at least one of the selected nerve fibers.

8. The method of claim 1, wherein the selected nerve fibers are associated with a posterior tibial nerve of the patient.

9. The method of claim 1, wherein the selected nerve fibers are associated with both left and right posterior tibial nerves of the patient.

10. The method of claim 9, wherein the one or more electrical impulses is transmitted alternately to the left and right posterior nerves of the patient.

11. The method of claim 1, wherein at least one of the nerve fibers is selected from among:
    tibial nerve, pudendal nerve, sciatic nerve, superior gluteal nerve, lumbo-sacral trunk nerve, inferior gluteal nerve, common fibular nerve, posterior femoral cutaneous nerve, obturator nerve, common peroneal nerve, plantar nerve, sacral nerves S1, S2, S3, or S4, or nerves of the S1, S2, S3, or S4 dermatome, and sacral anterior root nerves.

12. The method of claim 1, wherein the one or more electrical impulses comprise bursts of pulses with a frequency from about 5 bursts per second (Hz) to about 100 bursts per second (Hz).

13. The method of claim 12, wherein each of the bursts contains from about 1 pulse to about 20 pulses.

14. The method of claim 12 wherein the pulses are full sinusoidal waves.

15. The method of claim 12, wherein each of the pulses is from about 50 microseconds to about 1000 microseconds in duration.

16. The method of claim 1, wherein a first power of the one or more electrical impulses is configured to be a predetermined percentage of a second power needed to first produce movement of a skeletal muscle in a limb of the patient.

17. The method of claim 1, wherein the one or more electrical impulses is transmitted preferentially when the patient's bladder-filling is in a phase selected from among: a refractory phase following urination wherein the patient has no desire to urinate; a phase beginning with a first desire to urinate and ending before a strong desire to urinate; and a phase beginning with a strong desire to urinate that cannot be ignored by the patient.

18. A method of treating a disorder of a lower urinary tract in a patient, the method comprising:
    positioning a device adjacent to a skin surface of the patient;
    generating one or more electrical impulses with the device; and
    transmitting the one or more electrical impulses from the device to selected nerve fibers in the patient;
    wherein the one or more electrical impulses is sufficient to cause the selected nerve fibers to generate action potentials that at least partially relieve a symptom selected from a group of symptoms comprising urgent urination, frequent urination, urge incontinence, urgent urination with incontinence, frequent urination with incontinence, nocturia, ischuria, bladder discomfort, and bladder pain, and wherein the one or more electrical impulses is transmitted to the patient in a treatment session having a period from about 3 minutes to about three hours, followed by a period from about three hours to about one week wherein the one or more electrical impulses is not transmitted to the patient, and wherein the one or more electrical impulses is transmitted when the bladder of the patient has a bladder filling-volume that is within a predetermined range of volumes, wherein one or more protocol parameters for a treatment session is selected individually for the patient, wherein the one or more protocol parameters comprising at least one of: a burst frequency, a number of pulses per burst, a duration of a pulse within a burst, a power of electrical impulses, a duration of an impulse-transmission session, a duration of a period during which impulses are not transmitted, a phase or phases of bladder-filling of a patient when electrical impulses are transmitted, and a range of bladder filling-volumes when electrical impulses are transmitted, wherein the one or more protocol parameters is selected via:

performing measurements of bladder and urethra function of the patient;

using said measurements to estimate values of numerical parameters in a set of differential equations that represents modules of the bladder of the patient as coupled non-linear oscillators;

simulating a plurality of potential treatments by solving said differential equations with different protocol parameters; and selecting among said simulations the one having protocol parameters that minimize simulated bladder contractions.

19. A method of treating a disorder of a lower urinary tract in a patient, the method comprising:

positioning a device adjacent to a skin surface of the patient;

generating one or more electrical impulses with the device; and transmitting the one or more electrical impulses from the device to selected nerve fibers in the patient, wherein the one or more electrical impulses is sufficient to cause the selected nerve fibers to generate action potentials that at least partially relieve a symptom selected from a group of symptoms comprising urgent urination, frequent urination, urge incontinence, urgent urination with incontinence, frequent urination with incontinence, nocturia, ischuria, bladder discomfort, and bladder pain, and wherein the one or more electrical impulses is transmitted to the patient in a treatment session having a period from about 3 minutes to about three hours, followed by a period from about three hours to about one week wherein the one or more electrical impulses is not transmitted to the patient, and wherein one or more protocol parameters for a treatment session is selected individually for the patient, wherein the one or more protocol parameters comprising at least one of: a burst frequency, a number of pulses per burst, a duration of a pulse within a burst, a power of electrical impulses, a duration of an impulse-transmission session, a duration of a period during which impulses are not transmitted, a phase or phases of bladder-filling of a patient when electrical impulses are transmitted, and a range of bladder filling-volumes when electrical impulses are transmitted, and wherein the one or more protocol parameters is selected via:

performing measurements of bladder and urethra function of the patient;

using said measurements to estimate values of numerical parameters in a set of differential equations that represents modules of the bladder of the patient as coupled non-linear oscillators;

simulating a plurality of potential treatments by solving said differential equations with different protocol parameters; and selecting among said simulations the one having protocol parameters that minimize simulated bladder contractions.

20. The method of claim 19, wherein an energy source within the device is configured to generate shaped electrical impulses and transmit the shaped electrical impulses to the patient through a conducting medium within the device.

21. The method of claim 19, wherein the one or more electrical impulses is transmitted transcutaneously through an outer skin surface of the patient to generate an electrical impulse at or near the selected nerve fibers.

22. The method of claim 21, wherein the transmitting is carried out by transcutaneously passing an electrical current through the outer skin surface of the patient to a target region within the patient.

23. The method of claim 22, further comprising:

generating an electrical field at or near the device and shaping the electrical field such that the electrical field is sufficient to modulate a nerve at the target region; and wherein the electric field is not sufficient to modulate a nerve or a muscle between the outer skin surface and the target region.

24. The method of claim 23, wherein the electric field is not sufficient to produce movement of a skeletal muscle in a limb of the patient.

25. The method of claim 21, wherein the transmitting is carried out by generating a magnetic field via the device, wherein the magnetic field is exterior to the patient, wherein the magnetic field is sufficient to induce the one or more electrical impulses at or near the selected nerve fibers within the patient.

26. The method of claim 21, wherein at least one of the nerve fibers is at least from about 0.5 cm to about 2 cm below the outer skin surface of the patient.

27. The method of claim 19, wherein the one or more electrical impulse is constrained from modulating one or more nerves in a region between the skin surface and at least one of the selected nerve fibers.

28. The method of claim 19, wherein the selected nerve fibers are associated with a posterior tibial nerve of the patient.

29. The method of claim 19, wherein the selected nerve fibers are associated with both left and right posterior tibial nerves of the patient.

30. The method of claim 29, wherein the one or more electrical impulses is transmitted alternately to the left and right posterior nerves of the patient.

31. The method of claim 19, wherein at least one of the nerve fibers is selected from among: tibial nerve, pudendal nerve, sciatic nerve, superior gluteal nerve, lumbo-sacral trunk nerve, inferior gluteal nerve, common fibular nerve, posterior femoral cutaneous nerve, obturator nerve, common peroneal nerve, plantar nerve, sacral nerves S1, S2, S3, or S4, or nerves of the S1, S2, S3, or S4 dermatome, and sacral anterior root nerves.

32. The method of claim 19, wherein the one or more electrical impulses comprise bursts of pulses with a frequency from about 5 bursts per second (Hz) to about 100 bursts per second (Hz).

33. The method of claim 32, wherein each of the bursts contains from about 1 pulse to about 20 pulses.

34. The method of claim 32, wherein the pulses are full sinusoidal waves.

35. The method of claim 32, wherein each of the pulses is from about 50 microseconds to about 1000 microseconds in duration.

36. The method of claim 19, wherein a first power of the one or more electrical impulses is configured to be a predetermined percentage of a second power needed to first produce movement of a skeletal muscle in a limb of the patient.

37. The method of claim 19, wherein the one or more electrical impulses is transmitted preferentially when the patient's bladder-filling is in a phase selected from among: a refractory phase following urination wherein the patient has no desire to urinate; a phase beginning with a first desire to urinate and ending before a strong desire to urinate; and a phase beginning with a strong desire to urinate that cannot be ignored by the patient.

* * * * *